United States Patent
Latham et al.

(10) Patent No.: US 7,264,932 B2
(45) Date of Patent: Sep. 4, 2007

(54) NUCLEASE INHIBITOR COCKTAIL

(75) Inventors: Gary J. Latham, Austin, TX (US); Matthew M. Winkler, Austin, TX (US); Brittan L. Pasloske, Austin, TX (US); W. Antoni Kudlicki, Carlsbad, CA (US)

(73) Assignee: Applera Corporation, Foster City, CA (US)

( * ) Notice: Subject to any disclaimer, the term of this patent is extended or adjusted under 35 U.S.C. 154(b) by 23 days.

(21) Appl. No.: 10/786,875

(22) Filed: Feb. 25, 2004

(65) Prior Publication Data

US 2005/0014169 A1 Jan. 20, 2005

Related U.S. Application Data

(63) Continuation-in-part of application No. 10/675,860, filed on Sep. 30, 2003, now Pat. No. 7,163,793, which is a continuation of application No. 09/669,301, filed on Sep. 25, 2000, now Pat. No. 6,664,379.

(60) Provisional application No. 60/155,874, filed on Sep. 24, 1999.

(51) Int. Cl.
*C12Q 1/68* (2006.01)
*C07K 5/00* (2006.01)
*C07K 16/00* (2006.01)
*C12P 21/08* (2006.01)

(52) U.S. Cl. ............... 435/6; 530/330; 530/387.1; 530/388.26

(58) Field of Classification Search ............... 435/6; 530/350, 387.1, 388.26
See application file for complete search history.

(56) References Cited

U.S. PATENT DOCUMENTS

| | | | | |
|---|---|---|---|---|
| 4,564,593 A | * | 1/1986 | Tsukamoto et al. | 435/91.32 |
| 5,278,062 A | * | 1/1994 | Samal et al. | 510/392 |
| 5,346,994 A | * | 9/1994 | Chomczynski | 530/419 |
| 5,470,971 A | * | 11/1995 | Kondo et al. | 536/23.7 |
| 5,968,784 A | * | 10/1999 | Spinella et al. | 435/91.1 |
| 5,972,613 A | | 10/1999 | Somack et al. | 435/6 |
| 5,973,137 A | | 10/1999 | Heath | 536/25.4 |
| 6,110,968 A | | 8/2000 | Bucala et al. | 514/482 |
| 6,664,379 B1 | * | 12/2003 | Kudlicki et al. | 530/387.9 |
| 6,869,604 B1 | | 3/2005 | Rybak et al. | 424/94.61 |
| 2007/0032418 A1 | | 2/2007 | Shapiro et al. | 514/12 |

FOREIGN PATENT DOCUMENTS

| EP | 0896524 | 4/1997 |
|---|---|---|
| WO | WO97/40817 | 11/1997 |
| WO | WO 2004/005663 | 1/2004 |
| WO | WO 2004/076640 | 9/2004 |

OTHER PUBLICATIONS

"Basic Methods in Molecular Biology" Section 11-1 and 11-2, pp. 130-138, Edited by Davis et al. Elsevier Science Publishing Co., New Tork, New York (1986).*
Robbi et al. PNAS 75 (9) : 4344-4348 (Sep. 1978).*
Lee et al. Biochemistry 27 : 88545-8553 (1988).*
"Basic Methods in Molecular Biology" Section 5-2—5-3, pp. 44-50, Edited by Davis et al. Elsevier Science Publishing Co., New Tork, New York (1986).*
Material Safety data sheet for vanadyl ribonuclease complex downloaded from the New England Biolab, 2 pages.*
The Stratagene Catalog p. 39 (1988).*
Allewell and Sama, "The effect of ammonium sulfate on the activity of ribonuclease a," *Biochem. Biophys.* ACTA, 341:484-488, 1974.
Blackburn et al., "Ribonuclease inhibitor from human placenta: interaction with derivatives of ribonuclease A," *J. Biol. Chem.* 252:12488-12493, 1977.
Blumberg, "Creating a ribonuclease-free environment," *Methods Enzymol.* 152:20-24, 1987.
Cazenave, "Idiotypic-anti-idiotypic regulation of antibody synthesis in rabbits," *Proc. Natl. Acad. Sci. USA*, 74:5122-5125, 1977.
Chirgwin, et al., "Isolation of biologically active ribonucleic acid from sources enriched in ribonuclease," *Biochemistry* 18:5294-5299, 1979.
Chomczynski and Sacchi, "Single step method of RNA isolation by acid guanidinium thiocyanate-phenol-chloroform extraction," *Anal. Biochem.* 162:156-159, 1987.
Chomczynski, "Solubilization in formamide protects RNA from degradation," *Nucleic Acids Res.* 20:3791-3792, 1992.
Coburn and Mackie, "Overexpression, purification, and properties of *Escherichia coli* ribonuclease II," *J. Biol. Chem.* 271: 1048-1053, 1996.
Gilleland and Hockett Jr., "Stability of RNA molecules stored in gitc," *Biotechniques* 25:944-948, 1998.
Jocoli and Ronald, "Inhibition of ribonuclease activity by bentonite," *Can. J. Biochem.* 51:1558-1565, 1973.
Jones, "On the efficacy of commonly used ribonuclease inhibitors," *Biochem. Biophys. Res. Commun.* 69:469-474, 1976.
Lee et al., "The use of immobilized anti-ribonuclease antibodies in the isolation of polyribosomes," *Immunochemistry*, 9:210-213, 1972.
Lin, "Inactivation of pancreatic ribonuclease with hydroxylamine-oxygen-cupric ion," *Biochim. et Biophys. Acta* 263:680-682, 1972.
Mendelsohn and Young, "Efficacy of sodium dodecyl sulfate, diethyl pyrocarbonate, proteinase k and heparin using a sensitive ribonuclease assay," *Biochim. et Biophys. Acta* 519:461-473, 1978.
Murphy et al., "A potent, cost-effective RNase inhibitor," *Biotechniques* 18:1068-1073, 1995.

(Continued)

Primary Examiner—Ethan Whisenant
(74) *Attorney, Agent, or Firm*—Fulbright & Jaworski L.L.P.

(57) ABSTRACT

Methods and compositions for inhibiting and/or inactivating nucleases by using nuclease inhibitors are provided. The nuclease inhibitors comprise anti-nuclease antibodies and non-antibody nuclease inhibitors.

78 Claims, 8 Drawing Sheets

OTHER PUBLICATIONS

O'Leary, "Reducing the Impact of Endogenous Ribonucleases on Reverse Transcription-PCR Assay Systems," *Clinical Chemistry*, 45(4):449-450, 1999.

Pelham and Jackson, "An efficient mRNA dependent translation system for reticulocyte lysates," *Eur. J. Biochem.* 67:247-256, 1976.

Russo and Shapiro, "Potent inhibition of mammalian ribonucleases by 3' 5'-pyrophosphate-linked nucleotides," *J. Biol. Chem.* 274:14,902-14,908, 1999.

Sambrook, et al., "Molecular cloning, a laboratory manual," pp. 7.16-7.52, 1989.

Spackman et al., "The Disulfide Bonds of Ribonuclease," *J. Biol. Chem.* 235:648-659, 1960.

Spickler and Mackie, "Action of RNase ii and polynucleotide phosphorylase against RNase containing stem-loops of defined structure," *J. Bacteriology* 182(9): 2422-2427, 2000.

Trent et al., "A comparison of new world alphaviruses in the western equine encephalomyelitis complex by immunochemical and oligonucleotide fingerprint techniques," *J. Gen. Virol.*, 47:261-282, 1980.

Wolf et al., "A mechanism of the irreversible inactivation of bovine pancreatic ribonuclease by diethylpyrocarbonate ," *Eur. J. Biochem.* 13:519-525, 1970.

Wu, et al., "Methods in Gene Biotechnology," CRC Press, Boca Raton, FL, pp. 29-56, 1997.

Zale and Klibanov, "Why does ribonuclease irreversibly inactivate at high temperatures?," *Biochemistry* 25:5432-5444, 1986.

U.S. Appl. No. 60/547,721, filed Feb. 25, 2004.

U.S. Appl. No. 10/675,860, filed Sep. 30, 2003.

Devaux et al., "Inhibition of the catalytic properties of staphylococcus aureus nuclease by monoclonal antibodies" *Molecular and Cellular Biochemistry*, 74: 117-128, 1987.

Feldman M. et al., "Interaction of Rnase a with estrogen receptor from rat mammary tumor MTW-9," *Journal of Biological Chemistry*, 258: 5001-5004, 1983.

Simpson, "An improved method for mRNA isolation and characterization of in vitro translation products by Western blotting" *Gene*, 56: 161-171, 1987.

Iverson et al., "Inhibitors of angiogenesis selectivity reduce the malignant cell load in rodent models of human myeloid leukemias," *Leukemia*, 16:376-381, 2002 9 (abstract).

Jenkins and Shapiro, "Identification of small-molecule inhibitors of human angiogenin and characterization of their binding interactions guided by computational docking," *Biochemistry*, 42:6674-6687, 2003.

Jenkins et al., "Virtual Screening to Enrich Hit Lists From High-Throughput Screening: A Case Study on Small-Molecule Inhibitors of Angiogenin," *Proteins: Structure, Function, and Genetics*, 50:81-93, 2003.

Kao et al., "A small-molecule inhibitor of the ribonucleolytic activity of human angiogenin that possesses antitumor activity," *Proc. Natl. Acad. Sci. USA*, 99:10066-10071, 2002.

Russo et al., "Small Molecule Inhibitors of RNase A and Related Enzymes," *Methods enzymology*, 341:629-648, 2001.

Shapiro, "Cytoplasmic Ribonuclease Inhibitor," *Methods Enzymology*, 341:611-628, 2001.

Smith et al., "Potent Inhibition of ribonuclease A by oligo(vinylsulfonic acid)," *J. Biol. Chem.*, 278:20934-20938, 2003.

Talib and Hearst, "Initiation of RNA synthesis in vitro by vesicular stomatitis virus: single internal initiation in the presence of aurintricarboxylic acid and vanadyl ribonucleoside complexes," *Nucleic Acids Res.*, 11:7031-7042, 1983.

Venkataraman, The chemistry of synthetic dyes, Academic Press Inc., New York, vol. 1, 1952, pp. 241-247.

Worthington Nuclease, "Nuclease, Micrococcal (S7)," http://www.worthington-biochem.com/NFCP/default.html.

Fett, et al., "A monoclonal antibody to human angiogenin. Inhibition of ribonucleolytic and angiogenic activities and localization of the antigenic epitope", *Biochemistry*, 33:5421-5427, 1994.

Fransen et al., "Isolation of HIV-1 RNA from plasma: evaluation of seven different methods for extraction (part two)", *Journal of Virological Methods*, 76:153-157, 1998.

Shen et al., "Poly[G] improved protein productivity of cell-free translation by inhibiting mRNase in wheat germ extract", *Journal of Biotechnology*, 75:221-228, 1999.

\* cited by examiner

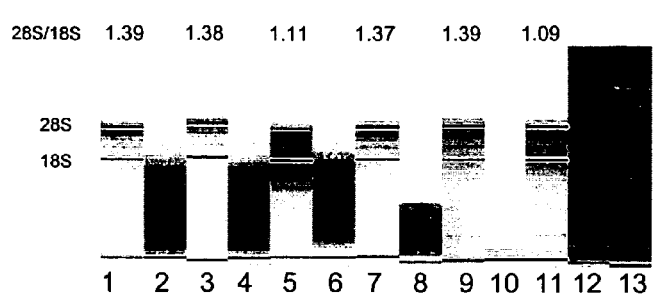

| # | RNA Challenge Conditions |
|---|---|
| 1. | Production source RNA control |
| 2. | Diluted pancreas lysate control |
| 3. | Diluted pancreas lysate + BpB |
| 4. | Bovine RNase A control |
| 5. | Bovine RNase A + BpB |
| 6. | EDN control |
| 7. | EDN + BpB |
| 8. | HPR control |
| 9. | HPR + BpB |
| 10. | RNase 1 control |
| 11. | RNase 1 + BpB |
| 12. | RNase T1 control |
| 13. | RNase T1 + BpB |

FIG. 4

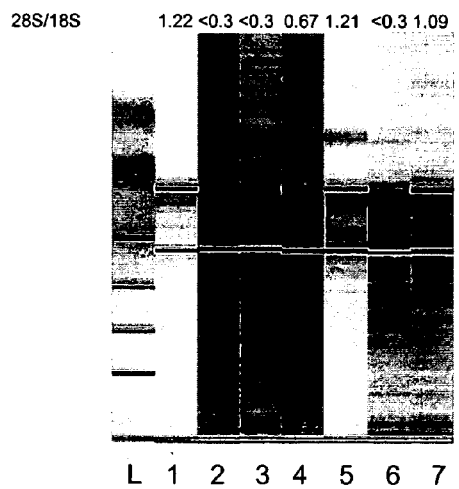

| # | RNA Challenge Conditions |
|---|---|
| 1. | Production source RNA control |
| 2. | RNase Mixture control |
| 3. | RNase Mixture + RIP |
| 4. | RNase Mixture + Anti-RNase T1 |
| 5. | RNase Mixture + RIP + Anti-RNase T1 |
| 6. | RNase Mixture + BpB |
| 7. | RNase Mixture + BpB + Anti-RNase T1 |

FIG. 5

Structure II

Structure III

NUCLEASE INHIBITOR COCKTAIL

This application is a continuation-in-part application of U.S. application Ser. No. 10/675,860 filed Sep. 30, 2003, now U.S. Pat. No. 7,163,793 which is a continuation of application Ser. No. 09/669,301 filed Sep. 25, 2000, now U.S. Pat. No. 6,664,379, which claims the benefit of U.S. Provisional Application No. 60/155,874, filed Sep. 24, 1999. The entire text of each of the foregoing applications is specifically incorporated herein by reference without disclaimer.

BACKGROUND OF THE INVENTION

1. Field of the Invention

The present invention relates generally to the field of molecular biology. More particularly, it concerns the inhibition and/or inactivation of nucleases (both deoxyribonucleases and ribonucleases) which can degrade DNA (deoxyribonucleic acid) and/or RNA (ribonucleic acid). Inhibition and/or inactivation of nucleases in the present invention employs at least one, and in many cases at least two, nuclease inhibitors. These nuclease inhibitors include anti-nuclease antibodies and non-antibody nuclease inhibitors.

2. Description of Related Art

The quality of an RNA preparation greatly affects the results obtained when analyzing it by a number of different molecular biology techniques such as northern blotting, ribonuclease protection assays and RT-PCR (Reverse Transcriptase-Polymerase Chain Reaction). Degraded RNA will produce a lower signal than in an equivalent intact RNA sample.

RNA is much more susceptible to degradation than DNA (Sambrook et al., 2001). RNA is readily hydrolyzed when exposed to conditions of high pH, metal cations, high temperatures and contaminating ribonucleases. A major cause of RNA degradation is ribonuclease contamination, and this must be guarded against in virtually all RNA-related procedures, including RNA isolation, mRNA purification, RNA amplification, RNA storage, northern blotting, nuclease protection assays, RT-PCR, in vitro transcription and/or translation and RNA diagnostics. In addition to the endogenous ribonucleases from cells and tissues, skin secretions and airborne bacteria and/or fungi are common sources of ribonuclease. To minimize ribonuclease contamination, appropriate precautions must be followed when handling RNA (Blumberg, 1987; Wu, 1997).

Ribonucleases are difficult to inactivate. For example, bovine pancreatic ribonuclease A (RNase A) has no activity at 90° C. However, if the enzyme is quickly cooled to 25° C., the activity is fully restored. This process is known as reversible thermal denaturation. If the RNase A is incubated at 90° C. over time, then decreasing fractions of the activity are recovered at 25° C. This process is known as irreversible thermoinactivation. At 90° C., it takes several hours to inactivate RNase A (Zale and Klibanov, 1986). Much of the lost activity is attributed to disulfide interchange (Zale and Klibanov, 1986). Further, the inventors and others have found that ribonucleases can even withstand autoclaving (121° C., 15 psi, 15 minutes) to some degree. Spackman et al. (1960) tested the stability of RNase A and concluded that it was stable to heat, extremes of pH, and the protein denaturant, urea, results emphasizing the difficulty researchers have had inactivating ribonucleases. For the above reason, a variety of methods other than heating have been developed to inhibit or inactivate ribonucleases. These methods, and their disadvantages, are described below.

In one method of destroying RNases, diethyl pyrocarbonate (DEPC) is added to final concentration of 0.1% to molecular biology reagents, glassware or electrophoresis apparatus, followed by incubating at 37° C. for several hours and then autoclaving for 15-20 minutes to destroy the DEPC (Wolf et al., 1970). DEPC reacts with the $\epsilon$-amino groups of lysine and the carboxylic groups of aspartate and glutamate both intra- and intermolecularly (Wolf et al., 1970). This chemical reaction forms polymers of the ribonuclease. However, there are several disadvantages to using DEPC: (1) It is a possible carcinogen and is hazardous to humans; (2) some commonly used molecular biology reagents such as Tris react with and inactivate DEPC; (3) treatment of samples with DEPC is time-consuming; (4) DEPC reacts with the adenine residues of RNA, rendering it inactive in in vitro translation reactions (Blumberg, 1987) and 5). If all of the DEPC is not destroyed by autoclaving, remaining trace amounts may inhibit subsequent enzymatic reactions.

Traditionally, RNA is stored in DEPC-treated water or TE buffer. However, the RNA is not protected from degradation if the sample or the storage solution has a minor ribonuclease contamination. It has been suggested that RNA be stored in ethanol, formamide, or guanidinium to protect an RNA sample from degradation because these environments minimize ribonuclease activity (Chomczynski, 1992; Gilleland and Hockett, 1992). The obvious disadvantage is that the RNA sample cannot be directly utilized for analysis or enzymatic reactions unless the ethanol, formamide, or guanidinium is removed.

Guanidinium thiocyanate is commonly used to inhibit RNases during RNA isolation (Chomczynski and Sacchi, 1987; Sambrook et al., 2001). A high concentration of guanidinium thiocyanate combined with $\beta$-mercaptoethanol is used to isolate RNA from tissues, even those that are rich in ribonucleases, such as pancreas (Chirgwin et al., 1979). Guanidinium is an effective inhibitor of most enzymes due to its chaotropic nature. However, if RNA is dissolved in guanidinium, then it must first be purified from the guanidinium prior to being used in an enzymatic reaction.

Vanadyl-ribonucleoside complexes (VRC) may be used to inhibit RNases during RNA preparation (Berger and Birkenmeier, 1979). The drawback to using VRC, is that VRC strongly inhibits the translation of mRNA in cell-free systems and must be removed from RNA samples by phenol extraction (Sambrook et al., 2001).

Favaloro et al. (1980) employed macaloid, a clay, to absorb RNases. A limitation of this method is that it is difficult to completely remove the clay from RNA samples. Other reagents have been used to inhibit ribonucleases including sodium dodecylsulfate (SDS), ethylenediamine tetraacetic acid (EDTA), proteinase K, heparin, hydroxylamine-oxygen-cupric ion, bentonite and ammonium sulfate (Allewell and Sama, 1974; Jocoli and Ronald, 1973; Lin, 1972; Jones, 1976; Mendelsohn and Young, 1978). None of these reagents are strong inhibitors alone. Like many of the RNase inhibitors already described, although these chemicals inhibit RNase activity, they also may inhibit other enzymes such as reverse transcriptase and DNase I. Therefore, the RNA must be purified away from the inhibitory reagent(s) before it can be subjected to other enzymatic processes.

Two types of proteinaceous RNase inhibitors are commercially available: human placental ribonuclease inhibitor (Blackburn et al., 1977) and PRIME Inhibitor™ (Murphy et al., 1995). RNases of the class A family bind tightly to these protein inhibitors and form noncovalent complexes that are enzymatically inactive. The major disadvantage of these inhibitors is that they have a narrow spectrum of specificity. They do not inhibit other classes of RNases. Another disadvantage when using placental ribonuclease inhibitor is that it denatures within hours at 37° C., particularly under oxidizing conditions, releasing the bound ribonuclease.

Heat has been used to inactivate RNase A by mediating the breakage of disulfide bonds. Zale and Klibanov (1986) performed inactivation of RNase A at 90° C. and pH 6.0 for 1 hour, which induced the following chemical changes: disulfide interchange, β-elimination of cysteine residues, and deamidation of asparagine. This type of heat treatment did not completely inactivate the ribonuclease. A major disadvantage is that a long-term, high-temperature treatment (90-100° C.) is incompatible with RNA. Such treatment promotes the hydrolysis of RNA. In fact, the inventors have found that total RNA incubated at 65° C. for several hours is almost completely degraded. Thus, treating an RNase sample with extreme heat to inactivate ribonucleases will mediate the destruction of the RNA which the user is trying to protect.

SUMMARY OF THE INVENTION

The present invention provides methods, compositions, solutions, and kits for inhibiting and/or inactivating nucleases. Other embodiments of this invention include methods and compositions for performing in vitro translation, transcription, reverse transcription, or coupled transcription/translation reaction. In some aspects, the present invention relates to methods for inhibiting nucleases with one or more nuclease inhibitors and compositions comprising nuclease inhibitors that can be used in such methods.

The present invention has many applications, including, but not limited to, nucleic acid related procedures. Non-limiting examples of nucleic acid procedures include RNA and/or DNA isolation and/or purification, mRNA purification, cDNA purification, RNA and/or DNA storage, northern blotting, southern blotting, RNA amplification, nuclease protection assays, PCR and RT-PCR, in vitro transcription and/or translation, DNA removal or clean-up from RNA preparations, and RNA diagnostics.

A particular aspect of the present invention includes a method comprising: (a) obtaining at least a first nuclease inhibitor; (b) obtaining at least a second nuclease inhibitor; (c) obtaining a composition; and (d) admixing the first nuclease inhibitor, the second nuclease inhibitor and the composition to form an admixture; wherein nucleases that may be present in the admixture are inhibited. In certain non-limiting embodiments, admixing is defined as comprising mixing the first and second nuclease inhibitors to form a nuclease inhibitor cocktail and mixing the nuclease inhibitor cocktail with the composition. In other aspects, obtaining the first and second nuclease inhibitors comprises obtaining a nuclease inhibitor cocktail comprising the first nuclease inhibitor and the second nuclease inhibitor. The admixture can include at least one nuclease.

Another aspect of this invention includes a method of performing an in vitro translation, transcription, RNA isolation, reverse transcription, RNA amplification, DNA removal or coupled transcription/translation reaction comprising obtaining a composition, the composition comprising a first nuclease inhibitor and a second nuclease inhibitor and placing the composition in an in vitro translation reaction, transcription reaction, reverse transcription reaction, or a coupled transcription/translation reaction. In many cases, the in vitro translation reaction comprises at least one nuclease, which may be a ribonuclease, a deoxyribonuclease, or a nonspecific nuclease, as described elsewhere in the specification. Of course, the reaction may further comprise a combination of two or more nucleases. The in vitro translation reaction will also comprise a nucleic acid, which will usually be RNA, in particular, the mRNA to be employed in translation. However, the reaction may also comprise DNA, for example, as the result of a cell-based isolation procedure or a coupled, linked, or separated transcription/translation reaction performed according to any of a number of methods known to those of skill in the art. The anti-nuclease(s) can be any of those described throughout this specification. In a particular aspect, the method further includes obtaining a lysate and employing the lysate in the in vitro translation reaction. These methods will often involve the use of cell-free translation systems, such as, for example, the reticulocyte lysate, wheat germ lysate, Drosophila lysate, yeast lysate, etc. systems known to those of skill in the art and described in the literature and elsewhere in the specification.

In still another embodiment, this invention includes a solution comprising at least a first nuclease inhibitor and a second nuclease inhibitor. In further aspects, the solution can also include a nucleic acid molecule, e.g., DNA and/or RNA. The solution can also include a nuclease, e.g., a deoxyribonuclease and/or a ribonuclease. Such solutions may be "nuclease inhibitor cocktails," "ribonuclease (or RNase) inhibitor cocktails," "deoxyribonuclease (or DNase) inhibitor cocktails," etc., as appropriate, based on their activities. In other embodiments, the solution is defined as a reagent used in molecular biology. Non-limiting examples of reagents that can be used with all of the embodiments of the present invention include water, tris-EDTA buffer (TE), sodium chloride/sodium citrate buffer (SSC), MOPS/sodium acetate/EDTA buffer (MOPS), Tris buffer, ethylenediamine tetraacetic acid (EDTA), nucleic acid hybridization buffer, sodium acetate buffer, DNase I digestion buffer, transcription buffer, reverse transcription buffer, cell free extract for in vitro translation, in situ hybridization buffer, or nucleic acid storage buffer/solution.

The invention also relates to kits for the performance of various microbiological procedures, which kits comprise the nuclease inhibitors described herein. These kits may contain either a single nuclease inhibitor, or multiple nuclease inhibitors. In some cases, these kits may contain a cocktail of nuclease inhibitors, as described elsewhere in the specification. In one particular embodiment, the kit is further defined as a kit for in vitro translation, in vitro transcription, RNA isolation, reverse transcription, RNA amplification or a DNA removal reaction. These kits can comprise at least one anti-nuclease antibody and some or all of the necessary components for, or to make, a cell-free translation system. Such systems are known to those of skill in the art.

The methods, solutions, compositions, and kits of the present invention can include obtaining a third, fourth, fifth, sixth, seventh, eighth, ninth, tenth (or more) nuclease inhibitor(s). The methods of the invention frequently involve the preparation of a nuclease inhibitor cocktail by the mixing of the first and second nuclease inhibitors. Such a cocktail may be mixed with the composition at any time. For example, the cocktail may be prepared and then relatively immediately mixed with the composition. Alternatively, the cocktail may be prepared in advance. In many cases, the cocktail may be prepared and provided as a commercial product to a researcher, and the researcher practices the invention by obtaining the first and second nuclease inhibitors in the form of the cocktail and then admixing the cocktail with the composition.

The compositions of the present invention can include a nucleic acid. The nucleic acid can be DNA (including, but not limited to cDNA) and RNA (including, but not limited to mRNA). In some embodiments, the composition comprises DNA and/or RNA that has been purified. In particular non-limiting aspects of this invention, the compositions can be further defined as a cell lysis buffer, a tissue lysis buffer, an RNA extraction solution, an in vitro translation reaction mixture, an in vitro transcription reaction mixture, a reverse transcription reaction mixture, an RNA amplification reaction, or a coupled transcription/translation reaction mixture. Under circumstances where there are nucleases present in the compositions, those nucleases can be inhibited to some extent. Note that complete inactivation or inhibition of nucleases is not required to obtain benefit from the invention. Further, note that these aspects of the invention are not limited to cases where one knows that there is a nuclease present in the composition. Therefore, it is entirely within the scope of the invention to use the inhibitors disclosed herein to treat a composition which may have nucleases in it, or even a composition which a researcher is confident does not have nucleases in it, but which the researcher wishes to treat out of an abundance of caution. In some embodiments, the composition will have a nuclease present, for example a ribonuclease (RNase), deoxyribonuclease (DNase), a non-specific nuclease, or a combination of two or more of these, as described elsewhere in this specification. Some embodiments involve inhibition of RNase, DNase, a non-specific nuclease, or a combination thereof. A composition comprising at least two nuclease inhibitors is referred to herein as a "nuclease inhibitor cocktail," and includes, but is not limited to, the specific inhibitors disclosed elsewhere in this specification. The composition treated according to the methods of the invention can be any composition that one of skill in the art would find beneficial to treat in order to prevent nuclease activity in the composition. In most cases, the composition will be liquid, although solid compositions,1 such as a matrix comprising immobilized nuclease inhibitor, may be treated as well.

The first and second nuclease inhibitors of the present invention can be, independently, a small molecule, an oligonucleotide, a proteinaceous compound, or an affinity resin. The small molecule can include an organic compound, an inorganic compound, a salt, or a chaotrope. In particular embodiments, the small molecule comprises an organic compound. The organic compound can be hydrophilic, hydrophobic, or amphipathic compound. In particular embodiments, the organic compound comprises oligovinylsulfonic acid (OVA), aurintricarboxylic acid (ATA), aflatoxin, 2-nitro-5-thiocyanobenzoic acid, iodoacetate, N-bromosuccinimide, p-chloromercuribenzoate, diethyl pyrocarbonate, ethanol, formamide, guanidinium thiocyanate (GdnSCN), tyrosine-glutamate copolymer, DNP-poly (A), dinitrofluorobenzene, decanavanate, polyvinylsufonic acid, hydrobenzoinphosphate, phenylphosphate, putrescine, haloacetate, dinitrofluorobenzene, phenylglyoxal, bromopyruvic, hydroxylamine-oxygen-cupric ion, a vanadyl complex, 8-amino-5-(4'-hydroxy-biphenyl-4-ylazo)-naphthalene-2-sulfonate, 6-hydroxy-5-(2-hydroxy-3,5-dinitrophenylazo)-naphthalene-2-sulfonate, 3,3'-dimethylbiphenyl-4,4'-bis(2-amino-naphthylazo-6-sulfonate), 4,4'-dicarboxy-3,3'-bis(naphthylamido)-diphenylmethanone, 3,3'-dicarboxy-4,4'-bis(4-biphenylamido) diphenylmethane, or 3,3'-dicarboxy-4,4'-bis(3-nitrophenylamido)diphenylmethane.

In other embodiments of the present invention, the organic compound is further defined as a nitrogenous base, a chelator, a reductant, or a detergent. Nitrogenous bases that can be used with the present invention include purines, pyrimidines, and related derivatives. In particular embodiments, the nitrogenous base can be coupled to a sugar moiety to form nucleosides or nucleotides. Other non-limiting examples include cytidine-N3-oxide 2'-phosphate, 2'CMP, ppAp, Ap3A, Ap4A, Ap5A, ATP, 5'AMP, 5'ADP, 3'UMP, 2'UMP, 2'CMP, pAp (5'P-A-3'P), dUppAp, dUppA2'p, pdUppAp, pTp, pTppAp, TpdA, TppdA, 4-thiouridine 3'p, 5-nitro-uracil, 5-aminoethyl-uracil or (Bromoacetamido)nucleoside. In still another embodiment of the present invention, the nuclease inhibitor comprises a reductant. The reductant can be a compound capable of transforming an oxidized molecule or moiety to a reduced state. Non-limiting examples include Cysteine, DTT, 2-ME, TCEP, (+/−)-trans-1,2-bis(2-mercaptoacetamido)cyclohexane (BMC), and Cys-Glu-Cys tripeptide ("CGC"). In another aspect of the present invention, the nuclease inhibitor can include a chelator. Non-limiting examples include EDTA, EGTA, BAPTA, Citrate, NTP, and dNTP. The nuclease inhibitor can even comprise a detergent. Examples of detergents that can be used with the present invention include SDS, deoxycholate, and N-laurylsarcosine, NP 40, Tween 20, and Triton X-100.

The small molecule nuclease inhibitors of the present invention can include a compound comprising a structure selected from Tables 1 and 2, below. In particular aspects, the compound can be selected from the group consisting of NCI-65828, NCI 65845, benzopurpurin B, NCI-65841, NCI 79596, NCI-9617, NCI-16224, suramin, direct red 1, NCI-7815, NCI-45618, NCI-47740, prBZBP, NCI-65568, NCI-79741, NCI-65820, NCI-65553, NCI-58047, NCI-65847, xylidene ponceau 2R, eriochrome black T, amaranth, new coccine, acid red 37, acid violet 7, NCI-45608, NCI-75661, NCI-73416, NCI-724225, orange G, NCI 47755, sunset yellow, NCI-47735, NCI-37176, violamine R, NCI-65844, direct red 13, NCI-45601, NCI 75916, NCI-65546, NCI-65855, NCI-75963, NCI-45612, NCI-8674, NCI-75778, NCI-34933, NCI-1698, NCI-7814, NCI-45550, NCI-77521, cefsulodin, NCI-174066, NCI-12455, NCI-45541, NCI-79744, NCI-42067, NCI-45571, NCI-45538, NCI-45540, NCI-9360, NCI-12857, NCI-D726712, NCI-45542, NCI-7557, S321443, NCI-224131, NCI-45557, NCI-1741, NCI-1743, NCI-227726, NCI-16163, NCI-16169, NCI-88947, NCI-17061, NCI-37169, beryllon II, CB-0181431, CB-473872, JLJ-1, JLJ-2, JLJ-3, CB-467929, CB-534510, CB-540408, CB-180582, CB-180553, CB-186847, CB-477474, CB-152591, NCI-37136, NCI-202516, CB-039263, CB-181145, CB-181429, CB-205125, and CB-224197.

In particular aspects of this invention, a nuclease inhibitor may include a compound comprising an aromatic structure. In other embodiments, the aromatic structure may be a polycyclic aromatic structure. A non-limiting example of nuclease inhibitors according to the invention include an aromatic structure of:

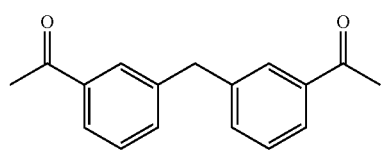

A further non-limiting example of nuclease inhibitors of the present invention include a polycyclic aromatic structure of:

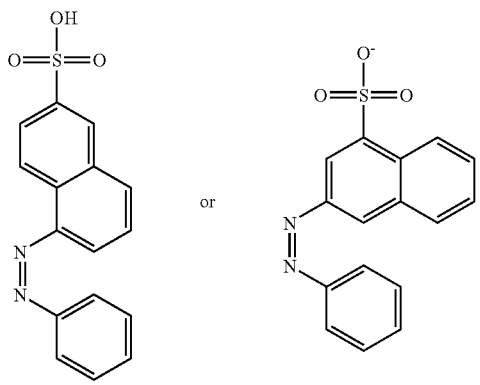

In preferred embodiments, the nuclease inhibitor comprises any one of the following structures:

Modifications or derivatives of the above aromatic structures are also contemplated as being useful with the methods and compositions of the present invention. Non-limiting examples of modifications that can be made to these structures include the addition or removal of lower alkanes such as methyl, ethyl, propyl, or substituted lower alkanes such as hydroxymethyl or aminomethyl groups; carboxyl groups and carbonyl groups; hydroxyls; nitro, amino, amide, and azo groups; sulfate, sulfonate, sulfono, sulfhydryl, sulfonyl, sulfoxido, phosphate, phosphono, phosphoryl groups, and halide substituents. Additional modifications can include an addition or a deletion of one or more atoms of the atomic framework, for example, substitution of an ethyl by a propyl, substitution of a phenyl by a larger or smaller aromatic group, etc. Alternatively, in a cyclic or bicyclic structure, hetero atoms such as N, S, or O can be substituted into the structure instead of a carbon atom.

In other aspects of the present invention, the nuclease inhibitor is NCI-65828. The nuclease inhibitor may also be a derivative of NCI-65828. The derivative of NCI-65828 may include at least one modification selected from the group consisting of: a reduction of the azo to hydrazido, replacement of the azo by an amide, an attachment of a hydroxyl group to position 6 of the naphthalene ring, an

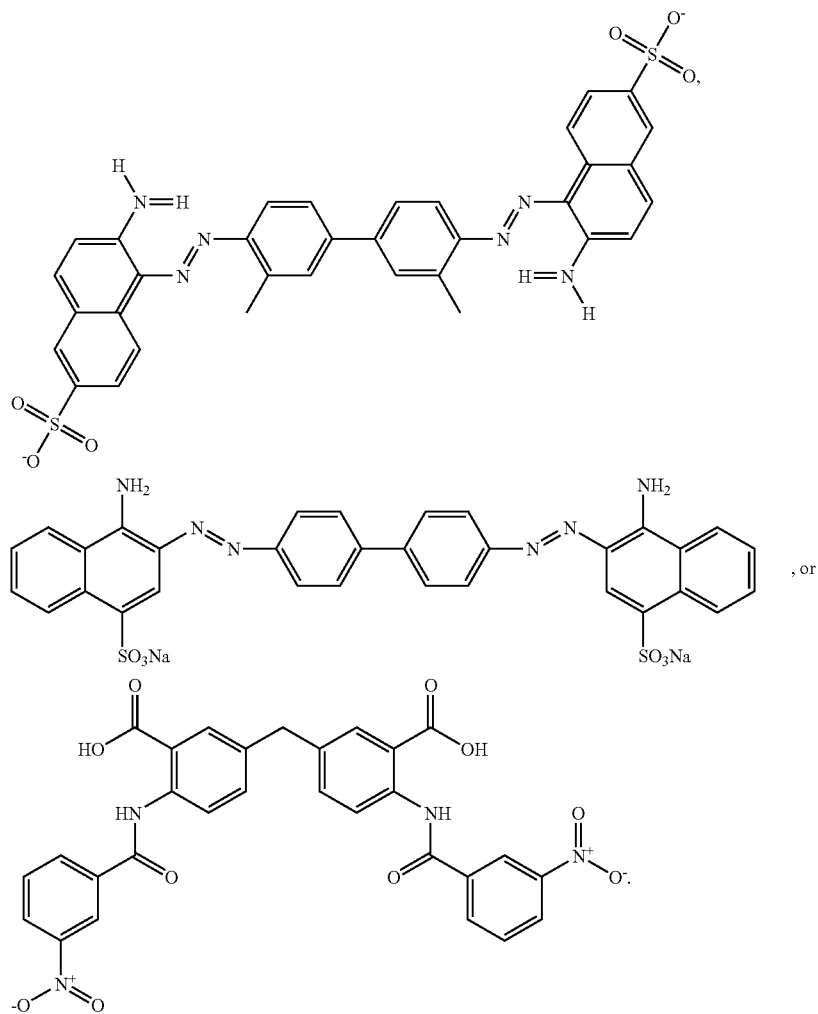

attachment of an electron-withdrawing group to position 6 of the naphthalene ring, replacement of a carbon atom in an aromatic ring with a nitrogen or an oxygen, and a replacement of the hydroxyl group on the biphenyl component with a sulfonate. In another aspect, the derivative of NCI-65828 may include at least one modification selected from the group consisting of: an addition of a hydrogen-bonding group and substitution of a hydroxyl group with an anionic group to the biphenyl component. The hydrogen-bonding group may be selected from the group consisting of a hydroxyl, an amino, and an amide. The anion may be selected from the group consisting of a carboxylate, a sulfate, a sulfonate, a phosphate, and a phosphonate.

In another embodiment, the nuclease inhibitor may be CB-473872. The nuclease inhibitor may also be a derivative of CB-473872. The derivative of CB-473872 may include an addition of at least one of a hydrogen-bonding group selected from the group consisting of: a hydroxyl, an amino, a methyldiamino, a hydroxyethyl, an ethyl-N-formamido, a carboxyamido, a carboxy, a 2-oxo-N-piperidinyl, and a p-benzoyl. In another embodiment, the derivative of CB-473872 comprises Structure II (FIG. 12) or Structure III (FIG. 13), wherein: $R_0$ is —H, —$NH_2$, or —OH; $R_3$ is —H, —$CH_2OH$, or $CONH_2$; $R_4$ is —H, —COOH, or 2-oxo-N-piperidinyl; $R_5$ is —H or p-benzoyl group. The derivative of CB-473872 may also include a replacement of a carbon atom in an aromatic ring with a nitrogen or an oxygen.

The nuclease inhibitor in other aspects can be an inorganic compound. The inorganic compound can include elements other than carbon such as metallic ions or complexes such as $Mg^{+2}$, $Mn^{+2}$, $Zn^{+2}$, $Fe^{+2}$, $Ca^{+2}$ or $Cu^{+2}$. In other embodiments, the nuclease inhibitor can be a salt. The salt can be monovalent or multivalent. In particular aspects, the salt is $(NH_4)_2SO_4$, NaCl, KCl, or NaCitrate. The nuclease inhibitor can also be a chaotrope. The chaotrope can be a chemical that disrupts the structure of water and/or promotes the solubility of nonpolar substances in polar solvents such as water. The chaotrope can be $SCN^-$, $Li^+$, $ClO_4^-$, or guanidinium.

In yet another embodiment of the present invention, the nuclease inhibitor can be a proteinaceous compound. The proteinaceous compound can include a peptide, a polypeptide, or a protein. In other aspects, the proteinaceous compound is an RNase inhibitor protein (RIP), a protease, a tyrosine-glutamate copolymer, actin, or RraA. The RIP can be obtained from a human, a chimpanzee, a rat, a mouse, a pig, or a yeast. The RIP can also be obtained by recombinant means and derivatives therein. The protein may also be a protease that irreversibly inactivates the RNase by cleaving the nuclease into peptide fragments. Non-limiting examples of proteases that can be used with the present invention include proteinase K, subtilisin, other alkaline proteases, acid proteases (e.g., pepsin), and pancreatic proteases (e.g., elastase, trypsin, and chymotrypsin).

In certain embodiments, the proteinaceous material is an antibody. The antibody can be, but is not limited to, a soluble anti-nuclease antibody. The soluble anti-nuclease antibody can be a polyclonal or monoclonal antibody. The anti-nuclease antibody can be an anti-ribonuclease antibody, an anti-deoxyribonuclease antibody or antibodies to non-specific nucleases. The invention may comprise the use of any number of anti-nuclease antibodies with various specificities. The invention includes the use of a mixture of two anti-nuclease antibodies that each inhibit a different nuclease. However, mixtures of three, four, or more anti-nuclease antibodies, each of which inhibit different or the same nucleases, may be used. The anti-ribonuclease antibodies of the present invention are capable of binding to one or more of RNase A, a member of the RNase A family, RNase B, RNase C, RNase 1, RNase T1, RNase T2, RNase L, a member of the RNase H family, a member of the angiogenin RNase family, eosinophil RNase, a micrococcal nuclease, an S1 nuclease, a member of the mammalian ribonuclease 1 family, a member of the ribonuclease 2 family, a messenger RNA ribonuclease, 5'-3' exoribonuclease, 3'-5' exoribonuclease, a decapping enzyme, a deadenylase, RNase P, RNase III, RNase E, RNase I, RNase HI, RNase HII, RNase M, RNase R, RNase IV, F; RNase P2,O, PIV, PC, RNase N, RNase II, PNPase, RNase D, RNase BN, RNase T, RNase PH, OligoRNase, RNase R, RNase Sa, RNase F1, RNase U2, RNase Ms, or RNase St. In other aspects, the anti-deoxyribonuclease antibodies are capable of binding to DNase 1. Some involve antibodies capable of binding to a non-specific nuclease such as S1 nuclease or micrococcal nuclease. The non-specific nucleases may degrade both RNA and DNA.

The nuclease inhibitor can also be an oligonucleotide. The oligonucleotide can be a DNA oligonucleotide, an RNA oligonucleotide, or thiol-containing or blocked. oligonucleotide. In specific embodiments, the oligonucleotide is a non-cleavable oligonucleotide, an aptamer, a DNP-Poly(A), a competitive inhibitor comprising a ribonucleoside, a deoxyribonucleoside, or a dideoxyribonucleoside.

In other aspects of this invention, the nuclease inhibitor can include an affinity resin. The affinity resin can be charged or uncharged. The affinity resin can be capable of binding other compounds such as proteinaceous compounds. In specific aspects, the affinity resin is SP resin, sulfopropyl sepharose, or sulfopropyl cation exchange resin.

In more particular embodiments of the present invention, the first nuclease inhibitor can include an anti-nuclease antibody or a small molecule and the second nuclease inhibitor comprises an RNase inhibitor protein. The anti-nuclease antibody can be soluble. The anti-nuclease antibody can be an anti-RNase T1 antibody or an anti-RNase 1 antibody. The RNase inhibitor protein can be obtained from a human, a chimpanzee, a rat, a mouse, a pig, yeast, or obtained by recombinant means, or derivatives therein. The small molecule can include an organic compound, an inorganic compound, or a salt.

In yet another aspect of this invention, the first nuclease inhibitor can comprise an anti-nuclease antibody and the second nuclease inhibitor can comprise a small molecule or an anti-nuclease inhibitor. The anti-nuclease antibodies can be a soluble. The anti-nuclease antibodies can be anti-RNase T1 antibodies and/or anti-RNase 1 antibodies. The small molecule can include an organic compound, an inorganic compound, or a salt. In other aspects, the first and second nuclease inhibitors in other embodiments of the present invention can include anti-nuclease antibodies.

In yet another embodiment of the present invention, the first and second nuclease inhibitors can, independently, be small molecules. The first nuclease inhibitor can be benzopurourin B and the second nuclease inhibitor can include an organic compound, an inorganic compound, or a salt. In other embodiments, the second nuclease inhibitor can be an RNase inhibitor protein, citrate, EDTA, OVA, SDS, Ap5A, proteinase K, an anti-RNase T1 Ab, or an SP resin. In still another aspect of this invention, the first and second nuclease inhibitors can be, independently, an RNase inhibitor protein, citrate, or EDTA. In particular embodiments, the first nuclease inhibitor can be OVA and the second nuclease inhibitor can be SDS.

Other nuclease inhibitors that can be used in the methods and compositions of the present invention are discussed throughout the specification, e.g., in the detailed description of the invention, the description of related art, the examples, the claims, and the cited references. Using the information provided in this specification, one of skill in the art will be able to identify additional compounds that may be employed in practicing the present invention.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any method or composition of the invention, and vice versa. Furthermore, compositions and kits of the invention can be used to achieve methods of the invention.

Throughout this application, the term "about" is used to indicate that a value includes the standard deviation of error for the device or method being employed to determine the value.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 3A shows NaCitrate Inhibits RNase A Activity. FIG. 3B shows NaCl inhibits RNase A activity.

FIG. 4 Intactness of total RNA challenged with RNases in the presence of BpB. Lane 1: Production source RNA control; Lane 2: Diluted pancreas lysate control; lane 3: Diluted pancreas lysate+BpB; lane 4: Bovine RNase A control; lane 5: Bovine RNase A+BpB; lane 6: EDN control; lane 7: EDN+BpB; lane 8: HPR control; lane 9: HPR+BpB; lane 10: RNase 1 control; lane 11: RNase 1+BpB; lane 12: RNase T1 control; lane 13: RNase T1+BpB.

FIG. 5 Use of Anti-RNase T1 in combination with RIP or Benzopurpurin B (BpB) effectively inhibits RNase A and RNase T1 activities. Lane 1 RNA control. Lane 2 RNase mixture control. Lane 3 RNase mixture+RIP. Lane 4 RNase mixture+Anti-RNase. T1. Lane 5 RNase mixture+RIP+Anti-RNase T1. Lane 6 RNase mixture+BpB. Lane 7 RNase mixture+BpB+Anti-RNase T1.

DETAILED DESCRIPTION

Figure 1:
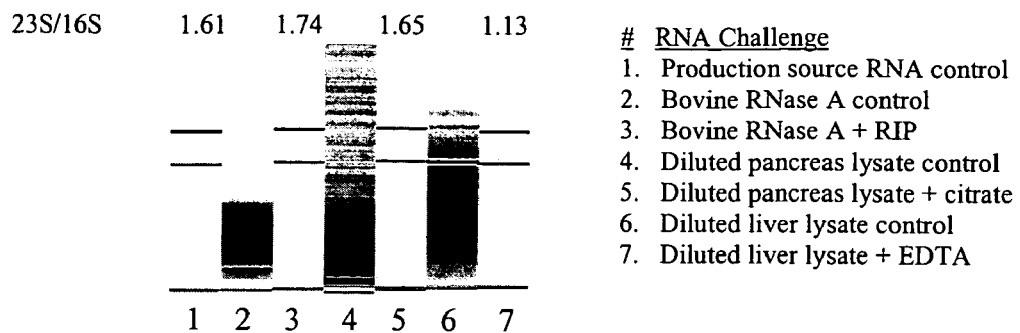
FIG. 1 Intactness of Total RNA challenged with RNases in the presence of RIP, citrate or EDTA. Lane 1: production source RNA control. Lane 2: bovine RNase A control. Lane 3: Bovine RNase A+RIP. Lane 4: diluted pancrease lysate control. Lane 5: diluted pancrease lysate+citrate. Lane 6: diluted liver lysate control. Lane 7: diluted liver lysate+EDTA.

The methods and compositions of the present invention provide for rapidly inhibiting and/or inactivating nucleases using anti-nuclease antibodies, non-antibody nuclease inhibitors, or both. By employing the methods and compositions of the present invention, a sample of DNA or RNA maintains its intact, full-length form during production and storage.

THE PRESENT INVENTION

The present invention comprises methods and compositions for rapidly inhibiting and/or inactivating nucleases (deoxyribonucleases (DNases) and ribonucleases (RNases)) using at least two nuclease inhibitors. These nuclease inhibitors may be one or more anti-nuclease antibodies, one or more non-antibody nuclease inhibitors, or a combination of at least one anti-nuclease antibody and at least one non-antibody nuclease inhibitor. The non-antibody nuclease inhibitors may be proteinaceous inhibitors, non-proteinaceous inhibitors, small molecules and/or organic compounds. Of course, one can determine other nuclease inhibitors by employing the methods disclosed.

In one presently preferred commercial embodiment, the nuclease inhibitor cocktail is a mixture of protein-based ribonuclease inhibitors that non-covalently bind and inactivate RNase A, B and C in addition to RNase 1 and RNase T1. This nuclease inhibitor cocktail is distinct from human placental ribonuclease inhibitor in that it has more robust interaction with RNases and does not release active RNases in the absence of dithiothreitol (DTT) or other reducing agents. It is an antibody-based, RNase-free mixture of different RNase inhibitors which can be useful in solving many RNase contamination problems. The nuclease inhibitor cocktail designed to block RNase A, B, C, RNase T1 and RNase 1 activities may be provided in some embodiments with final concentrations in the cocktail of 25 U/µl (~9 mg/ml) of anti-RNase A, 4.5 mg/ml of anti-RNase 1 and 4.5 mg/ml of anti-RNase T1. However, any concentrations that accomplish the goals of the invention are within the scope of the invention.

The present invention can be employed to inhibit and/or inactivate nucleases, thereby providing reagents that are free of RNase activity and/or DNase activity. For example, the anti-RNase antibodies of the present invention have a broader spectrum than human placental RNase Inhibitor Protein (RIP), inhibit common eukaryotic and prokaryotic nucleases (RNase A, B, C, RNase 1, T1, etc.), do not interfere with action of SP6, T7, T3 polymerase, M-MLV Reverse Transcriptase or Taq DNA polymerase.

These antibodies are also effective from pH 5.0 to 8.5, and are active from 37° C. to 65° C.

Definitions

The terms "inhibiting," "reducing," or "prevention," or any variation of these terms, when used in the claims and/or the specification includes any measurable decrease or complete inhibition to achieve a desired result. "Inhibiting" does not require complete nuclease inactivation or even substantial nuclease inactivation. The term "substantial inhibition" connotes that there is no substantial degradation of DNA or RNA detected in a composition that may include DNA or RNA.

"Substantial" degradation is defined as degradation that would impair the use of the DNA or RNA in the types of protocols described in this specification.

As used herein, the terms "nuclease inactivation" or the "inactivation of nucleases" denotes that there is no detectable degradation of the sample DNA or RNA under the assay conditions used, and that the nuclease is irreversibly rendered inoperative.

The term "substantially inactivated" connotes that there is no substantial degradation of DNA or RNA detected in a composition that may contain DNA or RNA, and that the nuclease is irreversibly rendered inoperative.

A "modification" of a particular compound includes a closely related compound having, in one embodiment, one or more altered substituents on an otherwise identical or substantially similar atomic framework. Altered substituents include addition or removal of lower alkanes such as methyl, ethyl, propyl, or substituted lower alkanes such as hydroxymethyl or aminomethyl groups; carboxyl groups and carbonyl groups; hydroxyls; nitro, amino, amide, and azo groups; sulfate, sulfonate, sulfono, sulfhydryl, sulfonyl, sulfoxido, phosphate, phosphono, phosphoryl groups, and halide substituents. In an additional embodiment, a "modification" can be an addition or a deletion of one or more atoms of the atomic framework, for example, substitution of an ethyl by a propyl; substitution of a phenyl by a larger or smaller aromatic group. Alternatively, in a cyclic or bicyclic structure, hetero atoms such as N, S, or O can be substituted into the structure instead of a carbon atom. A modification can be a "prodrug" derivative, which has significantly reduced pharmacological activity, and contains an additional moiety which is susceptible to removal in vivo yielding the parent molecule as the pharmacologically active species.

The term "analog" is a compound that is similar or comparable, but not identical, to another compound having similar structural characteristics, but that is not identical in structure. As used herein, an analog is a chemical compound, for example, a peptide or a protein used as the target for drug discovery and thus included in HTS assays, that is structurally similar to another but differs slightly in composition (for example, a replacement of one atom by an atom of a different element, or a change in presence of a particular functional atom or group of atoms between the original compound and the analog).

The term "derivative" as used herein refers to a compound formed from the original structure either directly, by chemical reaction of the original structure, or by a "modification" which is a partial substitution of the original structure, or by design and de novo synthesis. Derivatives may be synthetic, or may be metabolic products of a cell or an in vitro enzymatic reaction. In general, a set of derivatives is synthesized from a lead compound obtained by HTS, in order to obtain compounds with improved properties of inhibition of the target used in the high throughput screen, the inhibition having been demonstrated by the lead compound. Additional derivatives can be synthesized in order to optimize other pharmacological properties of a lead compound, such as absorption, distribution, metabolism, and excretion or transformation into another compound.

A combination of at least two nuclease inhibitors is referred to herein as a "nuclease inhibitor cocktail." The nuclease inhibitors include anti-nuclease antibodies and non-antibody nuclease inhibitors ("other nuclease inhibitors").

"In vitro translation" is a process of protein synthesis outside the living cell using cell-free extract and mRNA transcript as genetic material for translation. Examples of in vitro translation reactions include IVT Retic Lysate™ or IVT Wheat Germ™ (Ambion). Of course, those of ordinary skill in the art will understand how to perform in vitro translation reactions with other than the examples given.

"In vitro coupled transcription/translation" is a process of protein synthesis in a cell-free lysate where the starting genetic material is DNA and both transcription and translation processes are proceeding simultaneously. An example of in vitro coupled transcription/translation is the PROTEINscript-PRO™ system (Ambion). One of ordinary skill in the art will be able to perform in vitro coupled transcription/translation reactions with other than the example given.

An "in vitro transcription reaction" is the production of RNA from a DNA template under control of specific RNA polymerase(s) in the presence of rNTPs in the transcription buffer optimized for in vitro transcription. Examples of in vitro transcription reaction are MAXIscript™, MEGAscript™, and mMESSAGE mMACHINE™ (Ambion). One of ordinary skill in the art will understand how to perform in vitro transcription reactions with other than the examples given.

In standard in vitro translation reactions, purified RNA is used as a template for translation. "Linked" and "coupled" systems, on the other hand, use DNA as a template. RNA is transcribed from the DNA and subsequently translated without any purification. Such systems typically combine a prokaryotic phage RNA polymerase and promoter (T7, T3, or SP6) with eukaryotic or prokaryotic extracts to synthesize proteins from exogenous DNA templates. DNA templates for transcription:translation reactions may be cloned into plasmid vectors or generated by PCR. The "linked" system is a two-step reaction, based on transcription with a bacteriophage polymerase followed by translation in the rabbit reticulocyte lysate or wheat germ lysate. Because the transcription and translation reactions are separate, each can be optimized to ensure that both are functioning at their full potential.

Unlike eukaryotic systems where transcription and translation occur sequentially, in E. coli, transcription and translation occur simultaneously within the cell. In vitro E. coli translation systems are thus performed the same way, coupled, in the same tube under the same reaction conditions. During transcription, the 5' end of the RNA becomes available for ribosomal binding and undergoes translation while its 3' end is still being transcribed. This early binding of ribosomes to the RNA maintains transcript stability and promotes efficient translation. This bacterial translation system gives efficient expression of either prokaryotic or eukaryotic gene products in a short amount of time. Use of E.coli extract also eliminates cross-reactivity or other problems associated with endogenous proteins in eukaryotic lysates.

Nucleases

Nucleases are capable of degrading ribonucleic acid (RNA) and/or deoxyribonucleic acid (DNA). The nucleases may specifically degrade RNA or DNA, or may be non-specific nucleases, such as S1 nuclease and micrococcal nuclease, and degrade both RNA and DNA. The nucleases encompassed by the present invention include exonucleases and endonucleases.

Ribonucleases (RNases)

Non-limiting examples of ribonucleases that are inhibited using the present invention include, but are not limited to, RNase A, RNase B, RNase C, RNase 1, RNase T1, micrococcal nuclease, S1 nuclease, or DNase 1. Additional eukaryotic ribonucleases may be inactivated, such as a member of a mammalian ribonuclease A super family (i.e., ribonucleases 1-8), a member of an RNase H family, RNase L, eosinophil RNase, messenger RNA ribonucleases (5'-3' Exoribonucleases, 3'-5' Exoribonucleases), decapping enzymes and deadenylases. Additional ribonucleases that may be inhibited and/or inactivated by the methods and compositions of the present invention include E. coli endoribonucleases (RNase P, RNase III, RNase E, RNase I, RNase HI, RNase HII, RNase M, RNase R, RNase IV, F; RNase P2,O, PIV, PC, RNase N), E. coli exoribonucleases (RNase II, PNPase, RNase D, RNase BN, RNase T, RNase PH, OligoRNase, RNase R), RNase Sa, RNase F1, RNase U2, RNase Ms, and RNase St. Both endonucleases and exonucleases can be inhibited by the nuclease inhibitor cocktail of the present invention. One of skill in the art can readily employ the methods and compositions of the present invention to inhibit and/or inactivate other RNases known in the art beyond those specifically named herein.

Deoxyribonucleases (DNases)

Non-limiting examples of deoxyribonucleases that can be inhibited and/or inactivated using the present invention include, but are not limited to, DNase 1, S1 nuclease, and micrococcal nuclease. The nuclease inhibitor cocktail of the present invention can be used to inhibit both endonucleases and exonucleases. One of skill in the art can readily employ the methods and compositions of the present invention to inhibit and/or inactivate other DNases known in the art beyond those specifically named herein.

Compositions

The compositions to which the present methods may be applied in order to inhibit and/or inactivate nucleases will be generally in a liquid form, although a solid composition, such as a matrix comprising immobilized nuclease inhibitor, is also contemplated within the scope of the present invention. If liquid, the composition may be, for example, a reagent used in molecular biology. Representative reagents that may be employed in the present invention include, but are not limited to, water, tris-ethylenediamine tetraacetic acid buffer (TE buffer), sodium chloride/sodium citrate buffer (SSC), 3-(N-morpholinol) propanesulfonic acid (MOPS), Tris buffer, ethylenediamine tetraacetic acid, nucleic acid hybridization buffer, sodium acetate buffer, DNase I digestion buffer, transcription buffer, reverse transcription buffer, cell free extract for in vitro translation, in situ hybridization buffer, and nucleic acid storage buffer/solution. One of skill in the art will understand that the methods of the present invention can be employed with compositions in addition to those named above.

Anti-Nuclease Antibodies

The anti-nuclease antibodies employed in the present invention may be anti-ribonuclease antibodies or anti-deoxyribonuclease antibodies. The anti-ribonuclease antibodies may be antibodies that inhibit one or more of the following ribonucleases: RNase A, RNase B, RNase C, RNase 1, RNase T1, micrococcal nuclease, S1 nuclease, a member of the mammalian ribonuclease 1 family, a member of the ribonuclease 2 family, mammalian angiogenins, a member of the RNase H family, RNase L, eosinophil RNase, messenger RNA ribonucleases (5'-3' Exoribonucleases, 3'-5' Exoribonucleases), decapping enzymes, deadenylases, E. coli endoribonucleases (RNase P, RNase III, RNase E, RNase I, RNase HI, RNase HII, RNase M, RNase R, RNase IV, F; RNase P2,O, PIV, PC, RNase N), E. coli exoribonucleases (RNase II, PNPase, RNase D, RNase BN, RNase T, RNase PH, OligoRNase, RNase R), RNase Sa, RNase F1, RNase U2, RNase Ms, and RNase St. Antibodies to additional RNases not specifically disclosed herein can also be employed in the present invention to inhibit and/or inactivate those RNases, or other RNases.

The anti-nuclease antibodies employed in the present invention may also be anti-deoxyribonuclease antibodies that inhibit one or more of the following deoxyribonucleases: DNase 1, S1 nuclease, and micrococcal nuclease. DNases will often require the presence of cations, such as $Mg^{+2}$ or $Ca^{+2}$. Antibodies to additional DNases not specifically disclosed herein can also be employed in the present invention to inhibit and/or inactivate those DNases.

The anti-nuclease antibodies may be present in a concentration of up to 100 mg/ml, more preferably in a concentration of up to 50 mg/ml, and even more preferably in a concentration of up to 20 mg/ml. In some embodiments the anti-nuclease antibodies will be present in a concentration of 10 to 0.5 mg/ml. In the most preferred embodiment, the concentration of the anti-nuclease antibodies will be 3 to 4 mg/ml.

For some embodiments of the invention, it will be desired to produce antibodies that bind to a particular nuclease. Means for preparing and characterizing antibodies are well known in the art.

Methods for generating polyclonal antibodies are well known in the art, and a specific method for doing so to generate antibodies to RNase is described in the examples below. Generally, a polyclonal antibody is prepared by immunizing an animal with an antigenic composition and collecting antisera from that immunized animal. A wide range of animal species can be used for the production of antisera. Typically the animal used for production of antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimido-benzoyl-N-hydroxysuccinimide ester, carbodiimide and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, may also be given. The process of boosting and titering is repeated until a suitable titer is achieved. When a desired level of immunogenicity is obtained, the immunized animal can be bled and the serum isolated and stored, and/or in some cases the animal can be used to generate monoclonal antibodies (MAbs). For production of rabbit polyclonal antibodies, the animal can be bled through an ear, vein or alternatively by cardiac puncture. The removed blood is allowed to coagulate and then centrifuged to separate serum components from whole cells and blood clots. The serum may be used as is for various applications or the desired antibody fraction may be purified by well-known methods, such as affinity chromatography using another antibody or a peptide bound to a solid matrix.

Monoclonal antibodies (MAbs) may be readily prepared through use of well-known techniques. Typically, this technique involves immunizing a suitable animal with a selected immunogen composition, e.g., a purified or partially purified expressed protein, polypeptide or peptide. The immunizing composition is administered in a manner that effectively stimulates antibody producing cells.

The methods for generating monoclonal antibodies (MAbs) generally begin along the same lines as those for preparing polyclonal antibodies. Rodents such as mice and rats are preferred animals, however, the use of rabbit, sheep or frog cells is also possible. Mice are preferred, with the BALB/c mouse being most preferred as this is most routinely used and generally gives a higher percentage of stable fusions.

The animals are injected with antigen as described above. The antigen may be coupled to carrier molecules such as keyhole limpet hemocyanin if necessary. The antigen would typically be mixed with adjuvant, such as Freund's complete or incomplete adjuvant. Booster injections with the same antigen would occur at approximately two-week intervals.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and have enzyme deficiencies that render them incapable of growing in certain selective media that support the growth of only the desired fused cells (hybridomas).

Any one of a number of myeloma cells may be used, as are known to those of skill in the art. For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus, polyethylene glycol (PEG), such as 37% (v/v) PEG, and other compounds are known in the art. The use of electrically induced fusion methods is also appropriate.

Fusion procedures usually produce viable hybrids at low frequencies, about $1 \times 10^{-6}$ to $1 \times 10^{-8}$. However, this low frequency does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and thus they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which can then be propagated indefinitely to provide MAbs. The cell lines may be exploited for MAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. MAbs produced by either means may be further purified, if desired, using filtration, centrifugation and various chromatographic methods such as HPLC or affinity chromatography.

Large amounts of the monoclonal antibodies of the present invention may also be obtained by multiplying hybridoma cells in vivo. Cell clones are injected into mammals that are histocompatible with the parent cells, e.g., syngeneic mice, to cause growth of antibody-producing tumors. Optionally, the animals are primed with a hydrocarbon, especially oils such as pristane (tetramethylpentadecane) prior to injection.

Non-Antibody Nuclease Inhibitors

The invention also envisions the use of non-antibody compounds that function to inhibit nucleases. Non-antibody nuclease inhibitors that can be used with the present invention include, but are not limited to, small molecules, oligonucleotides, proteinaceous compounds, and affinity resins.

"Small molecules" include, e.g., organic compounds, inorganic compounds, salts, and/or chaotropes. The small molecules of the present invention can include a molecular weight of less than about 5000. In particular embodiments of this invention, the molecular weight of the small molecule can be about 4000, 3000, 2000, 1000, 900, 800, 700, 600, 500, 400, 300, 200, 100, 50, 25, 15, 10, or 5.

An "organic molecule" can include, e.g., a "small molecule" that comprises the element carbon. Organic molecules include hydrophilic and hydrophobic compounds. Other examples are nitrogenous bases, chelators, reductants, and detergents. Non-limiting examples of organic compounds that can be used with the present invention include oligovinylsulfonic acid (OVA), aurintricarboxylic acid (ATA), aflatoxin, 2-nitro-5-thiocyanobenzoic acid, iodoacetate, N-bromosuccinimide, p-chloromercuribenzoate, diethyl pyrocarbonate, ethanol, formamide, guanidinium thiocyanate (GdnSCN), dinitrofluorobenzene, decanavanate, polyvinylsufonic acid, hydrobenzoinphosphate, phenylphosphate, putrescine, haloacetate, dinitrofluorobenzene, phenylglyoxal, bromopyruvic, hydroxylamine-oxygen-cupric ion, a vanadyl complex, 8-amino-5-(4'-hydroxy-biphenyl-4-ylazo)-naphthalene-2-sulfonate, 6-hydroxy-5-(2-hydroxy-3,5-dinitro-phenylazo)-naphthalene-2-sulfonate, 3,3'-dimethylbiphenyl-4,4'-bis(2-amino-naphthylazo-6-sulfonate), 4,4'-dicarboxy-3,3'-bis(naphthylamido)-diphenylmethanone, 3,3'-dicarboxy-4,4'-bis(4-biphenylamido) diphenylmethane, or 3,3'-dicarboxy-4,4'-bis (3-nitrophenylamido)diphenylmethane.

A "nitrogenous base" can include, e.g., a nitrogen-containing, heterocyclic organic molecule. Non-limiting examples include purines, pyrimidines, and related derivatives. In particular embodiments, the nitrogenous base can be coupled to a sugar moiety to form nucleosides or nucleotides. Other non-limiting examples include cytidine-N3-oxide 2'-phosphate, 2'CMP, ppAp, Ap3A, Ap4A, Ap5A, ATP, 5'AMP, 5'ADP, 3'UMP, 2'UMP, 2'CMP, pAp (5'P-A-3'P), dUppAp, dUppA2'p, pdUppAp, pTp, pTppAp, TpdA, TppdA, 4-thiouridine 3'p, 5-nitro-uracil, 5-aminoethyl-uracil or (Bromoacetamido)nucleoside.

A "reductant" can include, e.g., a compound that it capable of transforming an oxidized molecule or moiety to a reduced state. Non-limiting examples include Cysteine, DTT, 2-ME, TCEP, (+/−)-trans-1,2-bis(2-mercaptoacetamido)cyclohexane (BMC), and Cys-Glu-Cys tripeptide.

A "chelator" can include, e.g., a chemical entity capable of tightly binding or caging free metallic ions, sometimes with increased specificity. Non-limiting examples include EDTA, EGTA, BAPTA, Citrate, NTP, and dNTP.

A "detergent" can include, e.g., an ionic or non-ionic surfactant. Non-limiting examples include SDS, deoxycholate, and N-laurylsarcosine, NP 40, Tween 20, and Triton X-100. These detergents can exhibit a synergistic effect with anti-nuclease antibodies to enhance the activity of the anti-nuclease antibodies.

An "inorganic molecule" can include, e.g., a "small molecule" that comprises elements other than carbon such as metallic ions or complexes such as $Mg^{+2}$, $Mn^{+2}$, $Zn^{+2}$, $Fe^{+2}$, $Ca^{+2}$ or $Cu^{+2}$.

A "salt" can be, e.g., a monovalent or multivalent salt. Non-limiting examples include $(NH_4)_2SO_4$, NaCl, KCl, and NaCitrate.

A "chaotrope" can include, e.g., a chemical that can disrupt the structure of water and/or promote the solubility of nonpolar substances in polar solvents such as water. Such behavior by chaotropes often results in the unfolding and inactivation of proteins. Non-limiting examples include $SCN^-$, $Li^+$, $ClO_4^-$ and guanidinium.

"Proteinaceous compounds" include compounds that comprise at least one amino acid or that contain amino acid chemistry. Non-limiting examples include RNase inhibitor proteins (RIPs) (e.g., RIP obtained from human, chimpanzee, rat, mouse, pig, or yeast and including recombinant RIP and derivatives therein), proteases (e.g., proteinase K, subtilisin, other alkaline proteases, acid proteases (e.g., pepsin), and pancreatic proteases (e.g., elastase, trypsin, and chymotrypsin)), actin (e.g., DNase inhibitors), RraA (an RNase E inhibitor (Lee et al., 2003), and tyrosine-Glutamate copolymer.

Non-limiting examples of oligonucleotides include DNA, RNA, thiol-containing or otherwise blocked RNA (i.e., non-cleavable), aptamers, and DNP-Poly(A).

An "affinity resin" can include, e.g., a charged substance that can bind proteins such as RNases or DNases as a way to prevent their diffusion through solution and to remove the proteins from solution. Non-limiting examples include SP resin.

The compounds disclosed in Tables 1 and 2 include additional non-limiting compounds that can be used with the compositions, methods, and kits of the present invention.

TABLE 1

Lead 1 Analog List

| Library | Structure | # | $K_I$ | MW pH7 | LogP |
|---|---|---|---|---|---|
| NCI | | 65828 | 81 | 418 | 3.47 |
| NCI | | 65845 | 3 | 852 | 2.70 |
| Rare Aldrich & NCI | 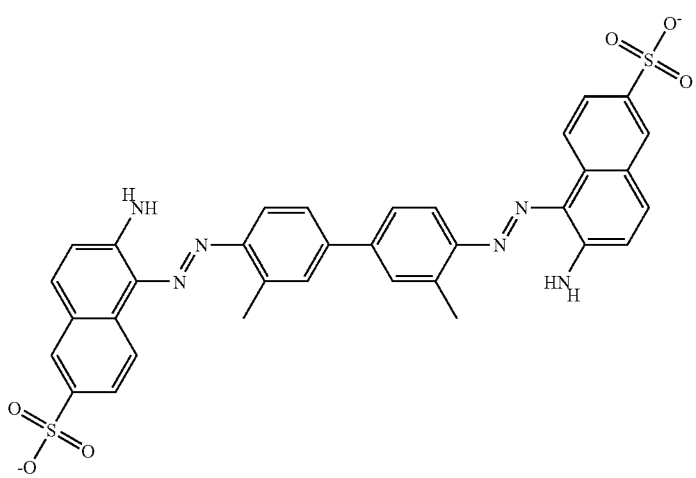 | Benzo-purpurin B/ 242027 | 5 | 679 | 5.25 |
| NCI | | 65841 | 5 | 839 | 2.28 |

TABLE 1-continued

Lead 1 Analog List

| Library | Structure | # | $K_I$ | MW pH7 | LogP |
|---|---|---|---|---|---|
| NCI | | 79596 | 5 | 850 | 4.28 |
| NCI | | 9617/ Chicago Sky Blue 6B | 5 | 901 | 1.26 |
| NCI Reserve | 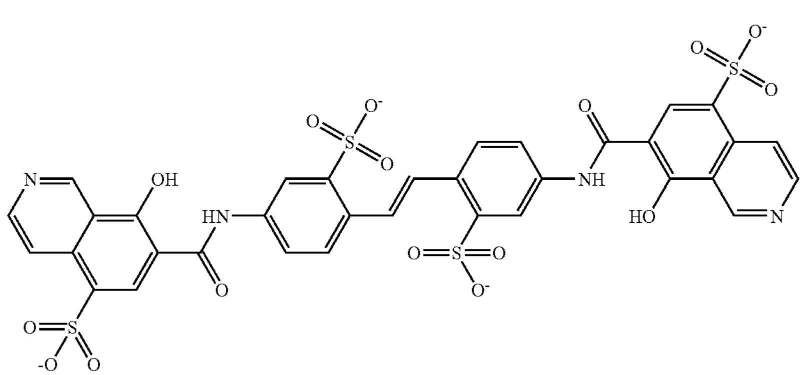 | 665534-P | 5 | 869 | −0.61 |

TABLE 1-continued

Lead 1 Analog List

| Library | Structure | # | $K_I$ | MW pH7 | LogP |
|---|---|---|---|---|---|
| NCI | 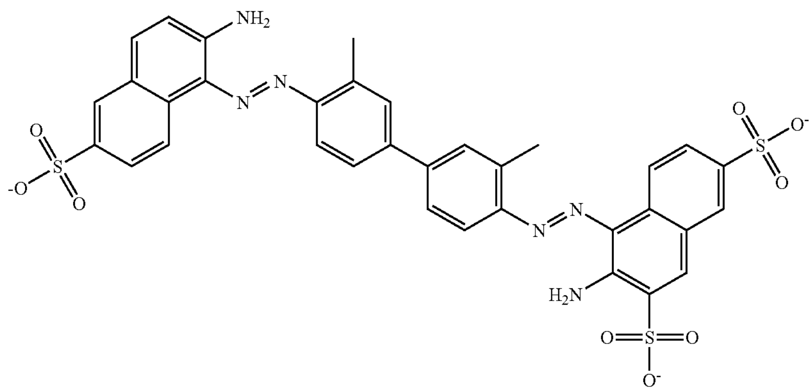 | 16224/ direct red 34 | 5.5 | 761 | 3.93 |
| Sigma-Aldrich | 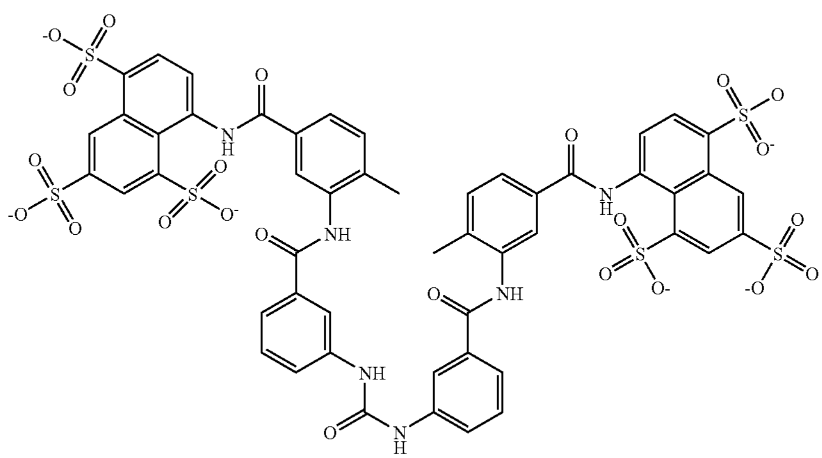 | suramin | 10 | 1291 | −6.26 |
| Rare Aldrich & NCI | 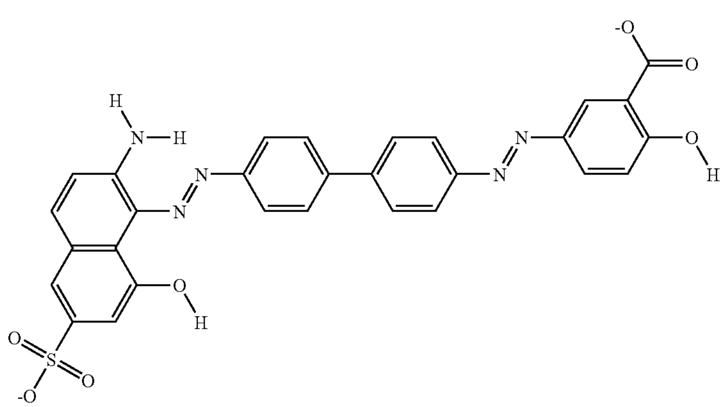 | direct red 1/ N-73358 | 14 | 582 | 4.02 |

TABLE 1-continued

Lead 1 Analog List

| Library | Structure | # | $K_I$ | MW pH7 | LogP |
|---|---|---|---|---|---|
| NCI | | 7815 | 14 | 758 | 3.93 |
| NCI | | 45618 | 15 | 651 | 4.42 |
| NCI | | 47740 | 15 | 798 | 3.39 |

TABLE 1-continued

Lead 1 Analog List

| Library | Structure | # | $K_I$ | MW pH7 | LogP |
|---|---|---|---|---|---|
| New | 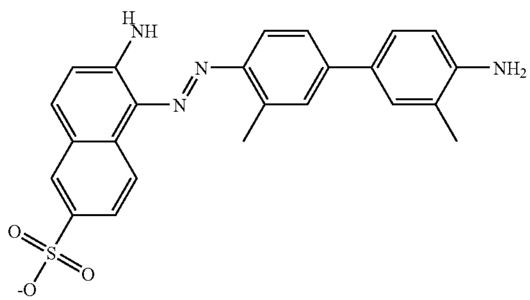 | prBZBP | 20 | 445 | 3.80 |
| NCI | | 65568 | 23 | 839 | 3.45 |
| NCI | | 79741 | 23 | 931 | 3.39 |
| NCI | | 65820 | 25 | 433 | 2.38 |

TABLE 1-continued

Lead 1 Analog List

| Library | Structure | # | $K_I$ | MW pH7 | LogP |
|---|---|---|---|---|---|
| NCI | | 65553 | 29 | 541 | 3.23 |
| NCI | | 58047 | 36 | 511 | 3.10 |
| NCI | | 65847 | 38 | 851 | 3.98 |
| Sigma-Aldrich | 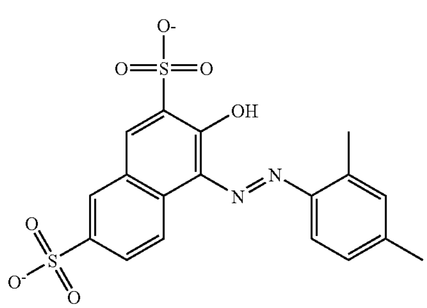 | xylidene ponceau 2R | 49 | 434 | 2.36 |

TABLE 1-continued
Lead 1 Analog List
| Library | Structure | # | $K_I$ | MW pH7 | LogP |
|---|---|---|---|---|---|
| Sigma-Aldrich | 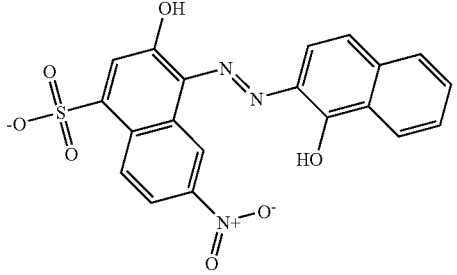 | erio-chrome black T | 50 | 438 | 3.54 |
| Sigma-Aldrich | 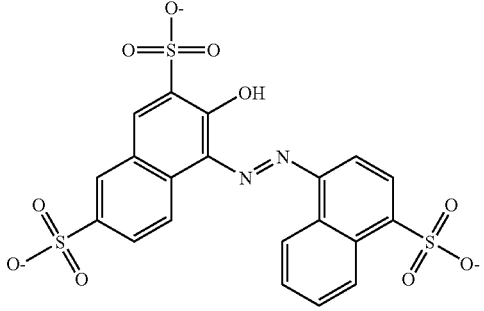 | Amaranth | 60 | 536 | 1.32 |
| Sigma-Aldrich | 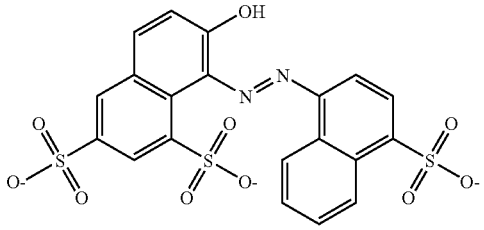 | new coccine | 69 | 536 | 1.32 |
| Sigma-Aldrich | 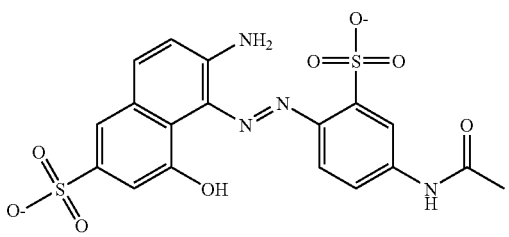 | acid red 37 | 70 | 478 | 0.13 |
| Sigma-Aldrich | 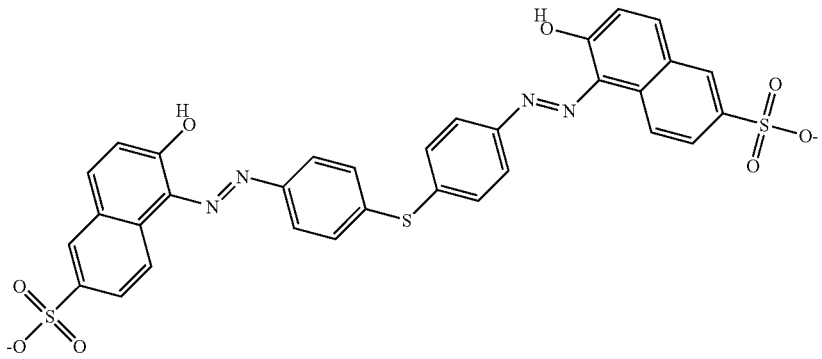 | acid violet 7 | 71 | 441 | 1.68 |

TABLE 1-continued

Lead 1 Analog List

| Library | Structure | # | $K_I$ | MW pH7 | LogP |
|---|---|---|---|---|---|
| NCI | | 45608 | 75 | 576 | 3.35 |
| NCI | | 75661 | 76 | 823 | 7.03 |
| NCI | | 73416 | 77 | 685 | 6.15 |
| NCI | | 724225 | 81 | | |

TABLE 1-continued

Lead 1 Analog List

| Library | Structure | # | $K_I$ | MW pH7 | LogP |
|---|---|---|---|---|---|
| Sigma-Aldrich | | Orange G | 83 | 406 | 1.53 |
| NCI | | 47755 | 84 | 791 | 4.65 |
| Sigma-Aldrich | | sunset yellow | 85 | 406 | 1.53 |
| NCI | | 47735 | 85 | 557 | 4.13 |
| NCI | | 37176 | 104 | 358 | 1.80 |

TABLE 1-continued
Lead 1 Analog List
| Library | Structure | # | K_I | MW pH7 | LogP |
|---|---|---|---|---|---|
| Rare Aldrich | 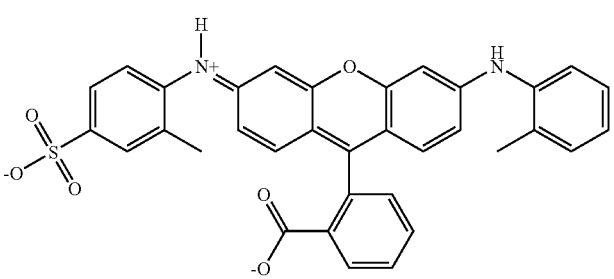 | violamine R | 107 | 590 | 6.19 |
| NCI | 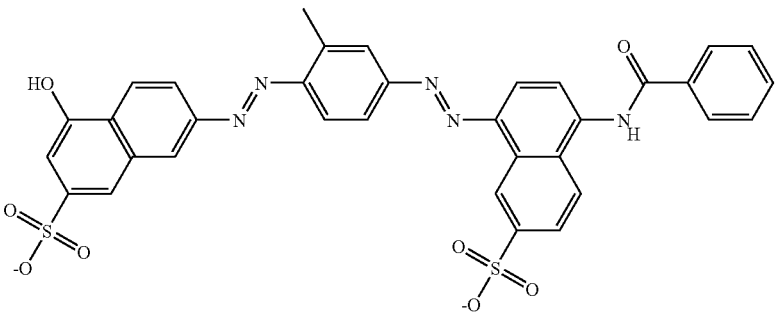 | 65844 | 108 | 694 | 5.34 |
| Rare Aldrich | 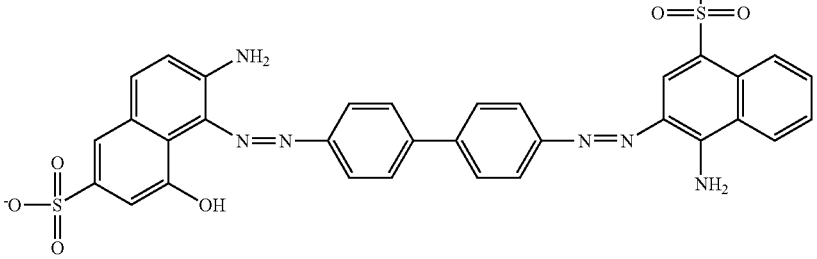 | direct red 13 | 112 | 667 | 4.03 |
| NCI | 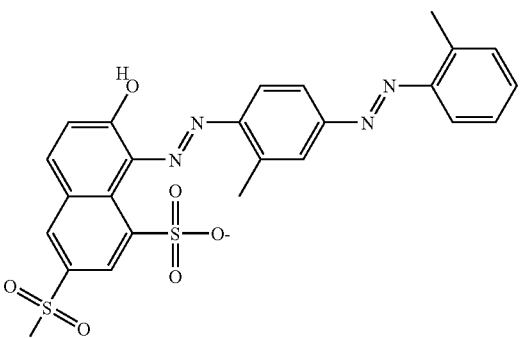 | 45601 | 122 | 589 | 3.93 |

TABLE 1-continued
Lead 1 Analog List
| Library | Structure | # | $K_I$ | MW pH7 | LogP |
|---|---|---|---|---|---|
| NCI | 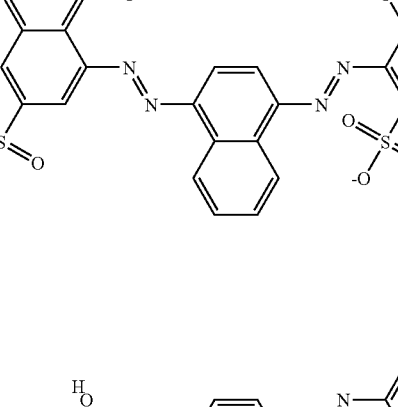 | 75916 | 125 | 797 | 5.23 |
| NCI | 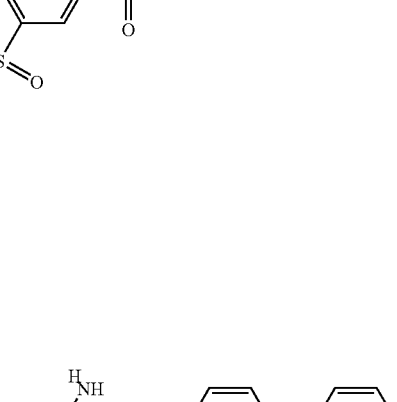 | 65546 | 129 | 590 | 1.78 |
| NCI | 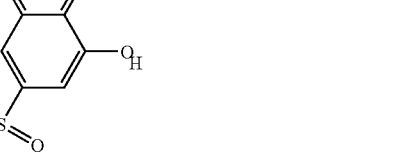 | 65855 | 129 | 911 | 3.86 |

TABLE 1-continued

Lead 1 Analog List

| Library | Structure | # | $K_I$ | MW pH7 | LogP |
|---------|-----------|---|-------|--------|------|
| NCI | | 75963 | 129 | 655 | 7.25 |
| NCI | | 45612 | 158 | 582 | 4.99 |
| NCI | | 8674 | 158 | 706 | 3.63 |

TABLE 1-continued

Lead 1 Analog List

| Library | Structure | # | $K_I$ | MW pH7 | LogP |
|---|---|---|---|---|---|
| NCI | | 75778 | 171 | 683 | 3.64 |
| NCI | | 34933 | 172 | 835 | 2.51 |
| NIC | 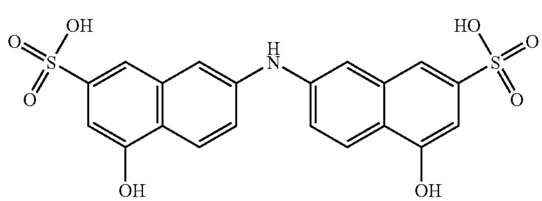 | 1698 | 172 | 462 | 3.03 |
| NCI | | 7814 | 175 | 341 | 3.27 |

TABLE 1-continued

Lead 1 Analog List

| Library | Structure | # | $K_I$ | MW pH7 | LogP |
|---|---|---|---|---|---|
| NCI | | 45550 | 183 | 466 | 0.67 |
| NCI | | 45569 | 194 | 354 | 3.26 |
| NCI | | 77521 | 195 | 935 | 5.13 |
| Sigma-Aldrich | 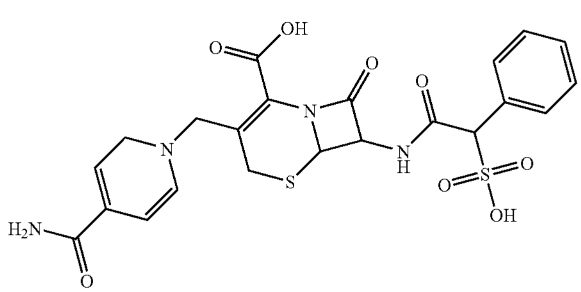 | cefsulodin | 201 | 535 | −1.75 |

TABLE 1-continued

Lead 1 Analog List

| Library | Structure | # | $K_I$ | MW pH7 | LogP |
|---|---|---|---|---|---|
| NCI | | 174066 | 234 | 685 | 0.07 |
| NCI | | 12455 | 239 | 450 | 0.88 |
| NCI | | 45541 | 244 | 451 | 1.49 |

TABLE 1-continued

Lead 1 Analog List

| Library | Structure | # | $K_I$ | MW pH7 | LogP |
|---|---|---|---|---|---|
| NCI | | 79744 | 244 | 911 | 3.86 |
| NCI | | 42067 | 245 | 635 | −6.06 |
| NCI | | 45571 | 300 | 383 | 1.84 |
| NCI | | 45538 | 305 | 372 | 2.81 |

TABLE 1-continued
Lead 1 Analog List
| Library | Structure | # | $K_I$ | MW pH7 | LogP |
|---|---|---|---|---|---|
| NCI | 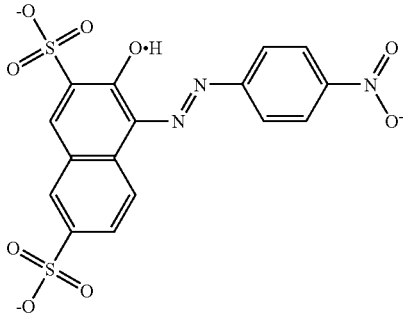 | 45540 | 307 | 451 | 1.49 |
| NCI | 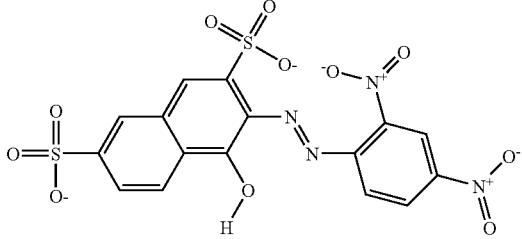 | 9360 | 307 | 496 | 1.45 |
| NCI | 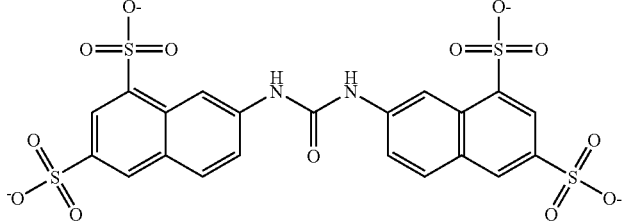 | 12857 | 336 | 629 | −0.52 |
| NCI | 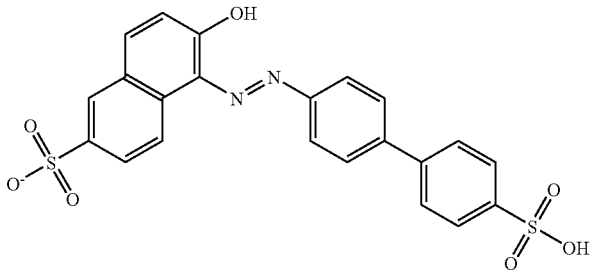 | D726712 | ~350 | 469 | 5.07 |
| NCI | 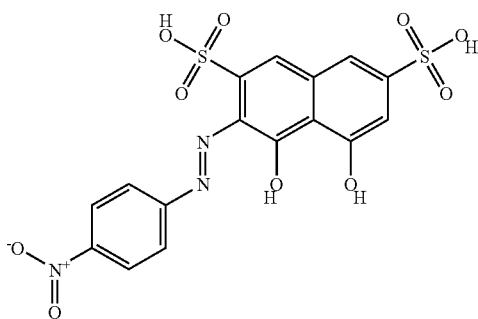 | 45542 | 426 | 469 | 1.10 |

TABLE 1-continued

Lead 1 Analog List

| Library | Structure | # | $K_I$ | MW pH7 | LogP |
|---|---|---|---|---|---|
| NCI | | 7557 | 500 | 301 | −0.47 |
| Rare Aldrich | 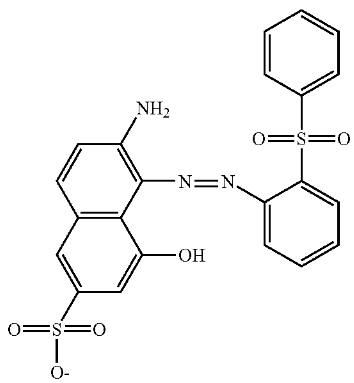 | S321443 | >500 | 483 | 3.64 |
| NCI | | 224131 | >500 | 251 | −4.97 |
| NCI | | 45557 | >500 | 341 | 3.27 |
| NCI | | 1741 | ~600 | 477 | 2.61 |

TABLE 1-continued

Lead 1 Analog List

| Library | Structure | # | $K_I$ | MW pH7 | LogP |
|---|---|---|---|---|---|
| NCI | | 1743 | inactive at 75 uM | 358 | 1.80 |
| NCI | | 16163 | inactive at 75 uM | 297 | 0.53 |
| NCI | | 16169 | inactive at 75 uM | 423 | 1.76 |
| NCI | | 88947 | inactive at 75 uM | 423 | 2.44 |
| NCI | | 17061 | 900 | 307 | 3.46 |

TABLE 1-continued

Lead 1 Analog List

| Library | Structure | # | $K_I$ | MW pH7 | LogP |
|---|---|---|---|---|---|
| NCI | 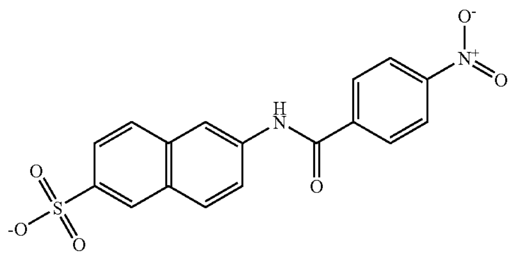 | 37169 | 950 | 371 | 2.33 |
| ACD | 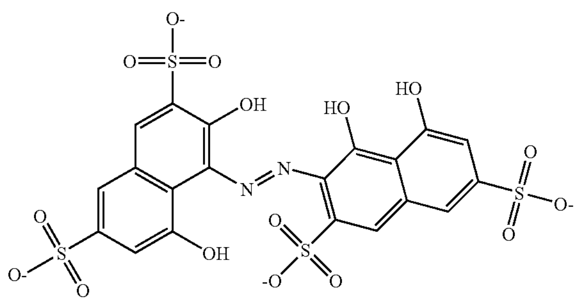 | beryllon II | >1000 | 663 | −1.17 |

TABLE 2

Lead 2 Analogue List.

| Library[α] | structure | name | $K_i$ (μM) | MW |
|---|---|---|---|---|
| CB | | 181431 compound 2 | 41 | 609 |
| CB | | 473872 compound 2a | 20 | 647 |

TABLE 2-continued

Lead 2 Analogue List.

| Library[α] | structure | name | $K_i$ (μM) | MW |
|---|---|---|---|---|
| New | | JLJ-1 | 21 | 615 |
| New | | JLJ-2 | 18 | 466 |
| New | | JLJ-3 | 20 | 600 |
| CB | 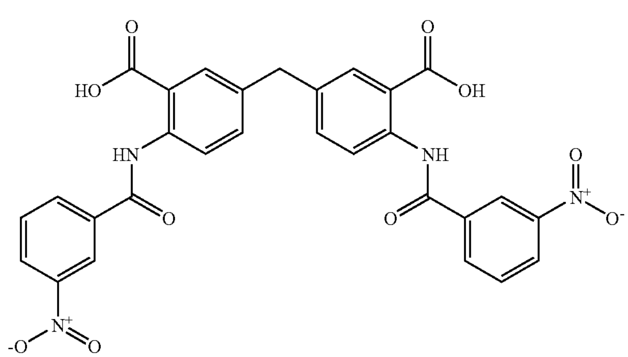 | 467929 compound 2b | 24 | 584 |

TABLE 2-continued

Lead 2 Analogue List.

| Library[α] | structure | name | $K_i$ (μM) | MW |
|---|---|---|---|---|
| CB | | 534510 | 75 | 611 |
| CB | | 540408 | 79 | 695 |
| CB | | 180582 | 79 | 595 |
| CB | | 180553 | 79 | 386 |
| CB | | 186847 | 84 | 494 |

TABLE 2-continued
Lead 2 Analogue List.
| Library | structure | name | $K_i$ (μM) | MW |
|---|---|---|---|---|
| CB | 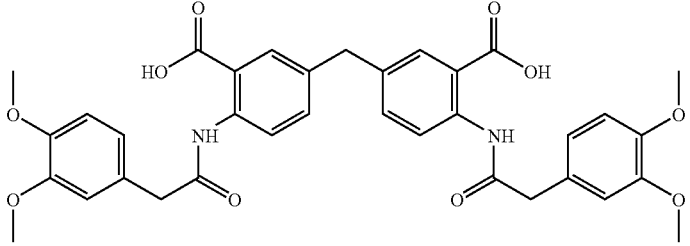 | 477474 | 120 | 643 |
| CB | 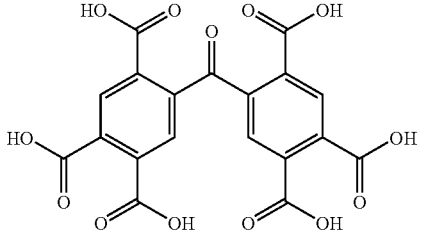 | 152591 | 150 | 446 |
| NCI | 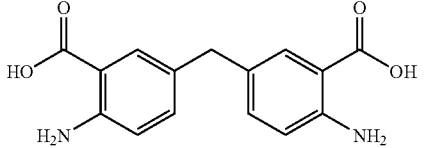 | 37136 | >500 | 286 |
| NCI | 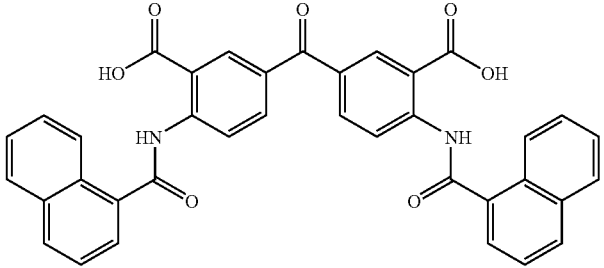 | 202516 | >500 | 609 |
| CB | 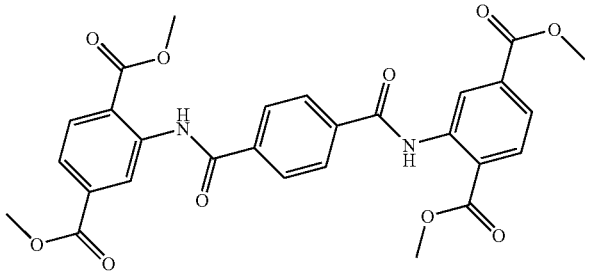 | 039263 | >500 | 549 |

TABLE 2-continued

Lead 2 Analogue List.

| Library[a] | structure | name | K$_i$ (μM) | MW |
|---|---|---|---|---|
| CB | | 181145 | >500 | 601 |
| CB | | 181429 | >500 | 553 |
| CB | | 205125 | >500 | 491 |
| CB | | 224197 | >500 | 486 |

[a]CB = ChemBridge Corporation;
NCI = National Cancer Institute;
new = synthesized in Shapiro lab (2003)

Derivatives of the compounds in tables 1 and 2 are also contemplated as being useful with the present invention. Chemical modifications may also be made to these compounds. Chemical modifications may be advantageous, for example, to increase or decrease the inhibitory efficacy of these compounds. A person of ordinary skill in the art would be able to recognize and identify acceptable known and unknown derivatives and/or chemical modifications that can be made to these compounds without undue experimentation. Non-limiting examples of such derivatives and chemical modifications include those described in PCT application entitled "Small-Molecule Inhibitors of Angiogenin and In Vivo Anti-Tumor Compounds" by Shapiro et al., filed on Feb. 25, 2004, which claims priority to U.S. provisional application Ser. No. 60/449,912, filed Feb. 25, 2003. The text of these applications are incorporated by reference.

Other non-antibody nuclease inhibitors that can be used in the methods and compositions of the present invention are discussed throughout the specification, e.g., in the summary of the invention, the examples, and the claims. Using the information provided in this specification, one of skill in the art will be able to identify additional compounds that may be employed in practicing the present invention.

Proteinaceous Compounds and Compositions

In certain embodiments, the present invention concerns the use of compositions or methods comprising at least one proteinaceous molecule. The proteinaceous molecule can be, for example, a nuclease inhibitor.

As used herein, a "proteinaceous molecule," "proteinaceous composition," "proteinaceous compound," "proteinaceous chain," or "proteinaceous material" generally refers, but is not limited to, a protein of greater than about 200 amino acids or the full length endogenous sequence translated from a gene; a polypeptide of greater than about 100 amino acids; and/or a peptide of from about 3 to about 100 amino acids. All the "proteinaceous" terms described above may be used interchangeably herein.

In certain embodiments the size of the at least one proteinaceous molecule may 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1100, 1200, 1300, 1400, 1500, 1750, 2000, 2250, 2500 or greater contiguous amino molecule residues, and any range derivable therein.

As used herein, an "amino molecule" refers to any amino acid, amino acid derivative or amino acid mimic as would be known to one of ordinary skill in the art. In certain embodiments, the residues of the proteinaceous molecule are sequential, without any non-amino molecule interrupting the sequence of amino molecule residues. In other embodiments, the sequence may comprise one or more non-amino molecule moieties. In particular embodiments, the sequence of residues of the proteinaceous molecule may be interrupted by one or more non-amino molecule moieties.

Protein Synthesis

The proteinaceous molecules that can be used in the present invention, e.g., nuclease inhibitors, can be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), Houghten et al. (1985). In some embodiments, peptide synthesis is contemplated by using automated peptide synthesis machines, such as those available from Applied Biosystems (Foster City, Calif.).

Longer peptides or polypeptides also may be prepared by recombinant means, e.g., by the expression of a nucleic acid sequence encoding a peptide or polypeptide, e.g. nuclease inhibitor, in an in vitro translation system or in a living cell. In certain embodiments of this invention, a nucleic acid encoding a nuclease inhibitor is comprised in, for example, a vector in a recombinant cell. The nucleic acid may be expressed to produce the nuclease inhibitor. The nuclease inhibitor may be secreted from the cell, or comprised as part of or within the cell.

The term "vector" as used herein relates to naturally occurring or synthetically generated constructs for uptake, proliferation, expression or transmission of nucleic acids in a cell, e.g., plasmids, phagemids, cosmids, artificial chromosomes/mini-chromosomes, bacteriophages, viruses or retro viruses. Methods used to construct vectors are well known to a person skilled in the art and described in various publications. In particular techniques for constructing suitable vectors, including a description of the functional and regulatory components such as promoters, enhancers, termination and polyadenylation signals, selection markers, origins of replication, and splicing signals, are reviewed in considerable details in Sambrook et al. (2001) and references cited therein. The eukaryotic expression vectors will typically contain also prokaryotic sequences that facilitate the propagation of the vector in bacteria such as an origin of replication and antibiotic resistance genes for selection in bacteria. A variety of eukaryotic expression vectors, containing a cloning site into which a polynucleotide can be operatively linked, are well known in the art and some are commercially available from companies such as Stratagene, La Jolla, Calif.; Invitrogen, Carlsbad, Calif.; Promega, Madison, Wis. or BD Biosciences Clontech, Palo Alto, Calif.

Protein Purification

It may be desirable to purify the proteinaceous compounds of the present invention. Protein purification techniques are well known to those of skill in the art. Examples of such techniques include Polyacrylamide Gel Electrophoresis, High Performance Liquid Chromatography (HPLC), Gel chromatography or Molecular Sieve Chromatography and Affinity Chromatography.

The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Anti-Nuclease Cocktail

As indicated above, the nuclease inhibitor cocktail of the present invention comprises a combination of at least two nuclease inhibitors. Preferably, the nuclease inhibitor cocktail of the present invention remains active over a broad range of conditions. In a preferred embodiment, the nuclease inhibitor cocktail is active in the presence or absence of DTT. In the most preferred embodiment, DTT can be added up to 200 mM without affecting the activity of anti-nuclease antibodies in the cocktail. A preferred embodiment can be used in a broad functional temperature range, including from 4° C. to 65° C., and at a pH of from 5.5 to 8.5. A preferred embodiment will remain effective at inhibiting nucleases in the presence of guanidinium thiocyanate up to 3 M, and of urea up to 6 M.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Criteria for the Analysis of Nuclease Inactivation

The inventors routinely perform assays on RNA and DNA designed to assess RNase and DNase activity in a sample. Many assays may be used for the detection of nuclease activity, including isotopic and non-isotopic assays. The assays generate similar data with regard to the sensitivity of detection.

In such assays, the inactivation process can be performed, for example, on a mixture of three different ribonucleases: RNase A, RNase 1, and RNase T1. Each ribonuclease may be purified from a different species: human, *E. coli* and fungal, respectively. The three RNases are very different from each other in their origin, substrate specificity, and protein sequence. In this way, the inactivation process can test three completely different but well characterized ribonucleases.

By employing assays, one of skill will be able to determine additional anti-nuclease antibodies, small molecules, proteinaceous compounds and organic compounds that function in the invention. In order to do so, one need only obtain a sample compound or small molecule that is expected to have nuclease inactivating activity and then perform the types of assays performed herein to determine the utility of the sample compound or small molecule in the methods and compositions of the invention.

Isotopic Assay: The isotopic RNase assay uses a radioactive RNA synthesized by in vitro transcription of the RNA substrate. The radioactive RNA is synthesized using a T7 MAXIscript™ transcription kit (Ambion, Inc.). The in vitro transcription reaction mixture may contain, for example, 1.0 µg of linearized DNA template, 2 µl of 10× transcription buffer, 0.02 µl of UTP[α-$^{32}$P] (800 Ci/mmol), 2 µl of each 10 mM ribonucleotide, and 2 µl of the T7 RNA polymerase mix, with a final volume of 20 µl. The reaction is incubated at 37° C. for 30 min. The transcript is purified by phenol: chloroform extraction and used directly for RNase inactivation assay ($2.2 \times 10^5$ counts per minute (approximate specific activity of the probe)/2.3 ng RNA).

Two µl of the RNA probe are incubated with the test sample in a final volume of 10 µl for about 16 hours at 37° C. After incubation, the RNA is fractionated in a denaturing 6 M urea 5% acrylamide gel. The gel is then exposed to x-ray film. Untreated RNA is also fractionated as a control with the test samples for comparative purposes. Test samples containing no detectable RNase activity produce the same single band as the untreated control RNA. RNase activity is indicated by the intensity of the RNA decreasing and by the appearance of smearing below the intact RNA.

Non-Isotopic Assay: The non-isotopic assay can use total RNA isolated from mouse as the substrate for the RNase mixture. The assays are typically performed in a final volume of 10 µl. A quantity of 4 µg of total RNA isolated from mouse liver or brain is dissolved in an aqueous solution, usually water or 1 mM sodium citrate (pH 6.6). The treated ribonuclease sample is added to the total RNA and then incubated at 37° C. for 1 or 16 hours, depending on the sensitivity desired for the assay. After incubation, the RNA is fractionated in a formaldehyde 1% agarose gel. The RNA can be detected by staining with ethidium bromide and then illuminating the gel with ultraviolet light. The RNA fluoresces in the gel. Untreated total RNA can also be fractionated as a control with the test samples for comparative purposes. Test samples containing inactivated RNase produced the same ethidium bromide staining pattern as the untreated RNA control. Intact total RNA has two major bands produced by the 28S and 18S ribosomal RNA. If the intensities of the ribosomal RNAs become diminished compared to the control RNA, then the RNases were not inactivated by the inactivation treatment.

One of skill in the art can employ the same type of methods disclosed above, appropriately adapted, to assay for inactivation of DNase. For example, assays for analysis of the DNA degrading activities of nuclease S1, Micrococcal nuclease, and DNase 1 are disclosed below.

Example 2

Preparation and Isolation of Anti-Nuclease Antibodies

Anti-nuclease antibodies are generated by injecting rabbits with, for example, purified antigens RNase A, RNase T1, RNase 1, Micrococcal nuclease, or S1 nuclease mixed with complete or incomplete Freund's adjuvant. Complete adjuvant (0.5 ml) is mixed with 0.5 ml of antigen solution containing 100 µg of antigen in PBS buffer, and drawn into a syringe with an attached 19-G needle. For the first immunization, 100 µg of the antigen in 0.5 ml of complete adjuvant is injected into each rabbit; 250 µl is injected deeply into each thigh muscle and into each of two sites through the skin on the shoulders. Injections are then repeated biweekly for four weeks using incomplete adjuvant.

Ten days after the final injection, a sample of the rabbit's blood for testing is collected from the marginal ear vein into a sterile glass universal container. The collected blood is allowed to clot by letting it stand at room temperature for 2 hours and then at 4° C. overnight. The serum is separated from the blood by detaching the clot carefully with a spatula from the walls of the container and pouring the liquid into a centrifuge tube. The clot is then centrifuged at 2500 g for 30 min at 4° C., and any expressed liquid is removed. This liquid is added to the clot-free liquid collected previously and the pooled liquid is centrifuged as described above. The serum is removed from the cell pellet with the Pasteur pipet. The serum is tested for the presence of antibodies by ELISA (see below). If the antibody reaction is weak, the rabbit is injected again one month after the test with 100 µg of antigen. Blood is drawn again ten days after this injection. To keep the antibody titers high, the rabbi is injected every month. Blood is drawn for antibody testing ten days after each injection. Antibodies are stored in small aliquots at a minimum of –20° C.

An ELISA test is used to determine antibody titer in the immunized sera. In this test, the wells of a standard assay plate (96 well plate, VWR, cat. #62409-050) are coated with purified antigen (Ambion: RNase A (cat. #2271), RNase 1 (cat. #2294), RNase T1 (cat. #2280). Ten wells are required for each serum tested, and it is possible to use assay plates with 9 or 12 well strips, or use only a portion of a standard 96 well plate. Antigen is diluted to 0.25 µg/ml in 1× PBS buffer (Ambion, cat. #9625), and 100 µl of the diluted antigen is added to each well. The plate is incubated for a minimum of 2 hours at room temperature, or overnight at 4° C. After incubation, each well is washed at least three times with double distilled $H_2O$ and the wells are tapped dry. The unbound sites in the well plate are blocked by adding 100 µl blocking buffer (1% BSA in PBS) (10×PBS, Ambion cat. #9625; BSA, Ambion, cat. #2616) to each well and shaking 60 minutes at room temperature. Each well is then washed at least three times with double distilled $H_2O$ and tapped dry.

In order to add primary antibody, the antisera is diluted 500× in blocking buffer and serially diluted across the row of the well plate as follows: blank, secondary antibody only (2000× dilution in blocking buffer), primary antibody only (500×), 500×, 1000×, 2000×, 4000×, 8000×, and 16000×.

100 µl of 500× is added to well 3 and 200 µl is added to well 4. 100 µl blocking buffer is added to wells 1,2, and 5-10. 100 µl is taken from well 4 and added to well 5. The contents of the wells are mixed thoroughly by pipeting up and down. 100 µl is removed from well 5 and mixed into well 6. Dilution is continue in this manner across the row. The well plate is then incubated for two hours at room temperature with gentle shaking. Each well is then washed at least three times with double distilled $H_2O$ and tapped dry.

The secondary goat-anti-rabbit-HRP antibody (Zymed, cat. #65-6120) is diluted 2000× in blocking buffer. 100 µl is added to wells 2, and 4-10. The wells are incubated 60 minutes at room temperature with gentle shaking. Then each well is washed at least three times with double distilled $H_2O$ and tapped dry.

100 µl ABTS color development solution (Zymed, cat. #00-2024) is added to each well, and the wells are incubated for 20 minutes at room temperature. 25 µl 2M $H_2SO_4$ (J. A. Baker, cat. #g6781-05) is then added to each well to stop the reaction.

Absorbance is read at 405 nm in a plate reader. The first 3 wells (controls) should be negative (i.e., no color) to verify that none of the components generated false positive results. An acceptable titer will give strong signal ($A_{405}$>1) with the 1000× dilution of sera. A good titer will give strong signal with 4000× and higher.

Example 3

Anti-Nuclease Antibody Purification Procedure

Anti-nuclease antibodies employed in the invention may be purified. For example, 500 ml of anti-RNase A serum or 300 ml of anti-RNase T1 or 1 serum is thawed in a 37° C. water bath and combined into one flask. Then 45% ammonium sulfate (2.77 g solid $(NH_4)_2SO_4$ for 10 ml solution) (JSB, cat. #112544) is slowly added to the serum with stirring at 4° C., avoiding any local saturation in the serum, in order to precipitate the globulins. The solution is stirred for an additional two hours at 4° C. The solution is added to 50 ml centrifuge tubes and spun at 14,000 rpm for 15 minutes to pellet the protein. The supernatant is removed and the pellet is dissolved in 50 mM sodium borate (pH 9.0). The dissolved pellet is dialyzed against three liters of 50 mM sodium borate (pH 9.0) overnight at 4° C.

Next, Triton X-100 is added to the solution to 0.1% and the pH is adjusted to 9.0 using sodium hydroxide (NaOH). The solution is stirred for 30 minutes at 4° C. The solution is then loaded onto a 25 ml Protein A Sepharose column (Protein A Sepharose, Pharmacia, cat. #17-0963-03) equilibrated with 50 mM sodium borate (pH 9.0) and 0.1% Triton. The column is washed with three column volumes of 50 mM sodium borate and 0.1% Triton. The column is then washed with two column volumes of the same buffer plus 3 M lithium chloride (LiCl). The pH of the solution should be adjusted to 9.0 after addition of the LiCl. Then wash the column with three column volumes of 50 mM sodium borate without Triton to remove the remaining detergent.

The protein is eluted with 100 mM glycine (pH 3.0) (Ultrapure Glycine, Gibco-BRL, cat. #15514-029). A fresh tube is used when the protein begins to elute from the column. Eight ml fractions of protein is eluted into 400 µl of 1 M potassium phosphate buffer (pH 7.7). Each tube is inverted several times to mix the buffer after each fraction is finished to prevent denaturing of the enzyme. A new tube is used when the protein is finished eluting to prevent dilution of the protein.

The fractions are pooled and the pH is adjusted to 6.0 with dilute HCl. The pooled fractions are loaded onto a 5 ml SP sepharose column (SP-Sepharose, Pharmacia cat. #17-0729-01) equilibrated with 20 mM potassium phosphate buffer (pH 6.8). The antibody will come off in the flowthrough fractions. The tubes are fed to a new fraction once the protein begins to flow through. The antibody fractions are dialyzed against three liters of 20 mM potassium phosphate buffer (pH 7.7), overnight at 4° C. with stirring.

The antibodies are loaded onto a 5 ml DEAE AffiBlue Gel column (DEAE AffiBlue, BioRad cat. #153-7307) equilibrated with 20 mM potassium phosphate buffer (pH 7.7). The antibodies will come off into the flowthrough fractions. The pH of the antibody fraction is adjusted to 6.0 with dilute HCl. The solution is then loaded onto an 8 ml denatured DNA column (Denatured DNA-cellulose, Pharmacia cat. #27-5579-02) equilibrated with 20 mM potassium phosphate buffer (pH 6.8). The antibodies come off in a sharp peak in the flowthrough material. The antibody fractions are pooled. The pH of anti-RNase A is adjusted to 7.7. Conductivity should be equal to 20 mM potassium phosphate buffer (pH 7.7)+10 mM NaCl. The antibodies may be diluted if necessary.

Anti-RNase A is loaded onto a 50 ml Q-sepharose column (Q-Sepharose Fast Flow, Pharmacia cat. #17-0510-01) equilibrated with 20 mM potassium phosphate buffer (pH 7.7) plus 10 mM NaCl plus 10% glycerol. The column is washed with 5 column volumes of the equilibrating buffer. The protein is then eluted with 20 mM potassium phosphate buffer (pH 7.7) and 10% glycerol.

One of skill in the art will be able to employ the disclosed method, appropriately adapted, to purify anti-DNase antibodies and non-specific anti-nuclease antibodies.

Example 4

Activity Assays for Anti-Nuclease Antibodies

The activity of anti-nuclease antibodies is readily determined using radiolabeled RNA or DNA to detect the inhibition of RNase or DNase by the anti-nuclease antibodies. In general, the nuclease and anti-nuclease antibody are separately diluted, typically in 1× assay buffer. Assay buffer, nuclease and anti-nuclease antibody are then added to 0.5 ml microfuge tubes. For assaying anti-RNase activity, a mixture comprising assay buffer, RNA and radiolabeled RNA is added to the microfuge tubes. The "MIX" of assay buffer, RNA and radiolabeled RNA is generally prepared by combining 10× Assay Buffer (0.9 µl/rxn), 5 mg/ml yeast RNA (0.4 µl/rxn), $^{32}$-β actin RNA (1 µl/rxn), and nuclease-free $H_2O$ (6.7 µl/rxn) for a total of 9 µl/rxn. The tubes are vortexed and microfuged, then incubated at 37° C. for 30 minutes. After incubation, a portion of the tube contents is removed and placed into gel loading buffer. Then the tube contents and the gel loading buffer are mixed, and the combination is loaded onto a gel, typically a 8M urea/5% acrylamide gel, which is exposed to film.

Components typically employed in these activity assays include: 10× Assay Buffer (200 mM Tris-HCl pH 7.5, 500 mM NaCl, 10 mM EDTA); 1× Assay Buffer (20 mM Tris-HCl pH 7.5, 50 mM NaCl, 1 mM EDTA, 0.1 mg/ml BSA); BSA, 50 mg/ml (Ambion cat. #2616); Medium specific-activity $^{32}$P-labeled β-actin RNA probe; 5 mg/ml yeast total RNA (Ambion cat. #7120G); nuclease-free H$_2$0; Gel Loading Buffer II (Ambion cat. #8546G); 8M urea/5% acrylamide gel; and Tris-borate/EDTA (TBE buffer).

The above method has been used by the inventors for activity assays of numerous anti-nuclease antibodies. Examples follow.

1. Activity Assay for Anti-RNase A

Radiolabeled RNA was used to detect the inhibition of RNase A by specific antibodies. The assay followed the method disclosed above. In particular, RNase A (1 mg/ml) was diluted to 25 pg/μl in 1× Assay Buffer and Anti-RNase A was diluted to 25 U/μl. The "MIX" of assay buffer, RNA and radiolabeled RNA was prepared as disclosed above. The reactions were set up in 0.5 ml microfuge tubes as indicated in the table below. 1× Assay Buffer was added first, then the nuclease and Anti-RNase A were added, with MIX added as a last component. The tubes were vortexed and microfuged, then incubated at 37° C. for 30 min (Table 3).

TABLE 3

| Tube | 1 × Assay Buffer (μl) | Rnase A (μl) | Anti-RNase A Antibody (μl) | MIX (μl) |
|---|---|---|---|---|
| 1 | 11 | — | — | 9 |
| 2 | 10 | 1 (25 pg) | — | 9 |
| 3 | 9 | 2 (50 pg) | — | 9 |
| 4 | 8 | 3 (75 pg) | — | 9 |
| 5 | 7 | 4 (100 pg) | — | 9 |
| 6 | 10 | — | 1 | 9 |
| 7 | 9 | 1 | 1 | 9 |
| 8 | 8 | 2 | 1 | 9 |
| 9 | 7 | 3 | 1 | 9 |
| 10 | 6 | 4 | 1 | 9 |
| 11 | 11 | — | — | 9 |

At the end of the incubation time, 10 μl of solution was removed from the tube and placed into 10 μl Gel Loading Buffer II. The combination was mixed thoroughly and loaded onto a 8M urea/5% acrylamide gel. The gel was exposed to film for 30 min. at −80° C. with an intensifying screen.

The probe should be completely degraded with all levels of RNase A alone. There should be a full-length probe visible in the presence of 50 pg RNase A and a final concentration of 1 U/μl Anti-RNase A.

2. Activity Assay for Anti-RNase 1

Radiolabeled RNA was used to detect the inhibition of RNase 1 by specific antibodies. The assay followed the method disclosed above. In particular, RNase 1 (100 U/μl was diluted to 1 U/μl in 1× Assay Buffer. The "MIX" was prepared as disclosed above. The reactions were set up in 0.5 ml microfuge tubes as indicated in the table below. 1× Assay Buffer was added first, then the nuclease, Anti-RNase 1, and MIX were added. The tubes were vortexed and microfuged, then incubated at 37° C. for 30 min (Table 4).

TABLE 4

| Tube | 1 × Assay Buffer (μl) | Rnase 1 (μl) | Anti-Rnase 1 Antibody (μl) | MIX (μl) |
|---|---|---|---|---|
| 1 | 11 | — | — | 9 |
| 2 | 10 | 1 (1 U) | — | 9 |
| 3 | 8.5 | 2.5 (2.5 U) | — | 9 |
| 4 | 6 | 5 (5 U) | — | 9 |
| 5 | 3.5 | 7.5 (7.5 U) | — | 9 |
| 6 | 10 | — | 1 | 9 |
| 7 | 9 | 1 (1 U) | 1 | 9 |
| 8 | 7.5 | 2.5 (2.5 U) | 1 | 9 |
| 9 | 5 | 5 (5 U) | 1 | 9 |
| 10 | 2.5 | 7.5 (7.5 U) | 1 | 9 |
| 11 | 11 | — | — | 9 |

At the end of the incubation time, 10 μl of solution was removed from the tube and placed into 10 μl Gel Loading Buffer II. The combination was mixed thoroughly and loaded onto a 8M urea/5% acrylamide gel. The gel was exposed to film for 30 min. at −80° C. with an intensifying screen.

The probe should be completely degraded in the presence of RNase 1 alone. There should be a full-length probe visible in the presence of 5U RNase 1 and a final concentration of 0.175 mg/ml anti-RNase 1.

3. Activity Assay for Anti-RNase T1

Radiolabeled RNA was used to detect the inhibition of RNase T1 by specific antibodies. The assay followed the method disclosed above. In particular, RNase T1 (1000 U/μl) id diluted to 0.1 U/μl in 1× Assay Buffer. The "MIX" was prepared as disclosed above. The reactions were set up in 0.5 ml microfuge tubes as indicated in the table below. 1× Assay Buffer was added first, then the nuclease, Anti-RNase T1 (4.5 mg/ml), and MIX were added. The tubes were vortexed and microfuged, then incubated at 37° C. for 30 min (Table 5).

TABLE 5

| Tube | 1 × Assay Buffer (μl) | Rnase T1 (μl) | Anti-Rnase T1 Antibody (μl) | MIX (μl) |
|---|---|---|---|---|
| 1 | 11 | — | — | 9 |
| 2 | 10 | 1 (0.1 U) | — | 9 |
| 3 | 9 | 2 (0.2 U) | — | 9 |
| 4 | 8 | 3 (0.3 U) | — | 9 |
| 5 | 6 | 5 (0.5 U) | — | 9 |
| 6 | 10 | — | 1 | 9 |
| 7 | 9 | 1 (0.1 U) | 1 | 9 |
| 8 | 8 | 2 (0.2 U) | 1 | 9 |
| 9 | 7 | 3 (0.3 U) | 1 | 9 |
| 10 | 5 | 5 (0.5 U) | 1 | 9 |
| 11 | 11 | — | — | 9 |

At the end of the incubation time, 10 μl of solution was removed from the tube and placed into 10 μl Gel Loading Buffer II. The combination was mixed thoroughly and loaded onto a 8M urea/5% acrylamide gel. The gel was exposed to film for 30 min. at −80° C. with an intensifying screen.

There should be a full-length probe visible in the presence of 0.3 U RNase T1 and a final concentration of 0.175 mg/ml Anti-RNase T1.

4. Activity Assay for Anti-S1 Nuclease

Radiolabeled RNA or radiolabeled single stranded DNA was used to detect the inhibition of S1 nuclease by specific antibodies. The assay generally followed the method disclosed above. In addition to the components typically used, this assay required both a medium specific activity, $^{32}$P-labeled β-actin RNA probe, and a medium specific activity, $^{32}$P-labeled single-stranded DNA probe. In particular, Nuclease S1 (430 U/μl) was diluted to 0.5 U/μl in 1× Assay Buffer containing 1 mM ZnSO$_4$. The "MIX" was prepared as disclosed above, except that either $^{32}$P-labeled β actin RNA (1 μl/rxn) or $^{32}$P-labeled β actin cDNA (1 μl/rxn) was used. The reactions were set up in 0.5 ml microfuge tubes as indicated in the table below. 1× Assay Buffer was added first, then the nuclease and Anti-nuclease S1 (2-3 mg/ml) were added. The MIX containing radiolabeled substrate was added as a last component. The tubes were vortexed and microfuged, then incubated at 37° C. for 30 min (Table 6).

TABLE 6

| Tube | 1 × Assay Buffer (μl) | S1 nuclease (μl) | Anti-S1 nuclease Antibody (μl) | MIX (μl) |
|---|---|---|---|---|
| 1 | 11 | — | — | 9 |
| 2 | 10 | 1 (0.5 U) | — | 9 |
| 3 | 9 | 2 (1 U) | — | 9 |
| 4 | 7 | 4 (2 U) | — | 9 |
| 5 | 3 | 8 (4 U) | — | 9 |
| 6 | 10 | — | 1 | 9 |
| 7 | 9 | 1 (0.5 U) | 1 | 9 |
| 8 | 8 | 2 (1 U) | 1 | 9 |
| 9 | 6 | 4 (2 U) | 1 | 9 |
| 10 | 4 | 8 (4 U) | 1 | 9 |

At the end of the incubation time, 10 μl of solution was removed from the tube and placed into 10 μl Gel Loading Buffer II. The combination was mixed thoroughly and loaded onto a 8M urea/5% acrylamide gel. The gel was exposed to film for 30 min. at −80° C. with an intensifying screen.

The RNA or DNA probe should be completely degraded in the presence of S1 nuclease alone. There should be a full-length probe visible in the presence of 1 U S1 nuclease and a final concentration of 0.2 mg/ml Anti-S1 antibodies.

5. Activity Assay for Micrococcal Nuclease

Radiolabeled RNA or radiolabeled single stranded cDNA was used to detect the inhibition of Micrococcal nuclease by specific antibodies. The assay generally followed the method disclosed above. In addition to the components typically used, this assay required both a medium specific activity, $^{32}$P-labeled β actin RNA probe, and a medium specific activity, $^{32}$P-labeled single-stranded DNA probe. In particular, Micrococcal nuclease (15 U/μl) was diluted to 1 U/μl in 1× Assay Buffer containing 1 mM CaCl$_2$. The "MIX" was prepared as disclosed above, except that either $^{32}$P-labled β actin RNA (1 μl/rxn) or $^{32}$P-labeled β actin cDNA (1 μl/rxn) was used. The reactions were set up in 0.5 ml microfuge tubes as indicated in the table below. 1× Assay Buffer was added first, then the nuclease and Anti-nuclease (2-3 mg/ml) were added. The MIX containing radiolabeled substrate was added as a last component. The tubes were vortexed and microfuged, then incubated at 37° C. for 30 min (Table 7).

TABLE 7

| Tube | 1 × Assay Buffer (μl) | Micrococcal nuclease (μl) | Anti-Micrococcal-nuclease Antibody (μl) | MIX (μl) |
|---|---|---|---|---|
| 1 | 11 | — | — | 9 |
| 2 | 10 | 1 (0.5 U) | — | 9 |
| 3 | 9 | 2 (1 U) | — | 9 |
| 4 | 7 | 4 (2 U) | — | 9 |
| 5 | 3 | 8 (4 U) | — | 9 |
| 6 | 10 | — | 1 | 9 |
| 7 | 9 | 1 (0.5 U) | 1 | 9 |
| 8 | 8 | 2 (1 U) | 1 | 9 |
| 9 | 6 | 4 (2 U) | 1 | 9 |
| 10 | 4 | 8 (4 U) | 1 | 9 |

At the end of the incubation time, 10 μl of solution was removed from the tube and placed into 10 μl Gel Loading Buffer II. The combination was mixed thoroughly and loaded onto a 8urea/5% acrylamide gel. The gel was exposed to film for 30 min. at −80° C. with an intensifying screen.

The RNA or DNA probe should be completely degraded in the presence of S1 nuclease alone. There should be a full-length probe visible in the presence of 1 U Micrococcal nuclease and a final concentration of 0.2 mg/ml Anti-micrococcal antibodies.

6. Activity Assay for Anti-DNase 1

Radiolabeled single stranded DNA was used to detect the inhibition of DNase 1 by specific antibodies. The assay generally followed the method disclosed above, with certain exceptions indicated below.

Components employed in this activity assay include: 10× Assay Buffer (200 mM Tris-HCl pH 7.8, 500 mM NaCl, 50 mM MgCl$_2$, 50 mM CaCl$_2$, 10 mM EDTA); (This 10× assay buffer differs from that used in the general method in the addition of 50 mM MgCl$_2$ and 50 mM CaCl$_2$, and in having a pH of 7.8); 1× Assay Buffer (20 mM Tris-HCl pH 7.5, 50 mM NaCl, 5 mM MgCl$_2$, 5 mM CaCl$_2$, 1 mM EDTA, 0.1 mg/ml BSA) (This 1× assay buffer differs from that used in the general method in the addition of 5 mM MgCl$_2$ and 5 mM CaCl$_2$.); BSA, 50 mg/ml (Ambion cat. #2616); Medium specific-activity β-actin cDNA probe (This probe differs from the Medium specific-activity β-actin probe used in the general method.); nuclease-free H$_2$0; Gel Loading Buffer II (Ambion cat. #8546G); 8M urea/5% acrylamide gel; and TBE buffer.

DNase 1 was diluted to 1 U/μl in 1× Assay Buffer. The "MIX" was prepared by combining 10× Assay Buffer (0.9 μl/rxn), $^{32}$P-labeled β actin cDNA (1 μl/rxn), and nuclease-free H$_2$O (7.7 μl/rxn) for a total of 9 μl/rxn. (Note that, unlike in the general method, no yeast RNA was used in the MIX in this sub-example.) The reactions were set up in 0.5 ml microfuge tubes as indicated in the table below. 1× Assay Buffer was added first, then the nuclease and specific anti-nuclease antibody were added. The MIX containing radio-labeled substrate was added as a last component. The tubes were vortexed and microfuged, then incubated at 37° C. for 30 min (Table 8).

TABLE 8

| Tube | 1 × Assay Buffer (μl) | Dnase 1 (μl) | Anti-DNase 1 Antibody (μl) | MIX (μl) |
|---|---|---|---|---|
| 1 | 11 | — | — | 9 |
| 2 | 10 | 1 (1 U) | — | 9 |
| 3 | 9 | 2 (2 U) | — | 9 |
| 4 | 9 | 1 (1 U) | 1 | 9 |
| 5 | 8 | 2 (2 U) | 1 | 9 |

TABLE 8-continued

| Tube | 1 × Assay Buffer (μl) | Dnase 1 (μl) | Anti-DNase 1 Antibody (μl) | MIX (μl) |
|---|---|---|---|---|
| 6 | 10 | — | 1 | 9 |
| 7 | 9 | — | 1 | 9 |

At the end of the incubation time, 10 μl of solution was removed from the tube and placed into 10 μl Gel Loading Buffer II. The combination was mixed thoroughly and loaded onto a 8M urea/5% acrylamide gel. The gel was exposed to film for 30 min. at −80° C. with an intensifying screen.

The DNA probe should be completely degraded in the presence of DNase 1 alone. There should be a full-length probe visible in the presence of 2 U DNase 1 and a final concentration of 0.2 mg/ml Anti-DNase 1 antibodies.

Example 5

Activity Assay for an Anti-Nuclease Cocktail

The activity of an anti-nuclease cocktail is readily determined using radiolabeled RNA or DNA to detect the inhibition of nuclease by anti-nuclease antibodies in the anti-nuclease cocktail. In general, the nuclease and anti-nuclease antibodies are separately diluted, typically in 1× assay buffer. Assay buffer, nuclease and an anti-nuclease cocktail are then added to 0.5 ml microfuge tubes. A mixture comprising assay buffer, RNA or DNA and radiolabeled RNA or DNA is added to the microfuge tubes, and the tubes are vortexed and microfuged. After incubation of the tubes at 37° C. for 30 minutes, a portion of the tube contents is removed and placed into gel loading buffer. After mixing, the combination is loaded onto a gel, typically a 8M urea/5% acrylamide gel, which is exposed to film.

The above method has been used by the inventors for activity assays of a specific anti-RNase cocktail as follows:

Radiolabeled RNA was used to detect the inhibition of RNase A, RNase T1, and RNase 1 by specific antibodies. The following components were needed for this assay: 10× Assay Buffer (200 mM Tris-HCl pH 7.5, 500 mM NaCl, 10 mM EDTA); 1× Assay Buffer (20 mM Tris-HCl pH 7.5, 50 mM NaCl, 1 mM EDTA, 0.1 mg/ml BSA); BSA (50 mg/ml) (Ambion cat. #2616); Medium specific-activity β-actin probe (QC SOP 0006); 5 mg/ml yeast RNA (Ambion cat. #7120G); nuclease-free H₂0; Gel Loading Buffer II (Ambion cat. #8546G); 8M urea/5% acrylamide gel; TBE buffer; Specific Anti-RNase Cocktail (25 U/μl Anti-RNase A, 4.5 mg/ml Anti-RNase 1 and 4.5 mg/ml Anti-RNase T1); and Specific RNase Cocktail (RNase A (25 ng/μl), RNase T1 (0.1 U/μl), and RNase 1 (1 U/μl) in 1× Assay Buffer).

The "MIX" was prepared by combining 10× Assay Buffer (0.9 μl/rxn), 5 mg/ml yeast RNA (0.4 μl/rxn), $^{32}$P-labeled β actin RNA (1 μl/rxn), and nuclease-free H₂O (6.7 μl/rxn), for a total of 9 μl/rxn.

The reactions were set up in 0.5 ml microfuge tubes as indicated in the table below. 1× Assay Buffer was added first. Then Specific RNase Cocktail, Specific Anti-RNase Cocktail and MIX were added. The tubes are vortexed and microfuged, then incubated at 37° C. for 30 min (Table 9).

TABLE 9

| Tube | 1 × Assay Buffer (μl) | Rnase A (μl) | Rnase 1 (μl) | Rnase T1 (μl) | Specific Anti-RNase Cocktail (μl) | Mix (μl) |
|---|---|---|---|---|---|---|
| 1 | 11 | — | — | — | — | 9 |
| 2 | 10 | 1 | — | — | — | 9 |
| 3 | 9 | 1 | — | — | 1 | 9 |
| 4 | 9.5 | — | 1.5 | — | — | 9 |
| 5 | 8.5 | — | 1.5 | — | 1 | 9 |
| 6 | 9.5 | — | — | 1.5 | — | 9 |
| 7 | 8.5 | — | — | 1.5 | 1 | 9 |
| 8 | 10 | — | — | — | 1 | 9 |
| 9 | 11 | — | — | — | — | 9 |

At the end of the incubation time, 10 μl of solution was removed from the tube and placed into 10 μl Gel Loading Buffer II. The combination was mixed thoroughly and loaded onto a 8M urea/5% acrylamide gel. The gel was exposed to film for 30 min. at −80° C. with an intensifying screen.

The probe should be fully degraded in the presence of Specific RNase. alone, and in the presence of the Specific Anti-RNase Cocktail, there should be full-length probe visible.

Example 6

Non-Antibody Nuclease Inhibitors Tested Alone and in Combination with an Anti-Nuclease Antibody Certain compounds function to inhibit nucleases ("non-antibody nuclease inhibitors"). Such compounds include, but are not limited to, dithiothreitol (DTT), heparin, polyamines (spermidine, spermine), urea, guanidine thiocyanate, detergents (sodium dodecyl sulfate), and divalent cations ($Mg^{+2}$, $Zn^{+2}$, $Cu^{+2}$, $Fe^{+2}$, $Ca^{+2}$). Non-ionic detergents are not inhibitory of nucleases per se, but have a synergistic effect with anti-nuclease antibodies to enhance the activity of the anti-nuclease antibodies.

The action of certain non-antibody nuclease inhibitors was tested by performing assays using an anti-nuclease antibody with and without addition of a non-antibody nuclease inhibitor. Results of these assays indicated inhibition of nuclease activity by the non-antibody nuclease inhibitors, as shown below.

The activities of RNase A, 1 and T1 were assayed in the manner described in Example 5 above, with the exception that $^{32}$P-labeled β actin RNA was incubated with Specific Anti-RNase Cocktail (25 U/μl Anti-RNase A, 4.5 mg/ml Anti-RNase 1 and 4.5 mg/ml Anti-RNase T1) in the absence and presence of non-antibody nuclease inhibitors. The results of these assays are shown in Table 10.

TABLE 10

| NON-ANTIBODY RNase INHIBITOR | ANTI-RNase ANTIBODY | RESULTS |
|---|---|---|
| DTT | E. coli RNase 1 | 1–3 mM DTT inhibited 1 U RNase 1 during 30 minute incubation at 37° C. |
| DTT | RNase T1 | 5–10 mM DTT inhibited 0.15 U RNase T1 |
| DTT | RNase A | At 37° C., DTT up to 250 mM did not inhibit RNase Aactivity. *DTT mixed with anti-RNase 1 and anti-RNase T1 antibodies enhanced their protective effect against Rnases 1 and T1. |
| Heparin | E. coli RNases 1 | 2.5 to 5 ug of heparin completely inactivated 1 U E. coli RNases 1. *This amount of heparin did not effect the activities of RNases A and Rnases T1. |
| Polyamines (spermidine, spermine) | RNase A | 5 to 7 mM spermidine inhibited 50 pg of RNase A. |
| Polyamines (spermidine, spermine) | RNase T1 and RNase 1 | 2.5 to 5 mM spermidine inhibited 0.2 U RNase T1 and 2 U RNase 1. |
| Polyamines (spermidine, spermine) | RNase A, T1 and 1 | 5 Mm spermidine mixed with Specific Anti-RNase Cocktail enhanced anti-RNase A, 1, and T1 activity of Specific Anti-Rnase cocktail. |
| Detergents: SDS | RNase A | 0.25% SDS inhibited activity of 50 pg of RNase A. |
| Detergents: SDS | RNase A, 1, and T1 | Addition of 0.1–0.5% SDS to Specific Anti-RNase Cocktail strengthened anti-RNase A, 1, and T1 action of Specific Anti-Rnase Cocktail. |
| Detergents: Triton X-100, NP 40, Tween 20, Chaps | RNase A, 1, and T1 | Common non-ionic (Triton X-100, Tween 20, NP-40) or zwitterionic (CHAPS) detergents, added to Specific Anti-RNase Cocktail in concentrations of 0.1% to 1% strengthened the action of Specific Anti-Rnase Cocktail against RNase A, 1, and T1. |
| Detergents: urea | Rnase A | 6 M urea inhibited RNase A activity. This concentration of urea added to the Specific Anti-Rnase Cocktail strengthened the action of Specific Anti-RNase Cocktail. |
| Detergents: guanidine thiocyanate | | 2–3 M guanidine thiocyanate added to the Specific Anti-RNase Cocktail made it more inhibitory against different antibodies. |
| Detergents: salts - MgCl$_2$ | RNase A, 1, and T1 | 50 to 100 mM MgCl$_2$ was strongly inhibitory for Rnase A, 1, and T1 activities. The best results were observed when MgCl$_2$ was mixed together with Specific Anti-RNase Cocktail. |

Those of ordinary skill in the art will be able to determine ranges at which the non-antibody nuclease inhibitors will be active.

Example 7

Nuclease Inhibitor Cocktail Use in In Vitro Transcription Reactions

In vitro synthesis of RNA transcripts from DNA templates uses purified RNA polymerases (SP6, T7 and T3 phage RNA polymerases are widely used). A typical transcription reaction may contain: 10× Transcription Buffer, nucleotides (ATP, CTP, GTP, UTP), DNA template, and RNA polymerase, although modifications will be known to those of skill in the art. RNA produced by these methods can be protected by the nuclease inhibitor cocktail of the present invention. Examples of transcription buffers containing a nuclease inhibitor cocktail are MAXIscript™, MEGAscript™, and mMESSAGE mMACHINE™ (Ambion).

Example 8

Nuclease Inhibitor Cocktail Use in Reverse Transcription Reaction

The nuclease inhibitor cocktail may be used to prevent degradation of RNA in reverse transcription reactions where reverse transcriptase is used to copy an RNA target into its complementary DNA sequence (cDNA). The cDNA can then be amplified exponentially via PCR™. A typical reverse transcription reaction and amplification reaction may contain: 10× RT Buffer, d NTP mix, Reverse Transcriptase, RNA template, PCR primers, and thermostable DNA polymerase, although modifications will be known to those of skill in the art. An example of a reverse transcription reaction containing nuclease inhibitor cocktail is RETROscript™ kit (Ambion).

Example 9

Nuclease Inhibitor Cocktail Use in In Vitro Translation Reactions Using Prokaryotic and Eukaryotic Cell-Free Lysate Various prokaryotic and eukaryotic cell-free lysates may be used for protein synthesis from RNA (translation) or DNA (coupled transcription/translation) templates. Such a protein synthesis reaction may contain: buffer, salts ($Mg^{2+}$, $K^+$), amino acids, reducing agent, RNA or DNA template, energy sources (ATP, GTP), tRNAs, and a cell-free lysate (e.g.,wheat germ lysate, rabbit reticulocyte lysate, *Drosophila* lysate, yeast lysate). Because of the nature of cell-free lysates, there is often a need to inhibit nucleases in cell-free extracts, and the nuclease inhibitor cocktail of the present application may be used in this regard. Components of a nuclease inhibitor cocktail for a cell-free extract may include one or more anti-nuclease antibodies that inhibit nucleases from the specifies from which the cell-free extract is derived.

The methods and compositions of the present invention can be used for making mRNA dependent cell-free translation systems in which a RNase is used to degrade endogenous mRNA, and the RNase is subsequently inactivated by addition of a nuclease inhibitor, including an anti-nuclease antibody to the RNase and/or a non-antibody nuclease inhibitor such as RIP.

Preparing Bacterial Cell-free Lysates

To generate an RNase-deficient cell-free lysate from *Escherichia coli*, two approaches may be used: (1) a genetic approach, employing RNase-deletion mutants, to eliminate RNases that are non-essential for viability, in combination with (2) the antibody approach to inactivate RNases essential for viability. RNase II is a major *E. coli* exoribonuclease that accounts for up to 90% of the exoribonucleolitic activity in crude cell-free extract (Spicler and Mackie (2000)).

To provide anti-RNase antibodies for generating an RNase-deficient cell-free lysate, *E. coli* RNase II is overexpressed and purified as described by Coburn and Mackie (1996). The purified RNase II is then injected into rabbits to generate anti-RNase II antibodies as described in Example 2 above. The anti-RNase II antibodies are added to the bacterial cell-free lysate to block endogenous ribonucleases and improve in vitro protein synthesis in bacterial cell-free lysate(s). Anti-nuclease antibodies against additional *E.coli* nucleases, such as PNPase, RNase E and DNase isolated from *E.coli* lysate, are obtained in order to improve stability of the DNA template/RNA transcript.

Use of anti-nuclease antibodies is expected to dramatically improve the efficiency of in vitro transcription/translation reactions. For example, cell-free lysate obtained from MRE 600 *E. coli* stain contains many nucleases, including periplasmic RNase 1. RNase 1 is inhibited by anti-RNase 1 antibodies. Addition of 3 µg of anti-RNase 1 antibodies significantly prolonged the half-life of translated mRNA (from 2 minutes to 7.5 minutes), and at the same time increased the amount of synthesized protein by 40 to 45%.

Preparing Eukaryotic Cell-free Lysates

A reticulocyte lysate can be prepared using nucleases, including RNase A, 1, or T1, and the specific anti-RNase antibody to the RNase.

In vitro protein synthesis is a method of producing proteins in cell-free extracts using either mRNA (translation process) or DNA (coupled transcription:translation) as a template. Rabbit reticulocyte lysate is the most popular cell-free system used for in vitro protein synthesis. This lysate contains all the macromolecular components (ribosomes, tRNAs, aminoacyl-tRNA synthetases, initiation, elongation, and termination factors, etc.) required for translation of RNAs. This crude cell-free extract also contains a large amount of globin mRNA and is known as untreated reticulocyte lysate. The endogenous globin mRNA can be removed by incubation with $Ca^{2+}$ dependent Micrococcal nuclease which is later inactivated by the chelation of $Ca^{2+}$ by EGTA. Nuclease treated reticulocyte lysate was first described by Pelham and Jackson (1976), and since then is the most popular eukaryotic cell-free expression system used in vitro translation studies. However, there are some drawbacks to this method.

An alternative to using Micrococcal nucleases with $Ca^{2+}$ followed by chelating with EGTA is to use a nuclease and an antibody that inhibits the nuclease. For example, RNase A, RNase 1, RNase T1, and even Micrococcal nuclease is used to degrade endogenous mRNAs in the cell-free lysate followed by their inactivation with specific antibodies raised against these nucleases. Antibodies are added either directly to the lysate in a liquid form and left there as inactive nuclease/antibody complex or are immobilized on the beads and after mixing with the treated lysate removed easily by centrifugation together with bound nuclease, leaving lysate nuclease-free.

This alternative method may also allow better mRNA dependent lysates to be made in other systems such as Hela cells or wheat germ. Other RNase:inhibitor couples are barnase and barstar, ribonuclease A and its specific inhibitor such as RIP or mammalian ribonucleases and their low molecular weight inhibitors (3', 5'-Pyrophosphate-linked nucleotides) described by Russo and Shapiro (1999).

Preparing Microsomal Membrane Fractions

Pancreatic microsomal membranes are used to study co-translational and initial post-translational processing of proteins, such as signal peptide cleavage, membrane insertion, translocation, and core glycosylation. To assure good quality membranes, microsomes have to free from contaminating ribonucleases and be stripped of endogenous membrane-bound ribosomes and mRNA. The most popular and commercially available pancreatic microsomal membrane is canine pancreatic microsomal fraction. Isolation of the microsomal membrane fractions from other sources may be difficult due to the high content of endogenous nucleases. Membrane preparation from any other sources may be improved by use of specific antibodies to membrane associated ribonucleases and other cellular nucleases.

Example 10

Nuclease Inhibitor Cocktail as an RNA Storage Solution

It is possible to store RNA from any source in the nuclease inhibitor cocktail so as to protect the RNA from degradation. This can be achieved, for example, by adding Specific Anti-RNase Cocktail to RNase storage buffer to the final concentration of 0.5 to 1.0 U/µl (20 to 40 fold dilution).

Example 11

Non-Antibody Nuclease Inhibitors as Nuclease Inhibitor Cocktail

A combination of non-antibody nuclease inhibitors can be used to inhibit nucleases. For example, a mixture of the nuclease inhibitors $Mg^{+2}$ and spermine provided greater inhibition of RNase A activity than either $Mg^{+2}$ or spermine provided individually.

Example 12

In Vitro Translation Kits

Kits for the performance of in vitro translation which comprises at least one anti-nuclease antibody or other RNase inhibitor, or an RNase inhibitor cocktail and some or all of the necessary components for, or to make, a cell-free translation system can be made according to the invention.

In vitro translation is a process of protein synthesis outside the living cell using cell-free extract and mRNA transcript as genetic material for translation. The in vitro synthesis of proteins in cell-free extracts is an important tool for molecular biologists and has a variety of applications, including the rapid identification of gene products, localization of mutations through synthesis of truncated gene products, protein folding studies, and incorporation of modified or unnatural amino acids for functional studies. The use of in vitro translation systems can have advantages over in vivo gene expression when the over-expressed product is toxic to the host cell, when the product is insoluble or forms inclusion bodies, or when the protein undergoes rapid proteolytic degradation by intracellular proteases.

Rabbit reticulocyte lysate is a highly efficient in vitro eukaryotic protein synthesis system used for translation of exogenous RNAs (either natural or generated in vitro). In vivo, reticulocytes are highly specialized cells primarily responsible for the synthesis of hemoglobin, which represents more than 90% of the protein made in the reticulocyte. These immature red cells have already lost their nuclei, but contain adequate mRNA, as well as complete translation machinery, for extensive globin synthesis. The endogenous globin mRNA may be eliminated by incubation with a nuclease inhibitor. Wheat germ extract is a convenient alternative to the rabbit reticulocyte lysate cell-free system, and the same advantages of inhibitors may be realized in it or in other systems such as the *Drosophila* extract system.

E. coli cell-free systems consist of a crude extract that is rich in endogenous mRNA. The extract is incubated during preparation so that this endogenous mRNA is translated and subsequently degraded. Because the level of endogenous mRNA in the prepared lysate is low, the exogenous product is easily identified. In comparison to eukaryotic systems, the *E.coli* extract has a relatively simple translational apparatus with less complicated control at the initiation level, allowing this system to be very efficient in protein synthesis. Bacterial extracts are often unsuitable for translation of RNA, because exogenous RNA is rapidly degraded by endogenous nucleases. A nuclease inhibitor may be used to inhibit the degradation of exogenous RNA in the *E. coli* system.

Example 13

Intactness of Total RNA Challenged With RNases in the Presence of RIP, Citrate or EDTA Tissues (5 mg) were dounced in 50 ul of non-denaturing, neutral ph buffer (24 mm hepes, ph 7.2, 50 mm nac1, 1 mm mgc1$_2$). Diluted tissue lysates (pancreas 1:20,000; liver 1:5) or 5 pg/ul bovine rnase a were pre-incubated with 0.2u/ul rip, 50 mm citrate or 5 mm edta for 30 sec. A total of 100 pg/ul *e. Coli* total rna was then added to the mixture and incubated at room temperature for an additional 4 min (FIG. 1., Lanes 1-5) or 5.5 min (lanes 6&7). The ma was purified via megaclear™ mag-96 (ambion, inc.) And eluted with 20 ul nuclease-free water. The sample (1 ul) was analyzed by bioanalyzer 2100 after separation on an ma labchip. "production source" denotes ambion's prepared rna product that is homogenized and purified by organic extraction. This example demonstrates that a model protein inhibitor (rip) and a model chelator (citrate and edta) can offer significant protection from ma degradation when challenged by mases (FIG. 1). Because the mechanism of action of these inhibitors is distinct, combinations of these inhibitors are expected to help control different mase activities. For example, rip is effective against mammalian mase a superfamily enzymes. Rnase a activity is inhibited by chelators.

Example 14

OVA and SDS Protect RNA from Degradation in a Highly Dilute Pancreatic Lysate

Figure 2:
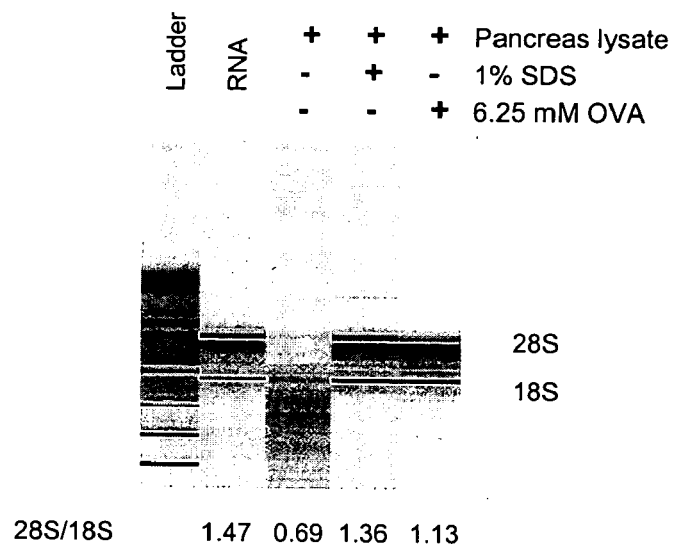
FIG. 2 OVA and SDS Protect RNA from Degradation in a Dilute Pancreatic Lysate.

Pancreatic lysate (0.1 mg/ml) was diluted 1:20,000 in 24 mM Hepes, pH 7.2, 50 mM NaCl, 1 mM MgCl$_2$ and pre-incubated with either 1% SDS or 6.25 mM OVA for 30 s prior to the addition of 2 ug mouse liver total RNA. Reactions were incubated at 25 C for an additional 4 min, quenched, and analyzed on an RNA LabChip. As shown in FIG. 2, two fundamentally different types of RNase inhibitors (a small molecule organic compound and an ionic detergent) can help remedy RNA degradation. Inasmuch as various RNase activities have differential sensitivities to such inhibitors, combinations of these inhibitors would be more effective than any single inhibitor alone.

Example 15

Ap5A Inhibits Total RNase Activity in Tissue Lysates

Flash-frozen mouse tissues (5 mg) were dounced in 50 ul of 24 mM Hepes, pH 7.2, 50 mM NaCl, 1 mM MgCl$_2$. RNase activity was measured using Ambion's fluorescent RNaseAlert™ assay (40 nm substrate, 10 ug/ml ultrapure BSA) via BMG POLARstar Optima Fluorometer according to the manufacturer's protocol. In addition to measuring total RNase activity, lysates were treated with Ap5A, heat (90 C for 10 min), or 0.5 U/ul RIP. Tissue lysate dilutions: pancreas 1:16,200; liver 1:17; thymus 1:17; kidney 1:17; spleen 1:810; lung 1:810. The data were normalized to maximum RNase activity observed in tissue lysate with kidney being the tissue with the lowest RNase activity and assigned the arbitrary unit of 1. In diluted mouse pancreatic lysate, Ap5A exhibited a Ki ~200 nM. Additionally, RIP successfully inhibits much of the RNase activity in these particular tissue lysates. These results (Tables 11 and 12) reveal that both Ap5A and RIP can be an effective inhibitor of RNases present in vivo. However, RIP is specific to RNase A superfamily enzymes, where Ap5A, as a RNA analogue, is expected to be a more general RNase inhibitor.

TABLE 11

| Tissue Lysate | Slope/sec | % Inhibition |
|---|---|---|
| Pancreas | 24.37 | pancreas control |
| Pancreas + 232 uM Ap5A | 13.58 | 44.3 |
| Pancreas + 1.3 mM Ap5A | 3.05 | 87.5 |
| Pancreas + 2.9 mM Ap5A | 0.55 | 97.7 |
| Liver, heated | 16.5 | liver control |
| Liver, heated + 2.9 mM Ap5A | 0.46 | 97.2 |
| Thymus, heated | 2.89 | thymus control |
| Thymus, heated + 2.9 mM Ap5A | 0.33 | 88.5 |
| Kidney, heated | 1.79 | kidney control |
| Kidney, heated + 2.9 mM Ap5A | 0.02 | 98.9 |

TABLE 12

| Tissue | Slope/sec$_{Initial}$ (Before RIP addition) | Slope/sec$_{Final}$ (After RIP addition) | % Inhibition |
|---|---|---|---|
| Pancreas | 60.00 | 0.17 | 99.7 |
| Spleen | 53.58 | 1.08 | 98.0 |
| Lung | 29.68 | 0.21 | 99.3 |

Example 16

Proteinase K Inactivates Total RNase Activity in Tissue Lysates

Murine kidney (40 ul of 0.1 mg/ul) was introduced into a 50 uL reaction with a dilute pancreatic lysate (1 or 10 ul of pancreas at 0.1 mg/ul) prepared in 24 mM Hepes, pH 7.2, 50 mM NaCl, 1 MM MgCl$_2$. All samples were digested at 50C for 5 min in PK buffer at 23C. The results (Table 13) show that proteinase K can be a powerful inactivator of RNases in vivo. Although proteinase K is a protein-based inhibitor, RNase inactivation occurs by a very different mechanism than a protein inhibitor such as RIP, since proteinase K digests RNase proteins to peptide fragments, thereby destroying the folded (active) conformation of the enzyme.

TABLE 13

| Contents | Slope (RFU/sec) | Fold Reduction |
| --- | --- | --- |
| 1 uL pancreas, no PK | 120.3405 | — |
| 10 uL pancreas, no PK | 147.1595 | — |
| No pancreas, 600 ng/uL PK | 0.0123 | — |
| 1 uL pancreas, 600 ng/uL PK | 0.0938 | 1283 |
| 10 uL pancreas, 600 ng/uL PK | 0.6074 | 242 |

Example 17

Affinity Resin Treatment Removes Total RNase Activity From Tissue Lysates

Pancreatic tissue (5 mg) was dounced in 50ul of 24 mM Hepes, pH 7.2, 50 mM NaCl, 1 mM $MgCl_2$. Diluted pancreas lysate (1:12,000) was subjected to a 1/10 volume of negatively charged SP resin. RNase activity of the clarified lysate was measured using. Ambion's fluorescent RNaseAlert™ assay (40 nM substrate, 10 ug/ml ultrapure BSA) via BMG POLARstar Optima, according to the manufacturer's instructions. Resin treatment removed >95% of total RNase activity in diluted pancreas lysate. As shown in Table 14, this resin inactivates >95% of the RNase activity from this tissue. In this case, inactivation is accomplished by binding of the positively-charged RNase to the negatively-charged sulfopropyl resin. Thus the RNases can be physically removed from the tissue lysate and separated from the RNA that they might otherwise degrade over time.

TABLE 14

| Tissue | Slope/Sec | % Inhibition |
| --- | --- | --- |
| Pancreas | 17.59 | 0 (positive control) |
| Resin treated pancreas | 0.70 | 96 |

Example 18

Salt-Based Inhibition of RNase Activity in Tissue Lysates

Figure 3A:
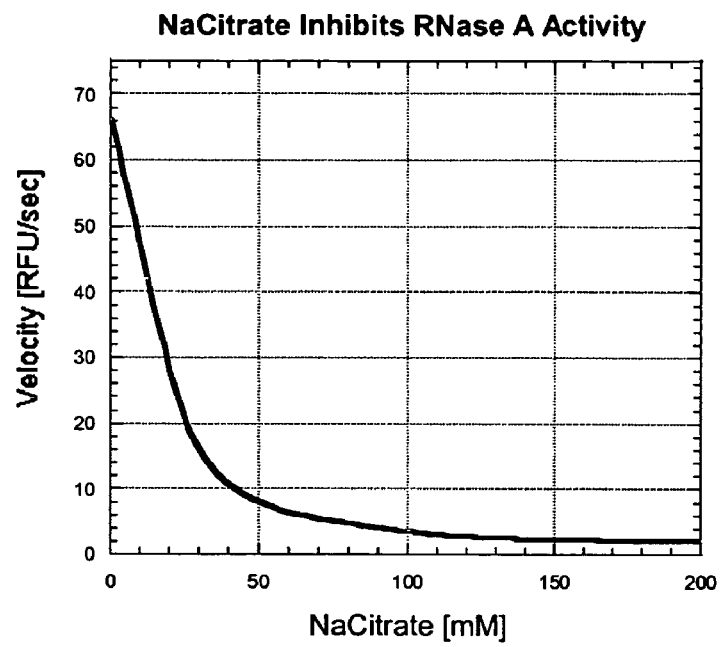
FIG. 3A and FIG. 3B Salt-based Inhibition of RNase Activity in Tissue Lysates.
Figure 3B:
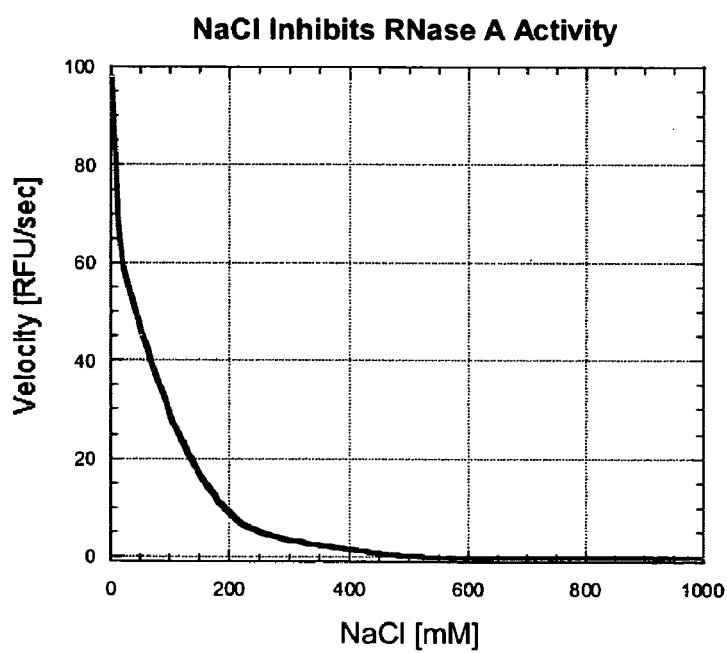

A 1:1000 dilution of pancreatic lysate (1 ul) prepared in 24 mM Hepes, pH 7.2, 50 mM NaCl, 1 mM $MgCl_2$ was added to 200 nM RNaseAlert™ in RNaseAlert™ buffer (Ambion, Inc.) containing bovine RNase A. Activity was monitored by fluorescence at 490/520 nm in the presence of increasing salt concentrations. The results given in FIG. 3A and FIG. 3B profile the salt sensitivity of the RNases present in this in vivo sample. These data reveal that raising the ionic strength of the solution can be an effective way to help control RNase activity in biosamples such as tissue, and, in particular, the combination of high salt and other RNase inhibitors is a viable strategy for reducing RNA degradation.

Example 19

Chemical Formulas and IUPAC Names for Exemplary Small Molecule Inhibitors of Nuclease Activity

TABLE 15

| Library[α] | Structure | Compound Reference # | IUPAC Name |
| --- | --- | --- | --- |
| NCI | (structure shown) | 65828 | 8-amino-5-(4'-hydroxybiphenyl-4-yl-azo)naphthalene-2-sulfonate |
| NCI | (structure shown) | 65820 | 6-hydroxy-5-(2-hydroxy-3,5-dinitro-phenyl-azo)naphthalene-2-sulfonate |

TABLE 15-continued

| Library[α] | Structure | Compound Reference # | IUPAC Name |
|---|---|---|---|
| Sigma | 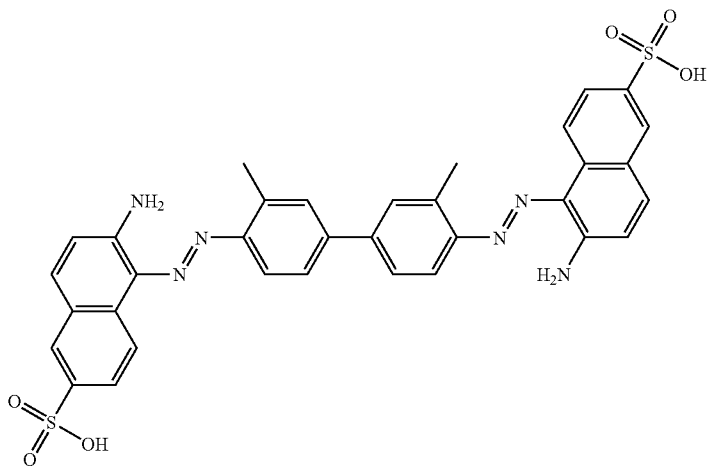 | Benzopurpurin B (BpB) | 3,3'-dimethylbiphenyl-4,4'-bis(2-amino-naphthylazo-6-sulfonate) |
| C | | 181431 | 4,4'-dicarboxy-3,3'-bis(naphthylamido)diphenylmethanone |
| C | | 473872 | 3,3'-dicarboxy-4,4'-bis(4-biphenylamido)diphenylmethane |
| C | | 467929 | 3,3'-dicarboxy-4,4'-bis(3-nitrophenylamido)diphenylmethane |

TABLE 15-continued

| Library | Structure | Compound Reference # | IUPAC Name |
|---|---|---|---|
| Sigma | 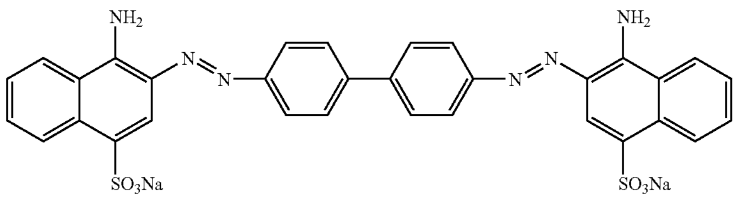 | | Benzopurpurin 4B (Bp4B) |
| C | | 140553 | 2-(4-iodophenoxy)-1-(2,4,6-trihydroxyphenyl)ethanone |
| C | | 112680 | 5-[3-(2-furly)-2-propen-1-yl]-2,2-dimethyl-1,3-dioxane-4,6-dione |
| C | | 102704 | 4-[5-(3-carboxy-5-oxo-1-phenyl-1,5-dihydro-4H-pyrazol-4-ylidene)-1,3-pentadien-1-yl]-5-hydroxy-1-phenyl-1H-pyrazole-3-carboxylic acid |
| C | | 128773 | 3-(2,5-dimethyl-1H-pyrrol-1-yl)benzoic acid |
| C | | 180582 | 3,3'-methylenebis(6-[4-methylphenylsulfonyl]amino)benzoic acid |

TABLE 15-continued

| Library[α] | Structure | Compound Reference # | IUPAC Name |
|---|---|---|---|
| C | 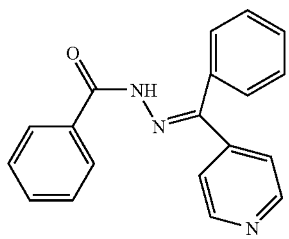 | 227726 | N'-[phenyl(4-pyridinyl)methylene]benzohydrazide |

Example 20

Intactness of Total RNA Challenged With RNases in the Presence of Benzopurpurin B (BpB)

Mouse pancreatic tissue (5 mg) was disrupted in 50 ul of 24 mM Hepes, pH 7.2, 50 mM NaCl, 1 mM MgCl$_2$. The diluted lysate (1:20,000) was pre-incubated with 50 uM Benzopurpurin B (BpB) for 30 sec and then added to 100 ng/ul mouse liver total RNA (Ambion) and incubated at 23 C for an additional 4 min. Samples were quenched in a guanidinium lysis buffer, and the RNA purified via MEGAclear™ MAG-96 and eluted with 20 ul nuclease-free water. Experiments assessing the inhibition of purified RNases used 8.3 pg/ul bovine RNase A, 1 ng/ul eosinophil-derived neurotoxin (EDN), 1 ng/ul human pancreatic RNase (HPR), 7 ng/ul E. coli RNase I, or 100 pg/ul RNase T1. These experiments were conducted in the same fashion except that 100 uM BpB was employed. The sample (1 ul) was analyzed by 2100 BioAnalyzer software (Agilent) after separation on an RNA LabChip. "Production Source" denotes Ambion's prepared RNA product that is homogenized and purified by organic extraction. FIG. 4 shows that BpB offers significant protection from RNA degradation when challenged by a number of RNases from both in vivo and in vitro sources. Furthermore, this experiment reveals the BpB is an effective inhibitor against a number of RNases in the RNase A superfamily (e.g., bovine RNase A, HPR, and EDN), as well as an evolutionarily distinct RNase, RNase I from E. coli.

Example 21

Use of Anti-RNase T1 in Combination With RIP or Benzopurpurin B Effectively Inhibits RNase A and RNase T1 Activities As shown in FIG. 5, use of Anti-RNase T1 in combination with RIP or Benzopurpurin B effectively inhibits RNase A and RNase T1 activities. A total of 2.5 pg/ul bovine RNase A and 25 pg/ul RNase T1 (collectively termed "RNase Mixture") was pre-incubated with 40 U RNase Inhibitor (RIP), 176.25 ng/ul Anti-RNase T1, or 200 uM Benzopurpurin B (BpB) for 30 seconds followed by the addition of 100 pg/ul mouse liver production source total RNA. Reactions were incubated at room temperature for an additional 4 minutes. RNA was purified using MEGAclear™ MAG-96 and eluted with 20 ul nuclease-free water. The sample (1 ul) was analyzed by BioAnalyzer 2100 after separation on an RNA LabChip. "Production Source" denotes Ambion's prepared RNA product that are homogenized and purified by organic extraction. This result clearly shows that a combination of two distinctive RNase inhibitors, namely an antibody against RNase T1 and RIP or BpB, is more effective than a single inhibitor in minimizing RNA degradation from a solution containing more than one type of RNase (here, RNase A and RNase T1).

Example 22

Intactness of Total RNA Challenged With RNases in the Presence of Benzopurpurin 4B (Bp4B)

Figure 6:
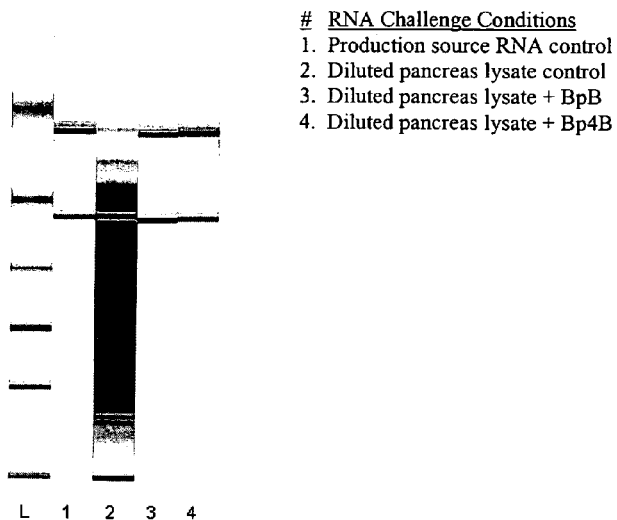
FIG. 6 Intactness of total RNA challenged with RNases in the presence of Benzopurpurin 4B (Bp4B). Lane 1: Production source RNA control; lane 2: Diluted pancreas lysate control; lane 3: Diluted pancreas lysate+BpB; and lane 4: Diluted pancreas lysate+Bp4B.

Mouse pancreatic tissue (5 mg) was dounced in 50 ul of 24 mM Hepes, pH 7.2, 50 mM NaCl, 1 mM MgCl$_2$. A diluted lysate (1:20,000) was pre-incubated with 100 uM BpB or the analog Benzopurpurin 4B (Bp4B) for 30 sec and then added to 100 ng/ul mouse liver total RNA (Ambion) and incubated at 23 C for an additional 4 min. Samples were quenched in a guanidinium lysis buffer, and the RNA purified via MEGAclear™ MAG-96 and eluted with 20 ul nuclease-free water. The sample (1 ul) was analyzed by 2100 BioAnalyzer software (Agilent) after separation on an RNA LabChip. "Production Source" denotes Ambion's prepared RNA product that is homogenized and purified by organic extraction. As shown in FIG. 6, Bp4B, as well as BpB, offers significant protection from RNA degradation when challenged by native RNases from tissue.

Example 23

Intactness of Total RNA Challenged With RNases in the Presence of Chembridge Compound #467929

Figure 7:
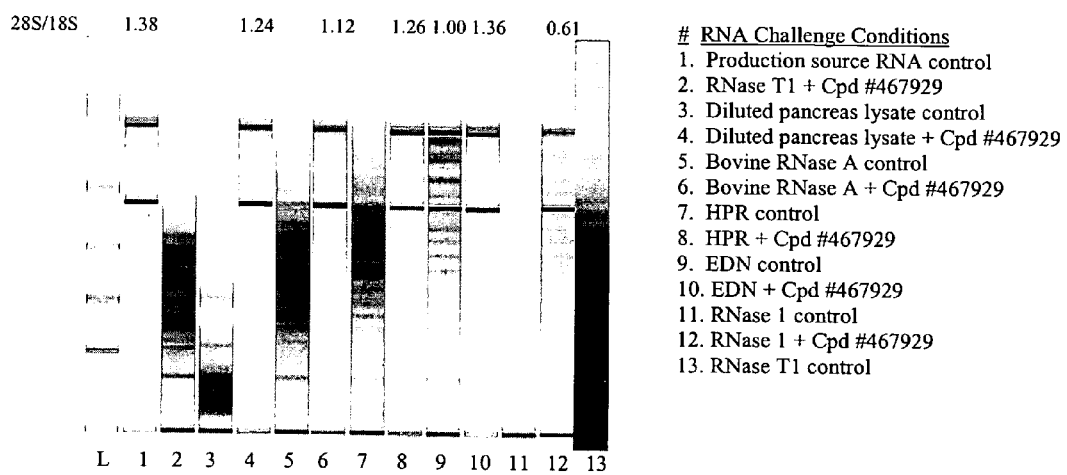
FIG. 7 Intactness of total RNA challenged with RNases in the presence of Chembridge compound #467929. Lane 1: Production source RNA control; lane 2 RNase T1+Cpd #467929; lane 3: Diluted pancreas lysate control; lane 4: Diluted pancreas lysate+Cpd #467929; lane 5: Bovine RNase A control: lane 6: Bovine RNase A+Cpd #467929; lane 7: HPR control; lane 8: HPR+Cpd #467929; lane 9: EDN control; lane 10: EDN+Cpd #467929; lane 11 RNase 1 control; lane 12: RNase 1+Cpd #467929; and lane 13 RNase T1 control.

Pancreatic tissue (5 mg) was dounced in 50 ul of 24 mM Hepes, pH 7.2, 50 mM NaCl, 1 mM MgCl$_2$. The lysate was diluted (1:20,000) and then pre-incubated with 200 uM of 467929. The inhibition of several highly purified RNases was tested, namely bovine RNase A (8.3 pg/ul final), HPR (1 ng/ul final), EDN (1 ng/ul), and E. coli RNase I (2.5 ng/ul). All samples were pre-incubated for 30 sec before being added to 100 ng/ul mouse liver total RNA (Ambion) and incubated at 23C for an additional 4 min. The RNA was then immediately purified via MEGAclear™ MAG-96 and eluted with 20 ul nuclease-free water. The recovered RNA (1 ul) was analyzed by 2100 BioAnalyzer software after separation on an RNA LabChip. Significantly, compound 467929 protected RNA against all purified RNases, save RNase T1 (FIG. 7). In addition this inhibitor also controlled RNA degradation in a crude tissue lysate, thus enabling its utility in a complex biosample where many different types of RNases are known to be present (FIG. 7, compare lanes 3 and 4).

Example 24

Tolerance of Benzopurpurin B in DNase I Digestions

Figure 8:
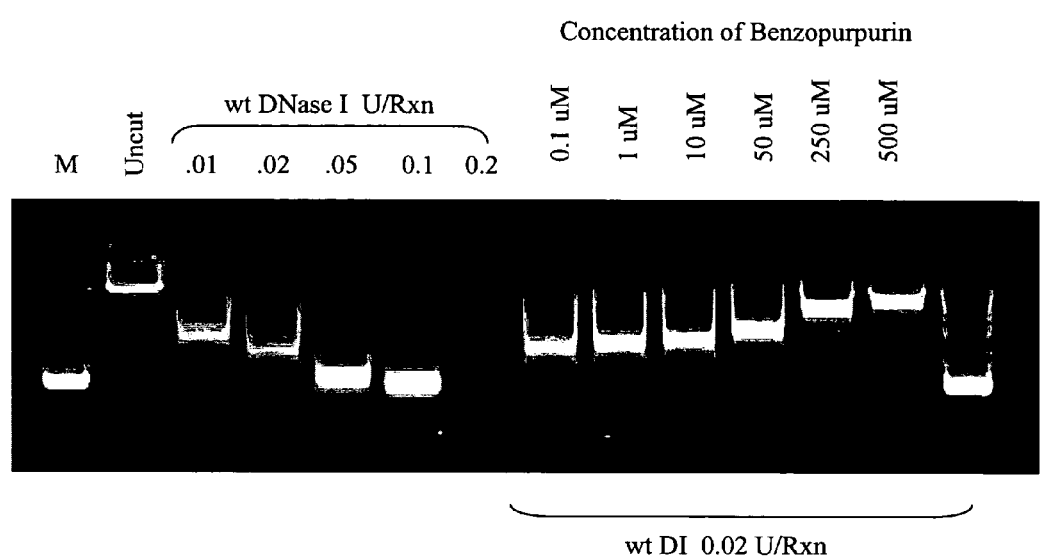
FIG. 8 Tolerance of Benzopurpurin B in DNase I digestions.

One application for small molecule RNase inhibitors is as an RNA control agent during enzymatic manipulation of solutions containing RNA. These reactions include in vitro transcription, in vitro translation, DNase digestion, and reverse transcription, among others. For this application to be successful, the RNase inhibitors of interest should not significantly interfere with enzyme-mediated RNA transactions. To this end, small molecule RNase inhibitors were tested in an industry-standard lambda digestion assay to determine if they inhibited DNase I activity (0.02 U) over a range of inhibitor concentrations. 1 ug of lambda DNA was incubated in 1×DNase I buffer and 0.02 U of DNase I with 5% DMSO or 5% DMSO plus various concentrations of RNase inhibitor for 10 min at 37C. All reactions were quenched with EDTA and the cleavage products resolved on a 1% agarose gel. As shown in FIG. 8, BpB was tolerated at concentrations of up to 10 uM with little or no effect on the efficiency of enzymatic DNA cleavage.

Example 25

Tolerance of Benzopurpurin B and Benzopurpurin 4B in qRT-PCR

To evaluate the compatibility of Benzopurpurin B and 4B in RT-PCR applications, 100 nM, 1 uM, 10 uM, and 25 uM were tested in Ambion's MessageSensor RT-PCR Kit using the supplier's instructions and using primers/probe designed to amplify a 226 nt amplicon from the human GAPDH mRNA. Reaction conditions: 20-ul one-step RT-PCR with MMLV-RT (0.4 U/ul final) and SuperTaq (0.04 U/ul final). Cycling conditions: Stage 1. 42 C for 15 minutes, Stage 2. 95 C for 5 min, Stage 3. 95 C-15 sec and 60 C-60 sec, where Stage 3 is repeated 40 times. Both Benzopurpurin B and Benzopurin 4B demonstrably inhibited RT-PCR when the concentration of inhibitor was greater than or equal to 25 uM. The compound was tolerated at 10 uM or lower with no significant loss of sensitivity (Table 16).

Example 26

$K_i$ Determination for Compound #467929 Against Bovine RNase A

Figure 9:
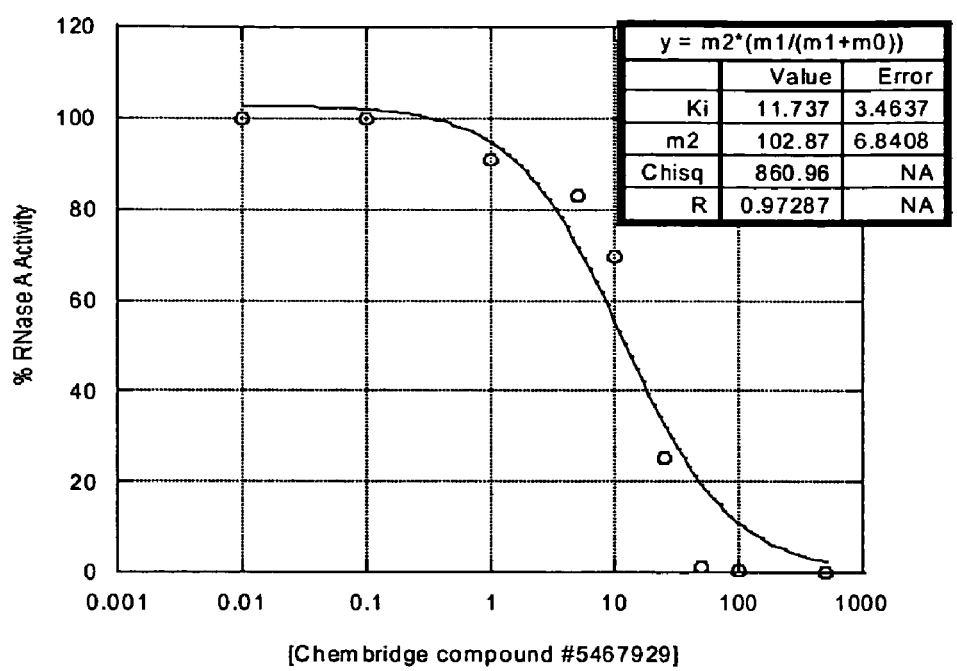
FIG. 9 $K_i$ Determination for Compound #467929 against Bovine RNase A.

To measure the inhibition constant of compound #467929 against bovine RNase A, Dixon analysis was used to determine the relationship between RNase activity and inhibitor concentration. The RNaseAlert™ fluorescence assay (Ambion) was used to quantify RNase activity. Each reaction contained 74 pM RNase A, 40 nM RNaseAlert™ substrate, and 10 ug/ml BSA in a reaction buffer consisting of 24 mM HEPES (pH 7.0), 50 mM NaCl, and 5 mM $MgCl_2$. The $K_i$ for 467929 in this assay was approximately 12 uM, consistent with previous reports (Shapiro, 2003) (FIG. 9). These data can help quantify the effectiveness of this inhibitor at various doses of usage.

Example 27

Figure 10:
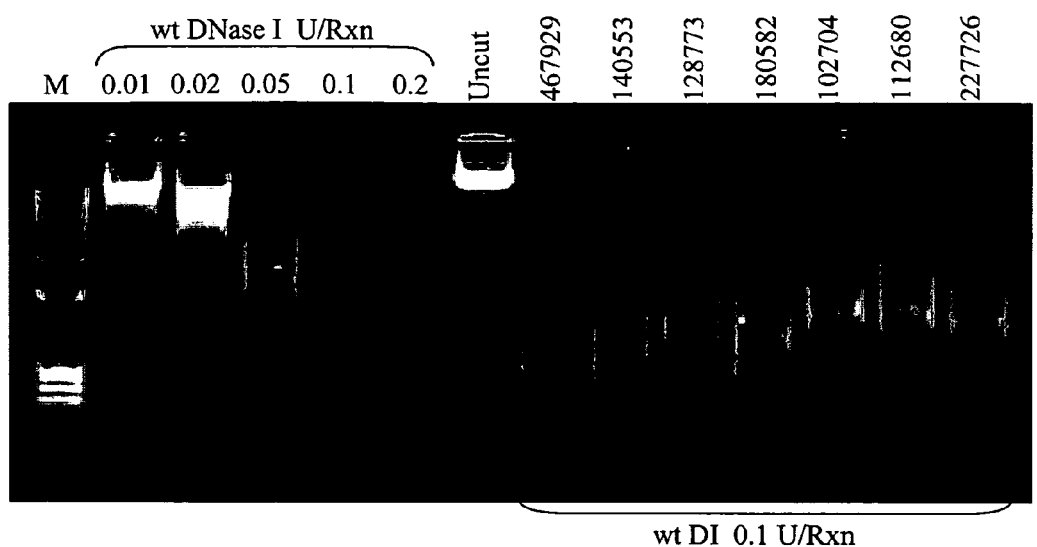
FIG. 10 Tolerance of compounds #467929, 140553, 128773, 180582, 102704, 112680, and 227726 in DNase I digestions.

Tolerance of Compounds #467929, 140553, 128773, 180582, 102704, 112680, and 227726 in DNase I Digestions Small molecule RNase inhibitors were tested in an industry-standard lambda digestion assay to determine if they inhibited DNase activity (0.1 U) at concentrations that were 5-fold above the apparent inhibition constant (i.e., $5 \times K_i$). Compounds #467929, 140553, and 180582 showed little or no DNase inhibition at these concentrations. Compounds #128773, 102704, 112680, and 227726, by comparison, were modestly inhibitory, relative to their potency for inhibiting RNase A (FIG. 10). As a result, compounds such as #467929, 140553, and 180582 may have utility in curbing the activity of residual RNases that may carry over from RNA isolation methods during DNase treatments of the RNA.

Example 28

Tolerance of Compounds #467929 and 227726 in qRT-PCR

The compatibility of #467929 and 227726 were tested in Ambion's MessageSensor RT-PCR Kit according to the supplier's instructions and using primers/probe designed to amplify a ~100 nt amplicon from the human CDC-2 mRNA. The reaction conditions were: 20-ul one-step RT-PCR with

TABLE 16

One-step RT-PCR With Benzopurpurin B and 4B. Target: hGAPDH

| Well # | Condition | Input RNA Ct at 50 ng | Input RNA Ct at 50 ng | Input RNA Ct at 50 ng | Input RNA Ct at 50 ng | Input RNA Ct at 50 ng | Std dev | Well 12 NTC |
|---|---|---|---|---|---|---|---|---|
| A | RT w RIP CONTROL | 17.15 | 17.19 | 17.29 | 17.14 | 17.16 | 0.061 | undet |
|  | Inhibitor Concentration: | 0 | 100 nm | 1 uM | 10 uM | 25 uM |  |  |
| B | RT w RIP + BpB | 16.83 | 17.27 | 17.66 | 19.27 | undet |  | undet |
| C | RT w RIP + Bp4B | 16.63 | 17.36 | 17.29 | 17.70 | undet |  | undet |
| D | RT + BpB | 16.32 | 17.39 | 17.35 | 17.96 | undet |  | undet |
| E | RT + Bp4B | 16.64 | 17.57 | 17.70 | 17.91 | undet |  | undet |
| 11 | Minus RT Control | undet |  |  |  |  |  |  |

Threshold = 0.1, Baseline Start = 2, Finish = 12

MMLV-RT (0.4 U/ul final) and SuperTaq (0.04 U/ul final). The cycling conditions were: Stage 1. 42 C for 15 minutes Stage 2. 95 C for 5 min, Stage 3. 95 C-15 sec and 60 C-60 sec where Stage 3 is repeated 40 times. The input template was HeLa-S3 total RNA at either 1 ng or 10 ng/reaction. As shown in Table 17, neither compound exerted untoward effects on RNA target detection sensitivity; 467929 was tolerated up to at least 100 uM, whereas 227726 was tolerated up to at least 1.3 mM. Consequently, these compounds may have utility in controlling any RNA degradation that might occur during the cDNA synthesis step of RT-PCR.

TABLE 17

| RNase Inhibitor | Inhibitor Concentration | Input RNA = 1 ng Cycle Threshold | Input RNA = 10 ng Cycle Threshold |
|---|---|---|---|
| None | N/A | 25.73 | 22.96 |
| None | N/A | 25.76 | 22.81 |
| 467929 | 10 uM | 25.79 | 23.05 |
| 467929 | 10 uM | 26.06 | 23.12 |
| 467929 | 50 uM | 25.84 | 22.82 |
| 467929 | 50 uM | 25.87 | 22.85 |
| 467929 | 100 uM | 25.32 | 22.49 |
| 467929 | 100 uM | 25.85 | 22.52 |
| 227726 | 130 uM | 26.01 | 23.18 |
| 227726 | 130 uM | 26.08 | 23.24 |
| 227726 | 655 uM | 26.14 | 23.01 |
| 227726 | 655 uM | 26.18 | 23.01 |
| 227726 | 1.3 mM | 26.08 | 23.02 |
| 227726 | 1.3 mM | 26.18 | 23.04 |

Example 29

Inhibition of RT-based RNase H Activity by Compound #467929

As described above, Chembridge compound #467929 offered protection from several RNA-specific endonucleolytic activities. Assays designed to measure inhibition of RNA cleavage from an RNA-DNA hybrid revealed that this compound was also a relatively potent inhibitor of reverse transcriptase RNase H activity. A 20-mer DNA oligonucleotide was asymmetrically annealed to a 1500 base synthetic RNA to create an RNA:DNA duplex substrate for RNase H. Reactions were initiated with 10 U of MMLV RT in 1× RT buffer (50 mM TrisCl pH 8.3, 75 mM KC, 3 mM $MgCl_2$, 5 mM DTT) containing 500 ng/ul RNA:DNA hybrid. All reactions contained 5% DMSO either with or without the small molecule RNase inhibitor. Samples were incubated for 5 min at 37 C, and quenched with EDTA. Products were resolved on an RNA LabChip. Cleavage products were observed as two equally represented RNA species of 1000 and 500 bases. Product length and yield were determined using the 2100 BioAnalyzer software (Agilent). Table 18 details the level of inhibition of MMLV RT RNase H that is observed as a function of the concentration of compounds 467929 and 227726. From these data it is clear that 467929 inhibits RT-based RNase H ($IC_{50}$~20 uM).

TABLE 18

| RNase Inhibitor | Inhibitor Concentration | % Cleavage |
|---|---|---|
| None | N/A | 36 |
| 467929 | 8 uM | 42 |
| 467929 | 40 uM | 8 |
| 467929 | 80 uM | ND* |
| 227726 | 100 uM | 45 |

TABLE 18-continued

| RNase Inhibitor | Inhibitor Concentration | % Cleavage |
|---|---|---|
| 227726 | 524 uM | 43 |
| 227726 | 1000 uM | 47 |

*ND = Not Detectable

Example 30

Figure 11:
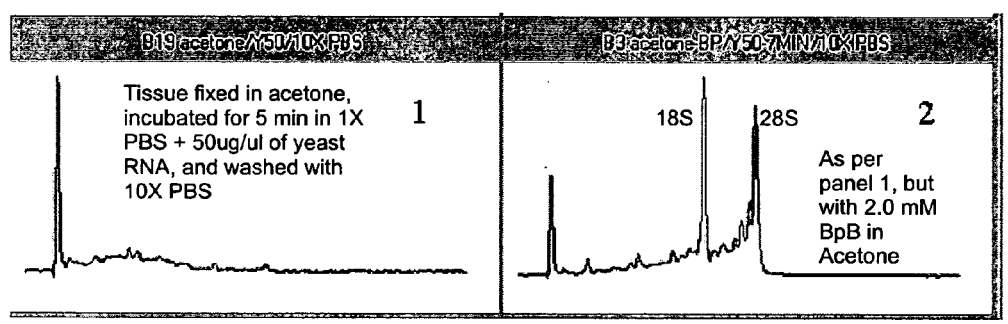
FIG. 11 Shows that Benzopurpurin B and analog enable the isolation of intact RNA from fixed tissue.
Figure 12:
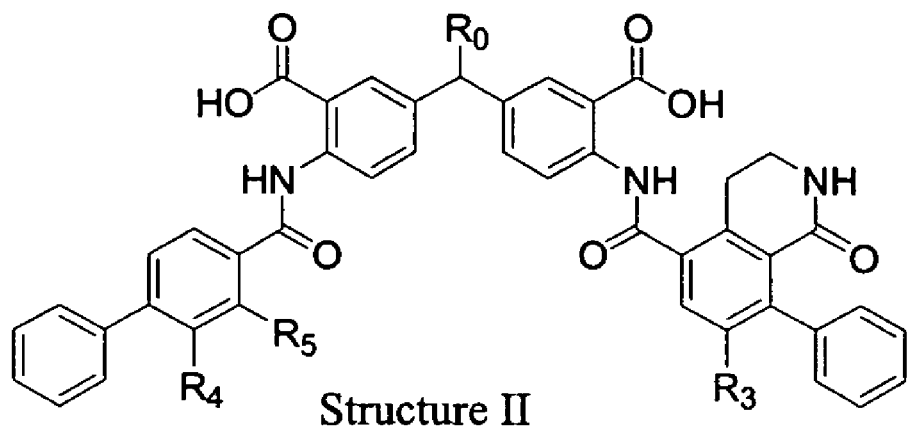
FIG. 12 shows derivatives of Structure II, Structure II being the chemical structure of a derivative of Structure I having —$(CH_2)_2NHCO$ substituted at Rhd 1 and $R_2$.
Figure 13:
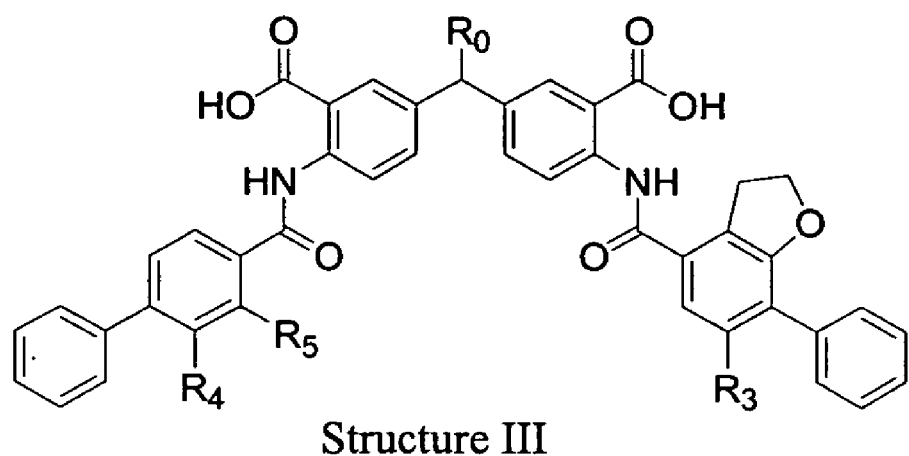
FIG. 13 shows Structure III, Structure III being the chemical structure of a derivative of Structure I having —$(CH_2)_2CO$ substituted at $R_1$ and $R_2$.

Benzopurpurin B and Analog Enables the Isolation of Intact RNA from Fixed Tissue Archived tissues are invaluable resource materials for gene expression studies, particularly using historical samples. RNA isolation from such samples often suffer from the same limitations that plague fresh tissues, namely the threat of RNA loss from omnipresent RNase activities. Small molecule RNase inhibitors could be extremely useful for such applications, particularly since this class of inhibitors is not nearly as vulnerable to inactivation in harsh chemicals, as are protein-based RNase inhibitors such as RNasin®. Moreover, small chemical inhibitors are often sufficiently small (MW≦500) and hydrophobic to diffuse into the tissue and blunt the action of cellular RNases. By comparison, protein inhibitors are too large to cross cellular membranes and protect RNA inside the cell itself. The inventors discovered the utility of chemical inhibitors in protecting RNA during the processing of frozen tissue sections for analysis by laser capture microdissection (LCM). Frozen mouse liver tissue sections (10 um thick) were first fixed for 4 min in ice-cold acetone, either with or without the BpB inhibitor. The sections were then incubated in 1×PBS for 5-20 min containing 50 ng/ul of yeast RNA. This step mimics the immunostaining step of the conventional protocol, where specific cellular sub-types are distinguished by dye binding and etched away from the unstained tissue by the LCM technique. Next, samples were briefly washed in 10×PBS and the tissue thrust into a guanidinium lysis buffer for subsequent RNA purification using a glass filter column (RNAqueous, Ambion). As shown by the RNA profiles of FIG. 11, the singular addition of 2 mM Benzopurpurin B in the acetone fixative is absolutely required for the isolation of intact total RNA using this procedure. Incorporation of the inhibitor into the 1×PBS solution during the incubation step allows the incubation times to be extended to up to 20 min without a significant loss of ribosomal RNA integrity. Either Benzopurin B or Benzopurpurin 4B can be used equally well in this application.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. patent application Ser. No. 10/352,806
Allewell and Sama, *Biochem. Biophys. ACTA,* 341:484-488, 1974.
Berger and Birkenmeier, Biochim. Biophys. ACTA, 562(1): 80-91, 1979.
Blackburn et al., *J. Biol. Chem.,* 252:5904-5910, 1977.
Blumberg, *Methods Enzymol.,* 152:20-24, 1987.
Chirgwin et al., *Biochemistry,* 18:5294-5299, 1979.
Chomczynski and Sacchi, *Biochem.,* 162:156-159, 1987.
Chomczynski, *Nucleic Acids Res.,* 20:3791, 1992.
Favaloro et al. *Methods Enzymol.,* 65(1):718-749, 1980.
Gilleland and Hockett, *Biotechniques,* 25:944-948, 1992.
Jocoli and Ronald, *Can J. Biochem.,* 51:1558-1565,1973.
Jones, *Biochem. Biophys. Res. Commun.,* 69:469-474, 1976.
Lin et al., *Biochem. Biophys. ACTA,* 263:680-682,1972.
Mendelsohn and Young, *Biochem. Biophys. ACTA,* 519:461-473, 1978.
Murphy et al., *Biotechniques,* 18:1068-1073, 1995.
Pelham and Jackson *Eur. J. Biochem.,* 67:247-256,1976.
Russo and Shapirom, *J. Biol. Chem.,* 274:14902-14908, 1999.
Sambrook et al., In: *Molecular cloning,* Cold Spring Harbor Laboratory Press, Cold Spring Harbor, N.Y., 2001.
Spackman et al., *J. Biol. Chem.,* 235:648-659, 1960.
Spider and Mackie, *J. Bacteriology,* 182(9): 2422-2427, 2000.
Wolf et al., *Eur. J. Biochem.,* 13:519-525, 1970.
Wu et al., In: *Methods In Gene Biotechnology,"* CRC Press, Boca Raton, Fla., 29-56, 1997.
Zale and Klibanov, *Biochem.,* 25:5432-5444, 1986.

What is claimed is:

1. A method comprising:
    a) obtaining at least a first nuclease inhibitor, wherein the first nuclease inhibitor is a RNase inhibitor protein or an anti-nuclease antibody;
    b) obtaining at least a second nuclease inhibitor wherein the second nuclease inhibitor is oligovinylsulfonic acid (OVA), aurintricarboxylic acid (ATA), aflatoxin, 2-nitro-5-thiocyanobenzoic acid, iodoacetate, N-bromosuccinimide, p-chloromercuribenzoate, dinitrofluorobenzene, decanavanate, polyvinylsufonic acid, hydrobenzoinphosphate, phenyiphosphate, putrescine, haloacetate, dinitrofluorobenzene, phenyiglyoxal, bromopyruvic, 8-amino-5-(4'-hydroxy-biphenyl-4-ylazo)-naphthalene-2-sulfonate, 6-hydroxy-5-(2-hydroxy-3,5-dinitro-phenylazo)-naphthalene-2-sulfonate, 3,3'-dimethylbiphenyl-4,4'-bis(2-amino-naphthylazo-6-sulfonate), 4,4'-dicarboxy-3,3-bis(naphthylamido)-diphenylmethanone, 3,3'-dicarboxy-4,4'-bis(4-biphenylamido)diphenylmethane, 3,3'-dicarboxy-4,4'-bis(3-nitrophenylamido)diphenylmethane or NCI-224131;
    c) obtaining a composition; and
    d) admixing the first nuclease inhibitor, the second nuclease inhibitor and the composition to form an admixture;
    wherein nucleases that may be present in the admixture are inhibited.

2. The method of claim 1, wherein the RNase inhibitor protein is obtained from a human, a chimpanzee, a rat, a mouse, a pig, yeast, or by recombinant means, or derivatives therein.

3. A method of performing an in vitro translation, transcription, reverse transcription or coupled transcription/translation reaction comprising obtaining a composition, the composition comprising the first nuclease inhibitor and a second nuclease inhibitor of claim 1 and placing the composition in an in vitro translation reaction, transcription reaction, reverse transcription reaction or a coupled transcription/translation reaction.

4. A solution comprising the first nuclease inhibitor and the second nuclease inhibitor of claim 1.

5. A kit comprising the first nuclease inhibitor and the second nuclease inhibitor of claim 1 and components for RNA isolation, an in vitro translation reaction, a reverse transcriptase reaction, an RNA amplification reaction, DNA removal, or in vitro transcription.

6. A method comprising:
    a) obtaining at least a first nuclease inhibitor, wherein the first nuclease inhibitor is a RNase inhibitor protein;
    b) obtaining at least a second nuclease inhibitor wherein the second nuclease inhibitor is purine, pyrimidine, cytidine-N3-oxide 2'-phosphate, 2'CMP, ppAp, Ap3A, Ap4A, Ap5A, ATP, 5'AMP, 5'ADP, 3'UMP, 2'UMP, 2'CMP, pAp (5'P-A-3'P), dUppAp, dUppA2'p, pdUppAp, pTp, pTppAp, TpdA, TppdA, 4-thiouridine 3'p, 5-nitro-uracil, 5-aminoethyl-uracil or (Bromoacetamido)nucleoside;
    c) obtaining a composition; and
    d) admixing the first nuclease inhibitor, the second nuclease inhibitor and the composition to form an admixture;
    wherein nucleases that may be present in the admixture are inhibited.

7. A method of performing an in vitro translation, transcription, reverse transcription or coupled transcription/translation reaction comprising obtaining a composition, the composition comprising the first nuclease inhibitor and a second nuclease inhibitor of claim 6 and placing the composition in an in vitro translation reaction, transcription reaction, reverse transcription reaction or a coupled transcription/translation reaction.

8. A solution comprising the first nuclease inhibitor and the second nuclease inhibitor of claim 6.

9. A kit comprising the first nuclease inhibitor and the second nuclease inhibitor of claim 6 and components for RNA isolation, an in vitro translation reaction, a reverse transcriptase reaction, an RNA amplification reaction, DNA removal, or in vitro transcription.

10. A method comprising:
    a) obtaining at least a first nuclease inhibitor, wherein the first nuclease inhibitor is an anti-RNase antibody or a RNase inhibitor protein;
    b) obtaining at least a second nuclease inhibitor wherein the second nuclease inhibitor is $SCN^-$, $Li^+$, $ClO_4^-$, or guanidinium;
    c) obtaining a composition; and
    d) admixing the first nuclease inhibitor, the second nuclease inhibitor and the composition to form an admixture;
    wherein nucleases that may be present in the admixture are inhibited.

11. A method of performing an in vitro translation, transcription, reverse transcription or coupled transcription/translation reaction comprising obtaining a composition, the composition comprising the first nuclease inhibitor and a second nuclease inhibitor of claim 10 and placing the composition in an in vitro translation reaction, transcription reaction, reverse transcription reaction or a coupled transcription/translation reaction.

12. A solution comprising the first nuclease inhibitor and the second nuclease inhibitor of claim 10.

13. A kit comprising the first nuclease inhibitor and the second nuclease inhibitor of claim 10 and components for RNA isolation, an in vitro translation reaction, a reverse transcriptase reaction, an RNA amplification reaction, DNA removal, or in vitro transcription.

14. A method comprising:
a) obtaining at least a first nuclease inhibitor, wherein the first nuclease inhibitor is an anti-RNase antibody or a RNase inhibitor protein;
b) obtaining at least a second nuclease inhibitor wherein the second nuclease inhibitor is an RNA or DNA oligonucleotide;
c) obtaining a composition; and
d) admixing the first nuclease inhibitor, the second nuclease inhibitor and the composition to form an admixture;
wherein nucleases that may be present in the admixture are inhibited.

15. A method of performing an in vitro translation, transcription, reverse transcription or coupled transcription/translation reaction comprising obtaining a composition, the composition comprising the first nuclease inhibitor and a second nuclease inhibitor of claim 14 and placing the composition in an in vitro translation reaction, transcription reaction, reverse transcription reaction or a coupled transcription/translation reaction.

16. A solution comprising the first nuclease inhibitor and the second nuclease inhibitor of claim 14.

17. A kit comprising the first nuclease inhibitor and the second nuclease inhibitor of claim 14 and components for RNA isolation, an in vitro translation reaction, a reverse transcriptase reaction, an RNA amplification reaction, DNA removal, or in vitro transcription.

18. A method comprising:
a) obtaining at least a first nuclease inhibitor, wherein the first nuclease inhibitor is an anti-RNase antibody or a RNase inhibitor protein;
b) obtaining at least a second nuclease inhibitor wherein the second nuclease inhibitor is an aptamer, a competitive inhibitor comprising a ribonucleoside, a deoxyribonucleoside, a dideoxyribonucleoside, a thiol-containing RNA, or a DNP-poly(A);
c) obtaining a composition; and
d) admixing the first nuclease inhibitor, the second nuclease inhibitor and the composition to form an admixture;
wherein nucleases that may be present in the admixture are inhibited.

19. A method of performing an in vitro translation, transcription, reverse transcription or coupled transcription/translation reaction comprising obtaining a composition, the composition comprising the first nuclease inhibitor and a second nuclease inhibitor of claim 18 and placing the composition in an in vitro translation reaction, transcription reaction, reverse transcription reaction or a coupled transcription/translation reaction.

20. A solution comprising the first nuclease inhibitor and the second nuclease inhibitor of claim 18.

21. A kit comprising the first nuclease inhibitor and the second nuclease inhibitor of claim 18 and components for RNA isolation, an in vitro translation reaction, a reverse transcriptase reaction, an RNA amplification reaction, DNA removal, or in vitro transcription.

22. A method comprising:
a) obtaining at least a first nuelease inhibitor, wherein the first nuclease inhibitor is an anti-nuclease antibody;
b) obtaining at least a second nuelease inhibitor wherein the second nuclease inhibitor comprises a non-proteinaceous polycyclic aromatic structure;
c) obtaining a composition; and
d) admixing the first nuclease inhibitor, the second nuclease inhibitor and the composition to form an admixture;
wherein nucleases that may be present in the admixture are inhibited.

23. The method of claim 22, wherein the aromatic structure is:

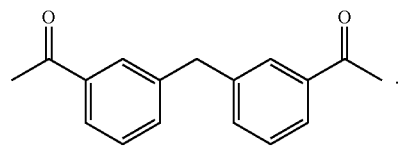

24. The method of claim 22, wherein the polycyclic aromatic structure is:

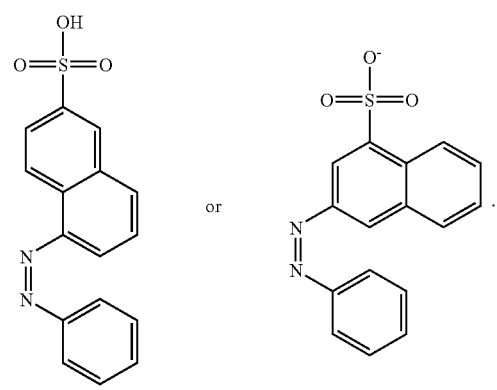

25. The method of claim 22, wherein the second nuclease inhibitor comprises the following structure:

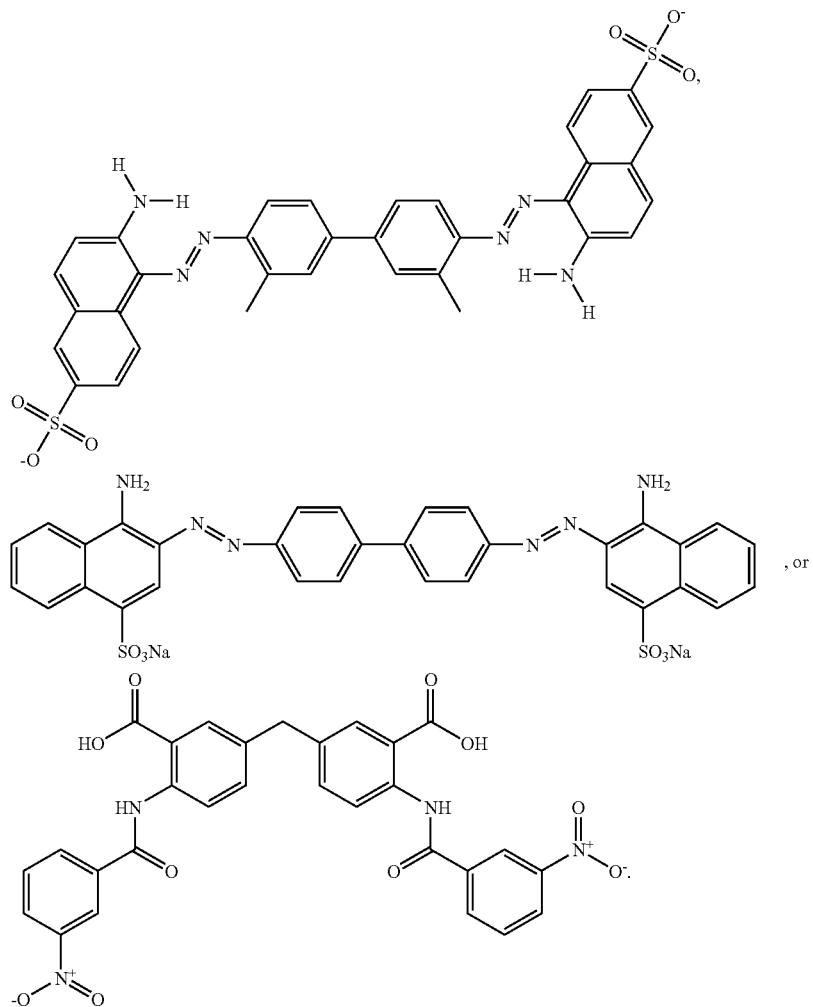

26. A method of performing an in vitro translation, transcription, reverse transcription or coupled transcription/translation reaction comprising obtaining a composition, the composition comprising the first nuclease inhibitor and a second nuclease inhibitor of claim 22 and placing the composition in an in vitro translation reaction, transcription reaction, reverse transcription reaction or a coupled transcription/translation reaction.

27. A solution comprising the first nuclease inhibitor and the second nuclease inhibitor of claim 22.

28. A kit comprising the first nuclease inhibitor and the second nuclease inhibitor of claim 22 and components for RNA isolation, an in vitro translation reaction, a reverse transcriptase reaction, an RNA amplification reaction, DNA removal, or in vitro transcription.

29. The method of claim 22, wherein the second nuclease inhibitor comprises a structure selected from the group consisting of NCI-65828, NCI 65845, benzopurpurin B, NCI-65841, NCI 79596, NCI-9617, NCI-16224, suramin, direct red 1, NCI-7815, NCI-45618, NCI-47740, prBZBP, NCI-65568, NCI-79741, NCI-65820, NCI-65553, NCI-58047, NCI-65847, xylidene ponceau 2R, eriochrome black T, amaranth, new coccine, acid red 37, acid violet 7, NCI-45608, NCI-75661, NCI-73416, NCI-724225, orange G, NCI 47755, sunset yellow, NCI-47735, NCI-37176, violamine R, NCI-65844, direct red 13, NCI-45601, NCI 75916, NCI-65546, NCI-65855, NCI-75963, NCI-45612, NCI-8674, NCI-75778, NCI-34933, NCI-1698, NCI-7814, NCI-45550, NCI-77521, cefsulodin, NCI-174066, NCI-12455, NCI-45541, NCI-79744, NCI-42067, NCI-45571, NCI-45538, NCI-45540, NCI-9360, NCI-12857, NCI-D726712, NCI-45542, NCI-7557, S321443, NCI-45557, NCI-1741, NCI-1743, NCI-227726, NCI-16163, NCI-16169, NCI-88947, NCI-17061, NCI-37169, beryllon II, CB-0181431, CB-473872, JLJ-1, JLJ-2, JLJ-3, CB-467929, CB-534510, CB-540408, CB-180582, CB-180553, CB-186847, CB-477474, CB-152591, NCI-37136, NCI-202516, CB-039263, CB-181145, CB-181429, CB-205125, and CB-224197.

30. The method of claim 29, wherein the second nuclease inhibitor is NCI-65828.

31. The method of claim 30, wherein the second nuclease inhibitor is a derivative of NCI-65828.

32. The method of claim 31, wherein the derivative of NCI-65828 comprises at least one modification selected from the group consisting of: a reduction of the azo to hydrazido, replacement of the azo by an amide, an attachment of a hydroxyl group to position 6 of the naphthalene ring, an attachment of an electron-withdrawing group to position 6 of the naphthalene ring, replacement of a carbon atom in an aromatic ring with a nitrogen or an oxygen, and a replacement of the hydroxyl group on the biphenyl component with a sulfonate.

33. The method of claim 29, wherein the second nuclease inhibitor is CB-473872.

34. The method of claim 33, wherein the second nuclease inhibitor is a derivative of CB-473872.

35. The method of claim 34, wherein the derivative of CB-473872 comprises an addition of at least one of a hydrogen-bonding group selected from the consisting of: a hydroxyl, an amino, a methyldiamino, a hydroxyethyl, an ethyl-N-formamido, a carboxyamido, a carboxy, a 2-oxo-N-piperidinyl, and a p-benzoyl.

36. The method of claim 34, wherein the derivative of CB-473872 comprises Structure II or Structure III, and wherein:
$R_0$ is —H, —NH$_2$, or —OH;
$R_3$ is —H, —CH$_2$OH, or CONH$_2$;
$R_4$ is —H, —COOH, or 2-oxo-N-piperidinyl;
$R_5$ is —H or p-benzoyl group.

37. The method of claim 34, wherein the derivative of CB-473872 comprises a replacement of a carbon atom in an aromatic ring with a nitrogen or an oxygen.

38. The method of claim 31, wherein the derivative of NCI-65828 comprises at least one modification selected from the group consisting of: an addition of a hydrogen-bonding group and substitution of a hydroxyl group with an anionic group to the biphenyl component.

39. The method of claim 38, wherein the hydrogen-bonding group is selected from the group consisting of a hydroxyl, an amino, and an amide.

40. The method of claim 38, wherein the anion is selected from the group consisting of a carboxylate, a sulfate, a sulfonate, a phosphate, and a phosphonate.

41. A method comprising
a) obtaining at least a first nuclease inhibitor, wherein the first nuclease inhibitor is benzopurpurin B;
b) obtaining at least a second nuclease inhibitor wherein the second nuclease inhibitor is an anti-nuclease antibody or a RNase inhibitor protein;
c) obtaining a composition; and
d) admixing the first nuclease inhibitor, the second nuclease inhibitor and the composition to form an admixture;
wherein nucleases that may be present in the admixture are inhibited.

42. A method of performing an in vitro translation, transcription, reverse transcription or coupled transcription/translation reaction comprising obtaining a composition, the composition comprising the first nuclease inhibitor and a second nuclease inhibitor of claim 41 and placing the composition in an in vitro translation reaction, transcription reaction, reverse transcription reaction or a coupled transcription/translation reaction.

43. A solution comprising the first nuclease inhibitor and the second nuclease inhibitor of claim 41.

44. A kit comprising the first nuclease inhibitor and the second nuclease inhibitor of claim 41 and components for RNA isolation, an in vitro translation reaction, a reverse transcriptase reaction, an RNA amplification reaction, DNA removal, or in vitro transcription.

45. A method comprising:
a) obtaining at least a first nuclease inhibitor, wherein the first nuclease inhibitor is cytidine-N3-oxide 2'-phosphate, 2'CMP, ppAp, Ap3A, Ap4A, Ap5A, ATP, 5'AMP, 5'ADP, 3'UMP, 2'UMP, 2'CMP, pAp (5'P-A-3'P), dUppAp, dUppA2'p, pdUppAp, pTp, pTppAp, TpdA, TppdA, 4-thiouridine 3'p, 5-nitro-uracil, 5-aminoethyl-uracil or (Bromoacetamido)nucleoside;
b) obtaining at least a second nuclease inhibitor wherein the second nuclease inhibitor comprises an anti-nuclease antibody;
c) obtaining a composition; and
d) admixing the first nuclease inhibitor, the second nuclease inhibitor and the composition to form an admixture;
wherein nucleases that may be present in the admixture are inhibited.

46. The method of claim 45, wherein the antibody is a soluble anti-nuclease antibody.

47. The method of claim 45, wherein the antibody is an anti-RNase antibody.

48. The method of claim 47, wherein the anti-RNase antibody is an anti-RNase T1 antibody or an anti-RNase 1 antibody.

49. A method of performing an in vitro translation, transcription, reverse transcription or coupled transcription/translation reaction comprising obtaining a composition, the composition comprising the first nuclease inhibitor and a second nuclease inhibitor of claim 45 and placing the composition in an in vitro translation reaction, transcription reaction, reverse transcription reaction or a coupled transcription/translation reaction.

50. A solution comprising the first nuclease inhibitor and the second nuclease inhibitor of claim 45.

51. A kit comprising the first nuclease inhibitor and the second nuclease inhibitor of claim 45 and components for RNA isolation, an in vitro translation reaction, a reverse transcriptase reaction, an RNA amplification reaction, DNA removal, or in vitro transcription.

52. A method comprising,
a) obtaining at least a first nuclease inhibitor, wherein the first nuclease inhibitor comprises a non-proteinaceous polycyclic aromatic structure;
b) obtaining at least a second nuclease inhibitor wherein the second nuclease inhibitor is a RNase inhibitor protein;
c) obtaining a composition; and
d) admixing the first nuclease inhibitor, the second nuclease inhibitor and the composition to form an admixture;
wherein nucleases that may be present in the admixture are inhibited.

53. A method of performing an in vitro translation, transcription, reverse transcription or coupled transcription/translation reaction comprising obtaining a composition, the composition comprising the first nuclease inhibitor and a second nuclease inhibitor of claim 52 and placing the composition in an in vitro translation reaction, transcription reaction, reverse transcription reaction or a coupled transcription/translation reaction.

54. A solution comprising the first nuclease inhibitor and the second nuclease inhibitor of claim 52.

55. A kit comprising the first nuclease inhibitor and the second nuclease inhibitor of claim 52 and components for RNA isolation, an in vitro translation reaction, a reverse transcriptase reaction, an RNA amplification reaction, DNA removal, or in vitro transcription.

56. The method of claim 52, wherein the aromatic structure is:

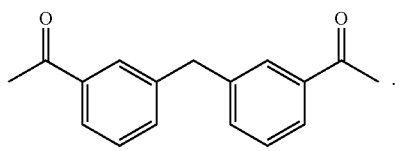
57. The method of claim 52, wherein the aromatic structure is:
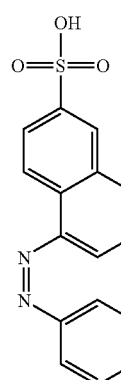 or 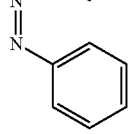
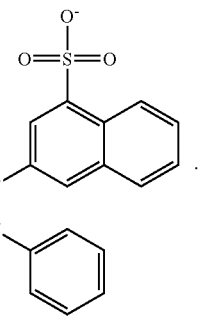
58. The method of claim 52, wherein the aromatic structure is:
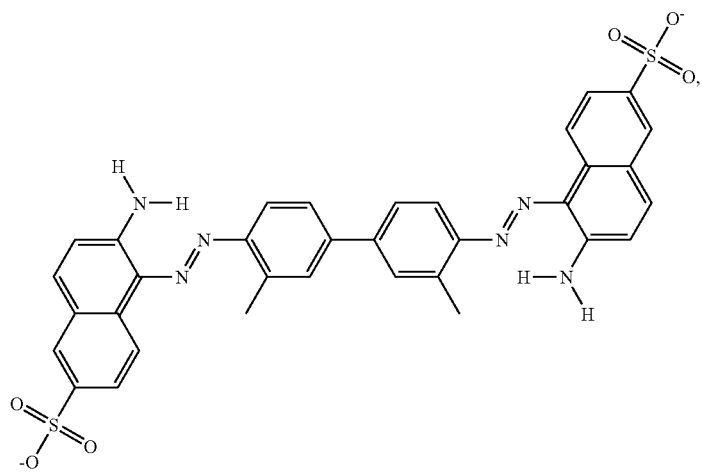
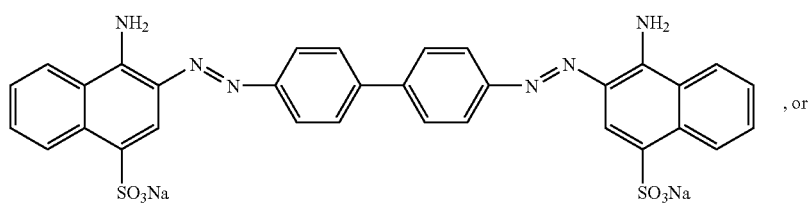, or -continued

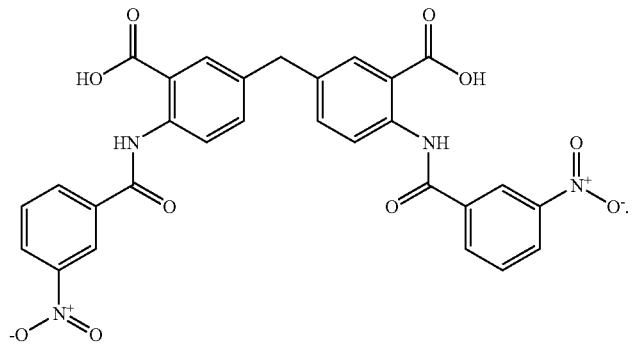

59. The method of claim 52, wherein the aromatic structure is selected from the group consisting of NCI-65828, NCI 65845, benzopurpurin B, NCI-65841, NCI 79596, NCI-9617, NCI-16224, suramin, direct red 1, NCI-7815, NCI-45618, NCI-47740, prBZBP, NCI-65568, NCI-79741, NCI-65820, NCI-65553, NCI-58047, NCI-65847, xylidene ponceau 2R, eriochrome black T, amaranth, new coccine, acid red 37, acid violet 7, NCI-45608, NCI-75661, NCI-73416, NCI-724225, orange G, NCI 47755, sunset yellow, NCI-47735, NCI-37176, violamine R, NCI-65844, direct red 13, NCI-45601, NCI 75916, NCI-65546, NCI-65855, NCI-75963, NCI-45612, NCI-8674, NCI-75778, NCI-34933, NCI-1698, NCI-7814, NCI-45550, NCI-77521, cefsulodin, NCI-174066, NCI-12455, NCI-45541, NCI-79744, NCI-42067, NCI-45571, NCI-45538, NCI-45540, NCI-9360, NCI-12857, NCI-D726712, NCI-45542, NCI-7557, S321443, NCI-45557, NCI-1741, NCI-1743, NCI-227726, NCI-16163, NCI-16169, NCI-88947, NCI-17061, NCI-37169, beryllon II, CB-0181431, CB-473872, JLJ-1, JLJ-2, JLJ-3, CB-467929, CB-534510, CB-540408, CB-180582, CB-180553, CB-186847, CB-477474, CB-152591, NCI-37136, NCI-202516, CB-039263, CB-181145, CB-181429, CB-205125, and CB-224197.

60. The method of claim 59, wherein the aromatic structure is NCI-65828.

61. The method of claim 60, wherein the aromatic structure is a derivative of NCI-65828.

62. The method of claim 61, wherein the derivative of NCI-65828 comprises at least one modification selected from the group consisting of: a reduction of the azo to hydrazido, replacement of the azo by an amide, an attachment of a hydroxyl group to position 6 of the naphthalene ring, an attachment of an electron-withdrawing group to position 6 of the naphthalene ring, replacement of a carbon atom in an aromatic ring with a nitrogen or an oxygen, and a replacement of the hydroxyl group on the biphenyl component with a sulfonate.

63. The method of claim 61, wherein the derivative of NCI-65828 comprises at least one modification selected from the group consisting of: an addition of a hydrogen-bonding group and substitution of a hydroxyl group with an anionic group to the biphenyl component.

64. The method of claim 63, wherein the hydrogen-bonding group is selected from the group consisting of a hydroxyl, an amino, and an amide.

65. The method of claim 63, wherein the anion is selected from the group consisting of a carboxylate, a sulfate, a sulfonate, a phosphate, and a phosphonate.

66. The method of claim 59, wherein the aromatic structure is CB-473872.

67. The method of claim 66, wherein the aromatic structure is a derivative of CB-473872.

68. The method of claim 67, wherein the derivative of CB-473872 comprises an addition of at least one of a hydrogen-bonding group selected from the consisting of: a hydroxyl, an amino, a methyldiamino, a hydroxyethyl, an ethyl-N-formamido, a carboxyamido, a carboxy, a 2-oxo-N-piperidinyl, and a p-benzoyl.

69. The method of claim 67, wherein the derivative of CB-473872 comprises Structure II or Structure III, and wherein:

$R_0$ is —H, —NH$_2$, or —OH;
$R_3$ is —H, —CH$_2$OH, or CONH$_2$;
$R_4$ is —H, —COOH, or 2-oxo-N-piperidinyl;
$R_5$ is —H or p-benzoyl group.

70. The method of claim 67, wherein the derivative of CB-473872 comprises a replacement of a carbon atom in an aromatic ring with a nitrogen or an oxygen.

71. A method comprising:
a) obtaining at least a first nuclease inhibitor, wherein the first nuclease inhibitor is a a salt, wherein the salt is NaCitrate;
b) obtaining at least a second nuclease inhibitor wherein the second nuclease inhibitor comprises an anti-RNase antibody or an RNase inhibitor protein;
c) obtaining a composition; and
d) admixing the first nuclease inhibitor, the second nuclease inhibitor and the composition to form an admixture;
wherein nucleases that may be present in the admixture are inhibited.

72. A method of performing an in vitro translation, transcription, reverse transcription or coupled transcription/translation reaction comprising obtaining a composition, the composition comprising the first nuclease inhibitor and a second nuclease inhibitor of claim 71 and placing the composition in an in vitro translation reaction, transcription reaction, reverse transcription reaction or a coupled transcription/translation reaction.

73. A solution comprising the first nuclease inhibitor and the second nuclease inhibitor of claim 71.

74. A kit comprising the first nuclease inhibitor and the second nuclease inhibitor of claim 71 and components for RNA isolation, an in vitro translation reaction, a reverse transcriptase reaction, an RNA amplification reaction, DNA removal, or in vitro transcription.

75. A method comprising:
a) obtaining at least a first nuclease inhibitor, wherein the first nuclease inhibitor is an RNA or DNA oligonucleotide;
b) obtaining at least a second nuclease inhibitor;
c) obtaining a composition; and
d) admixing the first nuclease inhibitor, the second nuclease inhibitor and the composition to form an admixture;
wherein nucleases that may be present in the admixture are inhibited.

76. A method comprising:
a) obtaining at least a first nuclease inhibitor, wherein the first nuclease inhibitor is an RNA or DNA oligonucleotide, an aptamer, or a competitive inhibitor comprising a deoxyribonucleoside, a dideoxyribonucleoside, a thiol-containing RNA, or a DNP-poly(A).
b) obtaining at least a second nuclease inhibitor;
c) obtaining a composition; and
d) admixing the first nuclease inhibitor, the second nuclease inhibitor and the composition to form an admixture;
wherein nucleases that may be present in the admixture are inhibited.

77. A method comprising:
a) obtaining at least a first nuclease inhibitor, wherein the first nuclease inhibitor is an affinity resin;
b) obtaining at least a second nuclease inhibitor;
c) obtaining a composition; and
d) admixing the first nuclease inhibitor, the second nuclease inhibitor and the composition to form an admixture;
wherein nucleases that may be present in the admixture are inhibited.

78. The method of claim 77, wherein the affinity resin is sulfopropyl sepharose or SP sulfopropyl cation exchange resin.

* * * * *

UNITED STATES PATENT AND TRADEMARK OFFICE
CERTIFICATE OF CORRECTION

PATENT NO. : 7,264,932 B2 Page 1 of 1
APPLICATION NO. : 10/786875
DATED : September 4, 2007
INVENTOR(S) : Gary J. Latham et al.

It is certified that error appears in the above-identified patent and that said Letters Patent is hereby corrected as shown below:

In claim 1, column 99, line 49, delete "phenyiphosphate" and insert --phenylphosphate-- therefor.

In claim 1, column 99, line 50, delete "phenyiglyoxal" and insert --phenylglyoxal-- therefor.

In claim 1, column 99, line 55, delete "3-bis" and insert --3'-bis-- therefor.

In claim 1, column 99, line 63, delete "admixture:" and insert --admixture;-- therefor.

In claim 22, column 102, line 9, delete "nuelease" and insert --nuclease-- therefor.

In claim 22, column 102, line 11, delete "nuelease" and insert --nuclease-- therefor.

Signed and Sealed this

Eleventh Day of December, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,264,932 B2 | Page 1 of 1 |
| APPLICATION NO. | : 10/786875 | |
| DATED | : September 4, 2007 | |
| INVENTOR(S) | : Gary J. Latham et al. | |

It is certified that error appears in the above-identified patent and that said Letters Patent is hereby corrected as shown below:

In Title Page, Item (*) Notice, please insert at line 4 --This patent is subject to a terminal disclaimer.--.

Signed and Sealed this

Twenty-seventh Day of May, 2008

JON W. DUDAS
*Director of the United States Patent and Trademark Office*